US009199019B2

(12) United States Patent
Callaway et al.

(10) Patent No.: US 9,199,019 B2
(45) Date of Patent: Dec. 1, 2015

(54) VENTRICULAR CUFF

(71) Applicant: Thoratec Corporation, Pleasanton, CA (US)

(72) Inventors: Justin Aron Callaway, Goffstown, NH (US); Cori G. Pierce, Wakefield, MA (US); Julien Duhamel, Billerica, MA (US); Kevin Bourque, Reading, MA (US)

(73) Assignee: THORATEC CORPORATION, Pleasanton, CA (US)

( * ) Notice: Subject to any disclaimer, the term of this patent is extended or adjusted under 35 U.S.C. 154(b) by 0 days.

(21) Appl. No.: 13/842,578

(22) Filed: Mar. 15, 2013

(65) Prior Publication Data
US 2014/0067057 A1    Mar. 6, 2014

Related U.S. Application Data

(60) Provisional application No. 61/695,925, filed on Aug. 31, 2012.

(51) Int. Cl.
*A61M 1/10* (2006.01)
*A61M 1/12* (2006.01)

(52) U.S. Cl.
CPC ............... *A61M 1/10* (2013.01); *A61M 1/1008* (2014.02); *A61M 1/1001* (2014.02); *A61M 1/12* (2013.01); *A61M 1/122* (2014.02)

(58) Field of Classification Search
CPC ......... A61M 1/12; A61M 1/10; A61M 1/122; A61M 1/101; A61M 1/1001; A61M 1/1008; A61F 2/24
USPC ..................... 623/3.1, 3.26; 600/16
See application file for complete search history.

(56) References Cited

U.S. PATENT DOCUMENTS 3,766,567 A * 10/1973 Kahn et al. .................... 623/3.21
4,099,759 A *  7/1978 Kornhauser .................. 293/110
4,458,366 A    7/1984 MacGregor
4,688,998 A    8/1987 Olsen et al.

(Continued)

FOREIGN PATENT DOCUMENTS

CA    2526920        2/2009
CN    1842354 A     10/2006

(Continued)

OTHER PUBLICATIONS

International Search Report and Written Opinion for Application No. PCT/US2013/056952, dated Nov. 19, 2013, 16 pages.
Barletta et al., "Design of a Bearingless Blood Pump," in Proceedings Third International Symposium on Magnetic Suspension Technology, Tallahassee, FL, 1995, pp. 265-274.
"Nickel titanium," Wikipedia [online] Mar. 10, 2013 [retrieved on Mar. 12, 2013]. Retrieved from the Internet: < URL: http://en.wikipedia.org/wiki/Nickel_titanium>, 8 pages.

(Continued)

*Primary Examiner* — Thomas J Sweet
*Assistant Examiner* — Rokhaya Diop
(74) *Attorney, Agent, or Firm* — Kilpatrick Townsend & Stockton LLP

(57) ABSTRACT

In one general aspect, a cuff for attachment to a heart includes an attachment component configured to engage a blood pump to attach the cuff to the blood pump and a sewing ring for attachment to the heart. The sewing ring is coupled to the attachment component, and the attachment component and the sewing ring each define a central opening configured to admit an inflow cannula of a blood pump. The sewing ring comprises a member that provides rigidity to flatten a portion of a myocardium of the heart when the cuff is attached to the heart.

31 Claims, 54 Drawing Sheets

(56) References Cited

U.S. PATENT DOCUMENTS

| | | | |
|---|---|---|---|
| 4,769,031 A | 9/1988 | McGough et al. | |
| 5,055,005 A | 10/1991 | Kletschka | |
| 5,098,369 A | 3/1992 | Heilman et al. | |
| 5,139,517 A | 8/1992 | Corral | |
| 5,195,877 A | 3/1993 | Kletschka | |
| 5,222,980 A | 6/1993 | Gealow | |
| 5,275,580 A | 1/1994 | Yamazaki | |
| 5,456,714 A | 10/1995 | Owen | |
| 5,470,208 A | 11/1995 | Kletschka | |
| 5,708,346 A | 1/1998 | Schob | |
| 5,814,005 A | 9/1998 | Barra et al. | |
| 5,827,316 A | 10/1998 | Young et al. | |
| 5,843,088 A | 12/1998 | Barra et al. | |
| 5,984,956 A | 11/1999 | Tweden et al. | |
| 6,001,056 A | 12/1999 | Jassawalla et al. | |
| 6,050,975 A | 4/2000 | Poirier | |
| 6,066,085 A | 5/2000 | Heilman et al. | |
| 6,146,325 A | 11/2000 | Lewis et al. | |
| 6,238,334 B1 | 5/2001 | Easterbrook, III et al. | |
| 6,254,564 B1 | 7/2001 | Wilk et al. | |
| 6,346,071 B1 | 2/2002 | Mussivand | |
| 6,390,976 B1 | 5/2002 | Spence et al. | |
| 6,669,708 B1 | 12/2003 | Nissenbaum et al. | |
| 6,673,043 B1 | 1/2004 | Landesberg | |
| 6,689,147 B1 | 2/2004 | Koster | |
| 6,705,988 B2 | 3/2004 | Spence et al. | |
| 6,726,648 B2 | 4/2004 | Kaplon et al. | |
| 6,732,501 B2 | 5/2004 | Yu et al. | |
| 6,802,806 B2 | 10/2004 | McCarthy et al. | |
| 6,808,498 B2 | 10/2004 | Laroya et al. | |
| 6,863,677 B2 | 3/2005 | Breznock | |
| 6,942,672 B2 | 9/2005 | Heilman et al. | |
| 6,994,666 B2 | 2/2006 | Shannon et al. | |
| 7,018,384 B2 | 3/2006 | Skakoon | |
| 7,048,681 B2 | 5/2006 | Tsubouchi et al. | |
| 7,056,286 B2 | 6/2006 | Ravenscroft et al. | |
| 7,077,801 B2 | 7/2006 | Haverich | |
| 7,214,234 B2 | 5/2007 | Rapacki et al. | |
| 7,404,792 B2 | 7/2008 | Spence et al. | |
| 7,462,019 B1 | 12/2008 | Allarie et al. | |
| 7,824,358 B2* | 11/2010 | Cotter et al. | 604/6.16 |
| 8,152,845 B2 | 4/2012 | Bourque | |
| 8,500,759 B2* | 8/2013 | Koyfman et al. | 606/151 |
| 8,579,790 B2 | 11/2013 | Jeffery et al. | |
| 2002/0045846 A1* | 4/2002 | Kaplon et al. | 604/9 |
| 2002/0095210 A1 | 7/2002 | Finnegan et al. | |
| 2003/0023255 A1 | 1/2003 | Miles et al. | |
| 2003/0040765 A1 | 2/2003 | Breznock | |
| 2003/0130668 A1 | 7/2003 | Nieman et al. | |
| 2004/0002624 A1 | 1/2004 | Yu et al. | |
| 2004/0054251 A1* | 3/2004 | Liotta | 600/17 |
| 2004/0153112 A1 | 8/2004 | Nissenbaum et al. | |
| 2004/0171905 A1 | 9/2004 | Yu et al. | |
| 2004/0236170 A1 | 11/2004 | Kim | |
| 2005/0033107 A1 | 2/2005 | Tsubouchi | |
| 2005/0101982 A1 | 5/2005 | Ravenscroft et al. | |
| 2005/0131451 A1 | 6/2005 | Kleshinski et al. | |
| 2005/0149093 A1 | 7/2005 | Pokorney | |
| 2005/0154411 A1 | 7/2005 | Breznock et al. | |
| 2005/0209502 A1 | 9/2005 | Schmid et al. | |
| 2005/0251187 A1 | 11/2005 | Beane et al. | |
| 2006/0036313 A1 | 2/2006 | Vassiliades | |
| 2006/0089707 A1 | 4/2006 | Vassiliades et al. | |
| 2006/0099716 A1 | 5/2006 | Tipler et al. | |
| 2006/0142634 A1 | 6/2006 | Anstadt et al. | |
| 2006/0161193 A1 | 7/2006 | Beane et al. | |
| 2007/0088375 A1 | 4/2007 | Beane et al. | |
| 2007/0100363 A1 | 5/2007 | Dollar et al. | |
| 2007/0106315 A1 | 5/2007 | Gregoric et al. | |
| 2007/0134993 A1 | 6/2007 | Tamez et al. | |
| 2007/0167968 A1 | 7/2007 | Pandey | |
| 2007/0167969 A1 | 7/2007 | Pandey | |
| 2007/0173879 A1 | 7/2007 | Pandey | |
| 2007/0265643 A1 | 11/2007 | Beane et al. | |
| 2008/0009668 A1 | 1/2008 | Cohn | |
| 2008/0009887 A1 | 1/2008 | Cohn | |
| 2008/0009891 A1 | 1/2008 | Cohn | |
| 2008/0076959 A1 | 3/2008 | Farnan et al. | |
| 2009/0012552 A1 | 1/2009 | Pandey et al. | |
| 2009/0143638 A1 | 6/2009 | Keogh et al. | |
| 2009/0171136 A1 | 7/2009 | Shambaugh | |
| 2010/0305692 A1 | 12/2010 | Thomas et al. | |
| 2011/0118766 A1 | 5/2011 | Reichenbach | |
| 2011/0118829 A1* | 5/2011 | Hoarau et al. | 623/2.11 |
| 2011/0118833 A1 | 5/2011 | Reichenbach et al. | |
| 2011/0160850 A1* | 6/2011 | Bourque | 623/3.1 |
| 2012/0010455 A1 | 1/2012 | Reichenbach et al. | |
| 2012/0059212 A1 | 3/2012 | LaRose et al. | |
| 2012/0165931 A1 | 6/2012 | Bourque | |
| 2012/0226096 A1 | 9/2012 | Callaway et al. | |

FOREIGN PATENT DOCUMENTS

| | | |
|---|---|---|
| DE | 10108809 A1 | 9/2002 |
| EP | 1706168 | 10/2006 |
| JP | 2007510522 A | 4/2007 |
| JP | 2013-510691 A | 3/2013 |
| WO | WO0074747 A1 | 12/2000 |
| WO | WO03001980 A2 | 1/2003 |
| WO | WO2004014456 A2 | 2/2004 |
| WO | WO2005046783 A1 | 5/2005 |
| WO | WO2007038109 A2 | 4/2007 |
| WO | WO 2007038109 A2 * | 4/2007 |
| WO | WO2008131453 A1 | 10/2008 |
| WO | WO 2009085243 A1 * | 7/2009 |
| WO | WO2009085243 A1 | 7/2009 |
| WO | WO 2011/060386 A2 | 5/2011 |

OTHER PUBLICATIONS

Thompson, "An overview of nickel-titanium alloys used in dentistry," International Endodontic Journal, 33:297-310, 2000.

International Preliminary Report on Patentability for Application No. PCT/US2009/069836, issued Jul. 4, 2012, 8 pages.

International Preliminary Report on Patentability for PCT/US2012/027481, issued Sep. 3, 2013, 10 pages.

International Search Report and Written Opinion for Application No. PCT/US2009/069836, dated Sep. 20, 2010, 12 pages.

International Search Report and Written Opinion for Application No. PCT/US2012/027481 dated Jun. 6, 2012, 15 pages.

U.S. Non-Final Office Action for U.S. Appl. No. 12/650,017 mailed Jun. 27, 2011, 9 pages.

U.S. Notice of Allowance for U.S. Appl. No. 12/650,017 mailed Jan. 4, 2012, 7 pages.

U.S. Non-Final Office Action for U.S. Appl. No. 13/414,041, mailed Apr. 9, 2013, 4 pages.

U.S. Appl. No. 13/832,657, filed Mar. 15, 2013, first named inventor: Justin Aron Callaway.

Notification Of Transmittal Of The International Search Report And The Written Opinion Of The International Searching Authority, Or The Declaration; International Search Report and Written Opinion Of The International Searching Authority for corresponding International Application No. PCT/US2013/056952 mailed on Nov. 19, 2013, 16 pages.

Notification Of Transmittal Of The International Search Report And The Written Opinion Of The International Searching Authority, Or The Declaration; International Search Report and Written Opinion Of The International Searching Authority for corresponding International Application No. PCT/US2014/021389 mailed on Jun. 24, 2014, 12 pages.

Notification of Transmittal of The International Search Report and The Written Opinion of The International Searching Authority, or The Declaration; International Search Report and Written Opinion of the International Searching Authority for corresponding International Application No. PCT/US2015/019308 mailed on Jul. 14, 2015, 15 pages.

\* cited by examiner

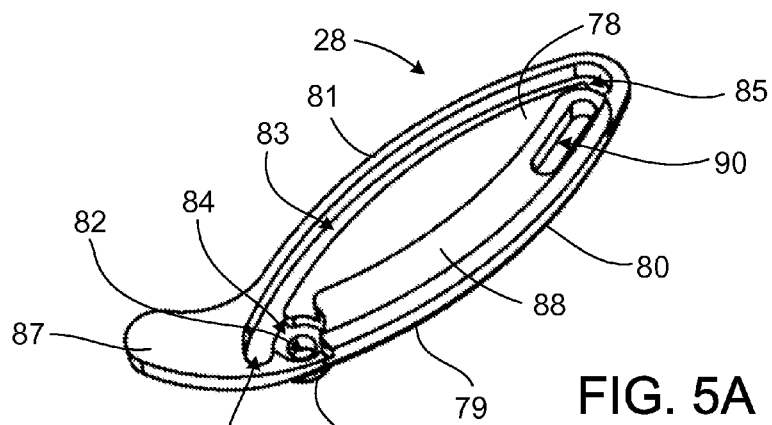
FIG. 5A
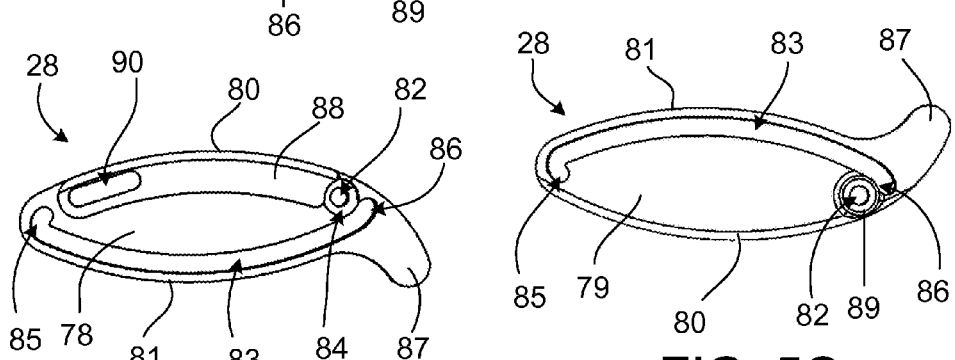
FIG. 5B
FIG. 5C
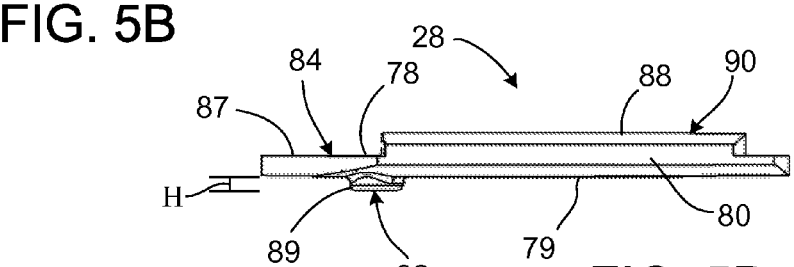
FIG. 5D
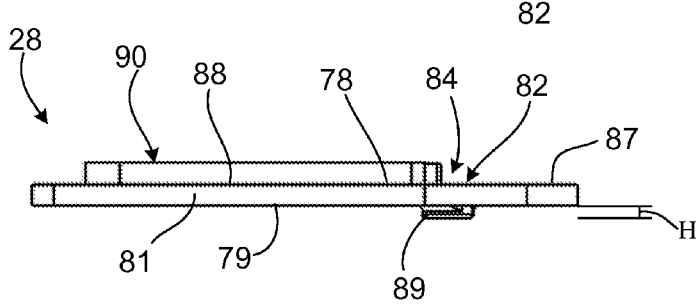
FIG. 5E

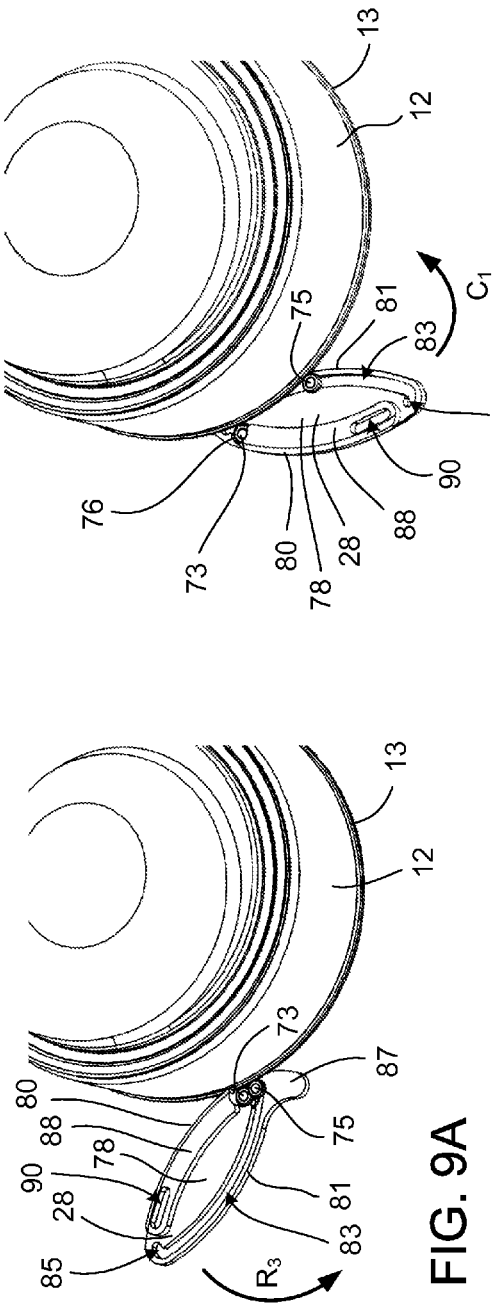
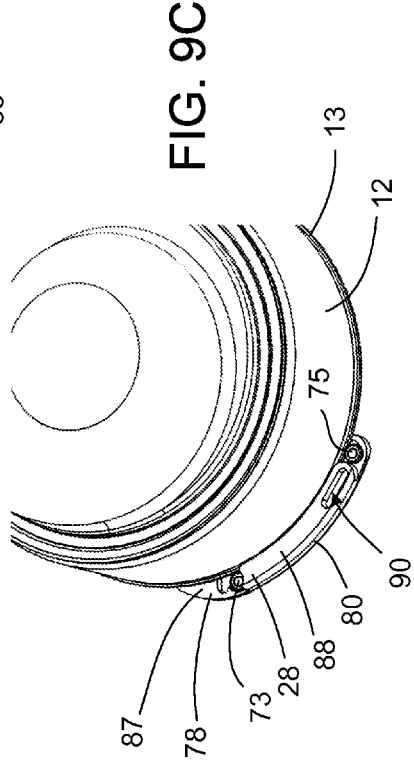

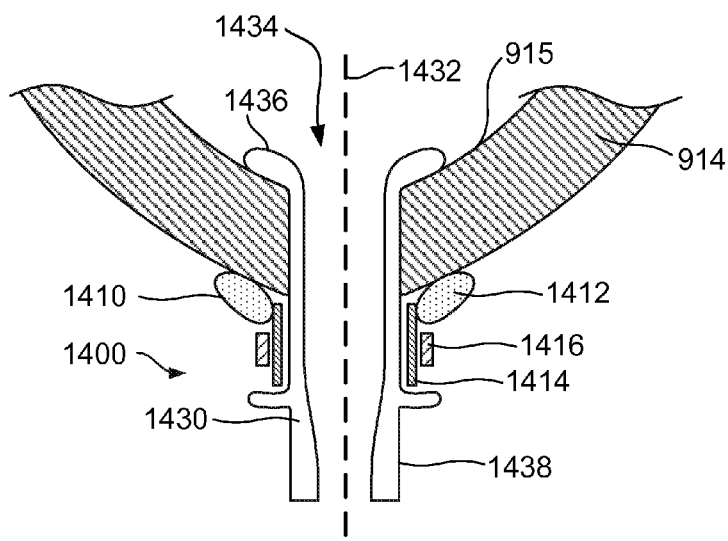
FIG. 41
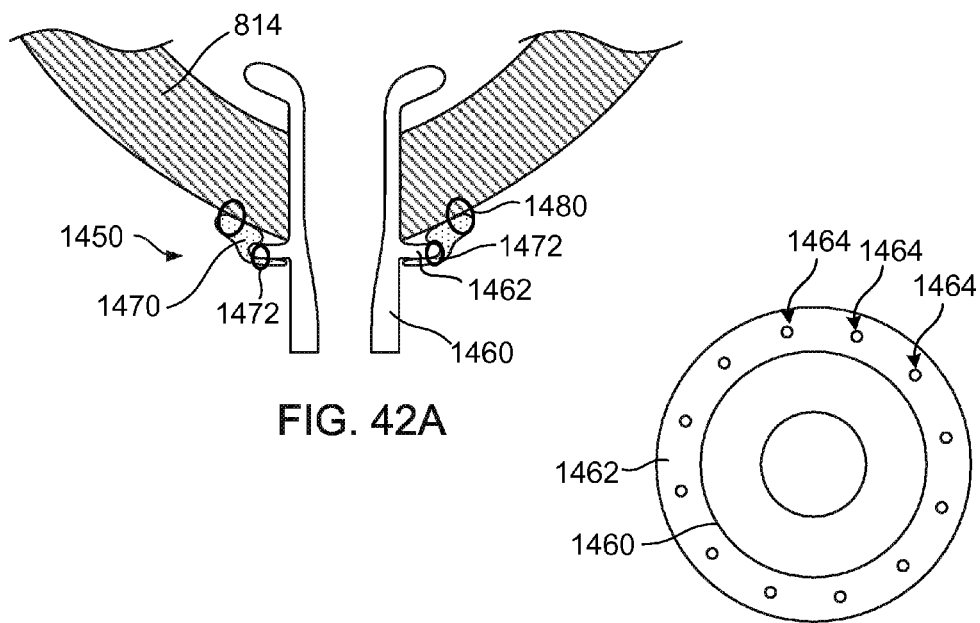
FIG. 42A
FIG. 42B

VENTRICULAR CUFF

CROSS-REFERENCE TO RELATED APPLICATION

This application claims priority to and the full benefit of U.S. Provisional Patent Application No. 61/695,925, filed Aug. 31, 2012, and titled "VENTRICULAR CUFF," which is incorporated herein by reference.

TECHNICAL FIELD

This disclosure relates to ventricular cuffs.

BACKGROUND

Heart assist devices or pumps can be inserted in the circulatory system to pump blood from either ventricle or atrium of a heart to the vasculature. A pump supplementing a ventricle is known as a ventricular assist device, or VAD. A VAD is useful when the ventricle alone is incapable of providing adequate blood flow.

SUMMARY

In a general aspect, a cuff for attachment to a heart defines an opening to admit a cannula of a heart pump. The cuff can be sufficiently rigid to promote flattening of the myocardium in a region where the cuff is attached.

In some implementations, the cuff includes two or more layers of, for example, felt, fabric, mesh, or another material. The two or more layers may be joined by sutures or an adhesive, such as a silicone adhesive. In some implementations, the cuff includes a wire insert, which may be covered in silicone and positioned between two layers of felt.

In another general aspect, a housing of a heart pump includes one or more anchors. The anchors admit fasteners, such as sutures, that can secure the implanted heart pump.

In some implementations, multiple anchors are located at the perimeter of the heart pump, for example, spaced apart around an outer edge of the housing. Each anchor may be a suture anchor, for example, an eyelet or other opening through which a suture can be passed to capture a portion of the housing.

In another general aspect, fabric cover is implanted around a blood pump to reduce tissue adhesion and facilitate later removal of the blood pump.

In another general aspect, a blood pump includes a housing disposed about a pump mechanism. The housing has a proximal side configured to face toward a heart and an inflow cannula extending from the proximal side. The housing has an outer perimeter, and the housing includes a plurality of suture anchors disposed along the outer perimeter of the housing.

Implementations may include one or more of the following features. For example, the suture anchors are eyelets defined through the housing. The housing has a peripheral side oriented generally perpendicular to the proximal side, and one or more of the eyelets defines a passage from the peripheral side to the proximal side. The passage extends from the peripheral side inward toward the inflow cannula. The passage has a central axis, and the central axis is oriented at an angle of between 20 degrees and 50 degrees of the peripheral side. The housing is configured to receive a ventricular cuff about the inflow cannula with the ventricular cuff adjacent the proximal side, and each of the plurality of suture anchors defines a passage oriented to direct a needle through the ventricular cuff when the ventricular cuff is positioned about the inflow cannula with the ventricular cuff adjacent the proximal side. The outer perimeter of the housing is generally circular and the housing has a circumference, and the suture anchors are spaced apart along at least a portion of the circumference. Thee suture anchors are disposed around more than half of the circumference. The suture anchors are spaced apart at an angular distance of between 10 and 50 degrees. The inflow cannula defines a central longitudinal axis, and the suture anchors each have an opening disposed in a plane, the plane being generally perpendicular to the central longitudinal axis of the inflow cannula.

In another general aspect, a cuff for attachment to a heart includes an attachment component configured to engage a blood pump to attach the cuff to the blood pump. The cuff also includes a sewing ring for attachment to the heart. The sewing ring is coupled to the attachment component, and the attachment component and the sewing ring each define a central opening configured to admit an inflow cannula of a blood pump. The sewing ring includes a member that provides rigidity to flatten a portion of a myocardium of the heart when the cuff is attached to the heart.

Implementations may include one or more of the following features. For example, the sewing ring includes two or more disc-shaped layers of fabric. The two or more disc-shaped layers are formed of a felt, a mesh, or a woven material. The two or more disc-shaped layers are formed of polytetrafluoroethylene, polyester, or polyethylene terephthalate. The two or more disc-shaped layers are formed of polytetrafluoroethylene felt. The two or more disc-shaped layers are attached to each other by sutures or an adhesive. Each of the two or more disc-shaped layers has a thickness between approximately 1.3 millimeters and 2.3 millimeters, and a maximum water permeability of between approximately 450 ml/cm2/min and 650 ml/cm2/min. The sewing ring includes an insert disposed between the disc-shaped layers, the insert being more rigid than the disc-shaped layers. The insert is formed of polyether ether ketone, titanium, a titanium alloy, a cobalt chromium alloy, or a shape-memory polymer. The insert is covered in silicone. The insert is a lattice or web that defines a central opening that admits the inflow cannula of the blood pump. The insert has an inner perimeter, an outer perimeter, and a plurality of extensions that extend radially inward between the outer perimeter and the inner perimeter. The insert is formed of a resilient material. The insert is formed of a nickel-titanium alloy. The sewing ring has a flexural modulus of greater than 50 psi. The sewing ring has a flexural modulus of at least 60 psi. The sewing ring has a flexural modulus of at least 75 psi. The sewing ring has a flexural modulus of at least 100 psi. The sewing ring has a flexural modulus of at least 125 psi. The sewing ring has a flexural modulus of at least 150 psi. The sewing ring has a flexural modulus of less than 1500 psi. The sewing ring has a flexural modulus of less than 1000 psi. The sewing ring has a flexural modulus of less than 750 psi.

In another general aspect, a method includes attaching a cuff to a heart, the cuff being sufficiently rigid such that at least a portion of a myocardium of the heart is flattened by the attaching. The method also includes forming an opening in the myocardium, positioning an inflow cannula of a blood pump through a central opening in the cuff and into the opening in the myocardium, and attaching the blood pump to the cuff.

Implementations may include one or more of the following features. For example, the method includes attaching one or more sutures to one or more suture anchors disposed on an exterior of the blood pump. Attaching the one or more sutures to one or more suture anchors includes passing a suture through an eyelet disposed along an outer perimeter of the blood pump and through a portion of the cuff. Attaching the one or more sutures to one or more suture anchors includes passing a suture through an eyelet disposed along an outer perimeter of the blood pump and through a portion of the myocardium. Attaching the one or more sutures to one or more suture anchors includes attaching sutures at multiple suture anchors disposed around an outer perimeter of the blood pump, the sutures extending through a sewing ring of the cuff and maintaining the position of the sewing ring generally along a plane perpendicular to the inflow cannula. Attaching the blood pump to the cuff includes engaging a coupling mechanism configured to prevent translation of the inflow cannula through the central opening of the cuff. Engaging the coupling mechanism includes holding the cuff at an outer edge of the cuff and applying a counterforce with the cuff against the blood pump. Attaching the blood pump to the cuff includes engaging a locking mechanism after engaging the coupling mechanism. Forming the opening in the myocardium includes cutting the opening in the myocardium through the cuff after the cuff is attached to the heart. Attaching the cuff to the heart includes attaching the cuff to the heart after forming the opening in the myocardium, the central opening of the cuff being positioned over the opening in the myocardium. Attaching the cuff to the heart includes attaching to the heart a cuff that includes a sewing ring that includes two or more layers of fabric. Attaching the cuff to the heart includes attaching to the heart a cuff that includes a generally planar insert disposed between two or more layers of fabric, the generally planar insert being more rigid than the two or more layers of fabric. The method includes surrounding the blood pump within an implantable fabric cover defining a pocket around the blood pump. The forming is performed before the attaching. The forming and the positioning of the inflow cannula are performed substantially in one step.

In another general aspect, a method includes: attaching a cuff to a heart, the cuff having a central opening; forming an opening in the heart; positioning an inflow cannula of a blood pump through the central opening in the cuff and into the opening in the heart; and attaching the blood pump to the cuff with a suture anchored to a suture anchor on the exterior of the blood pump.

In another general aspect, a method includes: attaching a cuff to a heart, the cuff having a central opening; forming an opening in the heart; positioning an inflow cannula of a blood pump through the central opening in the cuff and into the opening in the heart; attaching the blood pump to the cuff; and enclosing the implanted blood pump within an implantable fabric cover.

In another general aspect, a system includes a blood pump having an inflow cannula defining a lumen and a central axis and a cuff for attachment to a heart. The cuff includes a fabric disc defining a central opening. The cuff or the inflow cannula includes a portion extending radially outward from the central axis. The portion is configured to contact an endocardium of the heart when the blood pump is implanted with the inflow cannula extending into the heart through the central opening of the cuff.

Implementations may include one or more of the following features. For example, the inflow cannula includes a proximal end that flares outward. The cuff includes a flexible portion that is configured to deflect inward to enter a hole in the heart, and is configured to expand outward within the heart to rest against the endocardium. The cuff has a proximal portion and a distal portion that each extend radially outward from the central axis, and a distance between the proximal portion and the distal portion is adjustable to capture a portion of a myocardium of the heart between the proximal portion and the distal portion. The cuff includes a proximal portion and a distal portion and a length between the proximal portion and distal portion, wherein the length is adjustable. The cuff includes a member configured to exert a force on heart tissue located between the proximal portion and the distal portion. The cuff includes a frame that is resilient or has a shape memory. The frame is configured to expand a proximal portion of the cuff radially outward from the central axis within the heart to capture a portion of the heart located about the cuff. The frame is configured to contract along the central axis when deployed in a hole in the heart.

In another general aspect, a cuff for attachment to a heart defines an opening to admit a cannula of a heart pump. A coupling mechanism couples the cuff about the cannula, and a locking mechanism secures the position of the cuff set by the coupling mechanism.

In another general aspect, an implantable system includes a cuff, a surface defining channels, and a clip having arms that extend into the channels. The arms travel along the channels during movement of the clip between an unlocked position of the clip and a locked position of the clip. The clip permits the cuff to be coupled about a cannula when the clip is in the unlocked position, and the clip is configured to secure the cuff relative to the cannula when the clip is in the locked position.

Implementations can include one or more of the following features. For example, the implantable system includes a cover, and the clip is captured between the cover and the surface. The cannula has a longitudinal axis, and the clip moves between the unlocked position and the locked position in a plane perpendicular to the longitudinal axis. The cover and the surface define a slot, and the clip travels along a linear direction through the slot to enter the locked position. The channels define detents, and when the cuff is not coupled to the cannula, movement of the clip from the unlocked position toward the locked position engages the arms into the detents to impede the clip from entering the locked position. Each of the arms can engage a detent independent of whether another arm engages a detent, and engagement of any of the arms with a detent impedes the clip from entering the locked position. When the clip moves toward the locked position and the cuff is coupled about the cannula, the arms engage the cuff to avoid the detents. The arms include teeth configured to limit rotation of the cuff about the cannula when the clip is in the locked position. A sealing ring is disposed about the cannula, and the sealing ring is engageable to an inner surface of the cuff to couple the cuff to the cannula. The clip includes a visual indicator disposed such that the visual indicator is exposed when the clip is not in the locked position and the visual indicator is obscured when the clip is in the locked position. The clip includes a latch that impedes the clip from exiting the locked position.

In another general aspect, an implant includes a cuff defining an opening configured to receive a cannula coupled to a heart pump and a coupling mechanism having a first position and a second position. The cuff is uncoupled from the cannula in the first position and the coupling mechanism couples the cuff to the cannula in the second position. The implant includes a locking mechanism configured to secure the coupling mechanism in the second position, and the locking mechanism is configured to be moved to a locked position after the coupling mechanism is in the second position.

Implementations can include one or more of the following features. For example, a first action positions the coupling mechanism in the second position, and a second action activates the locking mechanism to secure the coupling mechanism in the second position, and the second action occurs subsequent to and separate from the first action. The cannula includes a flange and a circumferential ridge, and the coupling mechanism is configured to capture the cuff about the cannula between the flange and the circumferential ridge. The cannula includes (i) an attachment portion between the flange and the circumferential ridge and (ii) an inflow portion, and the attachment portion has an outer diameter greater than an outer diameter of the inflow portion. The cuff includes an inner portion, an outer portion, and a member each disposed concentrically about the opening, the member being disposed between the inner portion and the outer portion, and the outer portion extending in a direction generally perpendicular to the member. The coupling mechanism includes a clamp coupled to the cuff and disposed about the opening.

Implementations can include one or more of the following features. The clamp has a first end and a second end, the clamp configured such that bringing the first end near the second end opens the clamp and moving the two ends apart closes the clamp. The locking mechanism includes a cam that defines a channel, the cam being coupled to the first end of the clamp and being configured to rotate about the first end, the second end of the clamp being disposed in the channel and being configured to travel within the channel. The channel includes a curved portion, the curved portion being configured to limit the motion of the second end of the clamp in the channel when the clamp is closed. The coupling mechanism includes an attachment member coupled about the opening of the cuff, the attachment member having one or more flanged portions that extend outward from the opening, and the locking mechanism includes a clip configured engage the flanged portions to limit movement of the cuff relative to the cannula. The clip is configured to enter a slot in the pump to secure the cuff to the pump. The attachment member includes one or more extensions each including a contact portion that extends toward the opening, the cannula includes a tapered circumferential ridge, and the second position of the coupling mechanism, the contact portions are disposed between the pump and the circumferential ridge along the length of the cannula.

In another general aspect, a cuff for attachment to a heart includes a member defining an opening, a seal coupled to the member and disposed about the opening, and a clamp coupled to the seal and disposed about the opening. The clamp has a first end and a second end, and the clamp is configured such that (i) bringing the first end near the second end opens the clamp and (ii) moving the first end and the second end apart closes the clamp.

Implementations can include one or more of the following features. For example, a cam defining a channel, the cam being coupled to the first end of the clamp and being configured to rotate about the first end, the second end of the clamp being disposed in the channel and being configured to travel within the channel.

In another general aspect, a cuff for attachment to a heart includes a member defining an opening, a linking member coupled to the member and disposed about the opening, and an attachment member coupled to the linking member and disposed about the opening. The linking member extends about an outer surface of the attachment member. The attachment member is configured to attach the cuff to a cannula disposed through the opening. The attachment member has at least one flanged portion extending outward from the opening in a plane generally perpendicular to a circular portion of the attachment member.

Implementations can include one or more of the following features. For example, the linking member is molded over a portion of the attachment member, and the attachment member is coupled to the member through the linking member. The attachment member includes at least one extension disposed generally perpendicular to the member, the extension having a tapered portion disposed on a surface of the extension facing toward the opening. The attachment member defines circumferential groove configured to admit a sealing ring. The linking member includes an elastomer. The linking member is configured to form a seal.

In another general aspect, a method of attaching a ventricular assist device to a patient, includes: attaching a cuff to a heart, the cuff defining an opening; removing tissue of the heart through the opening of the cuff; inserting a cannula through the opening of the cuff; engaging a coupling mechanism to set a position of the cuff relative to the cannula; and engaging a locking mechanism to secure the position of the cuff relative to the cannula.

Implementations can include one or more of the following features. For example, selecting a location near the apex of the heart to attach the cuff. Engaging a cardiac bypass system so that blood is not circulating through the heart. Engaging the coupling mechanism includes inserting a tapered portion of the cannula into the cuff so that one or more extensions of the cuff engage a groove defined adjacent to the tapered portion. Engaging the locking mechanism includes inserting a clip that engages the cuff and a pump coupled to the cannula. Engaging the coupling mechanism includes closing a clamp coupled to the cuff so that the clamp engages a groove defined in the cannula. Engaging the locking mechanism includes capturing an end of a clamp to secure the clamp in a locked position. Engaging the coupling mechanism to set a position of the cuff relative to the cannula includes positioning the cuff such that an inner surface of the cuff engages a sealing ring disposed about the cannula and a bottom surface of the cuff engages a surface of the cannula or a surface of a pump that is coupled to the cannula. Engaging the locking mechanism includes moving a clip in a plane perpendicular to the cannula. Engaging the locking mechanism includes moving a clip into a locked position about the cuff, the clip limiting travel of the cannula out of the cuff. Engaging the locking mechanism includes engaging a latch that secures the clip in the locked position.

In another general aspect, a system includes a cuff having an annular member defining an opening and an attachment member disposed about the opening. The attachment member includes a flanged portion oriented generally parallel to the annular member, and the flanged portion extends outward from the opening. A clip is configured to be coupled about the attachment member between the annular member and the flanged portion.

Implementations can include one or more of the following features. For example, the system includes a pump assembly that includes a cannula, and the clip is configured to travel relative to the pump assembly from an unlocked position to a locked position in which the clip secures the cuff about the cannula. The clip is configured to travel along a substantially linear path from the unlocked position to the locked position. When the cuff is coupled to the pump assembly and the clip is in the locked position, the clip impedes rotation of the cuff about the cannula. The cuff includes ridges disposed on the attachment member, and the clip is configured to engage the ridges to impede rotation of the cuff. The clip is configured to engage the pump assembly such that the travel of clip to the locked position is impeded when the cuff is improperly seated about the cannula. The clip is configured to engage the pump assembly such that travel of clip to the locked position is impeded when the cuff is not coupled to the pump assembly. The system includes a visual indicator that is visible when the clip is not in the locked position and is obscured when the clip is in the locked position. When the clip is in the locked position, engagement of the clip and the pump assembly impedes travel of the clip out of the locked position. The clip has arms that are configured to extend about the cuff in the locked position, the arms being configured such that any of the arms can engage the pump assembly to impede travel of the clip into the locking position.

In another general aspect, a system includes a cuff having a member defining an opening and an attachment member disposed about the opening. The attachment member includes (i) a clamp having a first end and a second end, and (ii) a cam defining a channel. The cam is coupled to the first end of the clamp and is configured to rotate about the first end. The second end of the clamp is disposed in the channel and is configured to travel within the channel.

The features described can be used in any appropriate combination and subcombination, including combinations across multiple aspects described above. Features described with respect to one aspect can additionally or alternatively be included in implementations of any of the other aspects. The details of one or more implementations are set forth in the accompanying drawings and the description below. Other features, objects, and advantages will be apparent from the description and drawings, and from the claims.

DESCRIPTION OF DRAWINGS

FIG. 5A is a perspective view of a cam of the ventricular cuff.
FIGS. 5B to 5E are respectively top, bottom, lateral side, and opposite lateral side views of the ventricular cuff.
FIGS. 8A to 8D and 9A to 9C are perspective views illustrating the coupling of the ventricular cuff to the pump.

FIG. 41 is a cross-sectional view of an assembly of a cuff and an inflow cannula.

FIGS. 42A and 42B are cross-sectional views of another assembly of a cuff and an inflow cannula.

DETAILED DESCRIPTION

Figure 1:
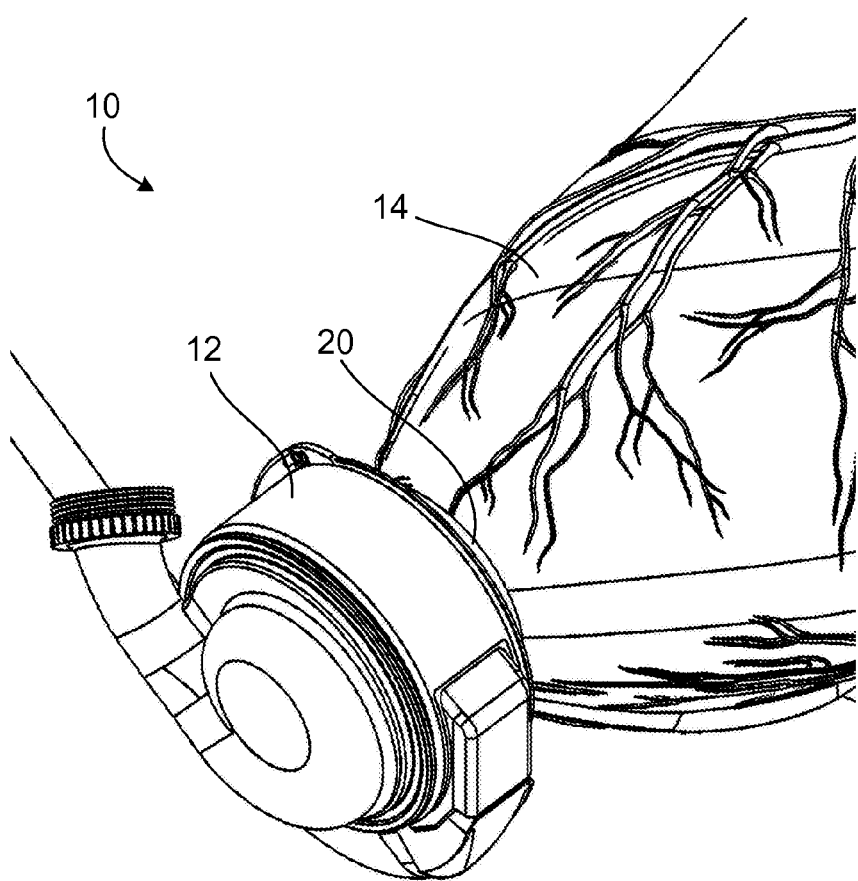
FIG. 1 is a perspective view of a pump installed at a heart.

Referring to FIG. 1, a ventricular assist system 10 for treating, for example, a patient with a weakened left ventricle, includes a blood pump 12 that receives blood from a patient's heart 14. The pump 12 is coupled to a cuff 20, which in turn is attached to the heart 14. The cuff 20 is attached to the heart by, for example, sutures that attach a portion of the cuff 20 to the apex of the left ventricle of the heart 14. The pump 12 receives blood from the heart through an inflow cannula 50 (FIG. 2B) of the pump 12 disposed through an opening in the cuff 20.

Figure 2A:
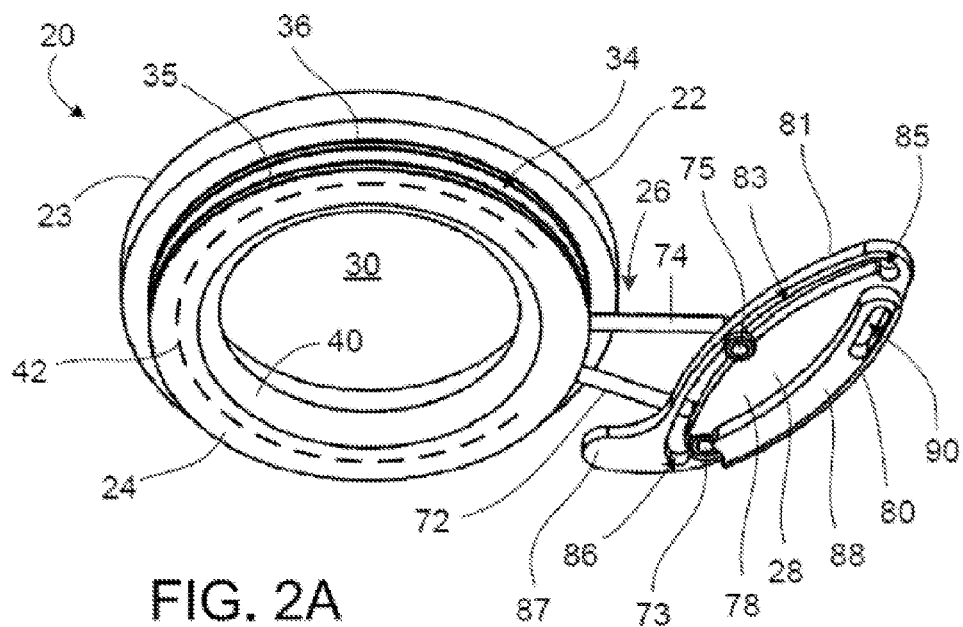
FIG. 2A is a perspective view of a ventricular cuff.
Figure 2B:
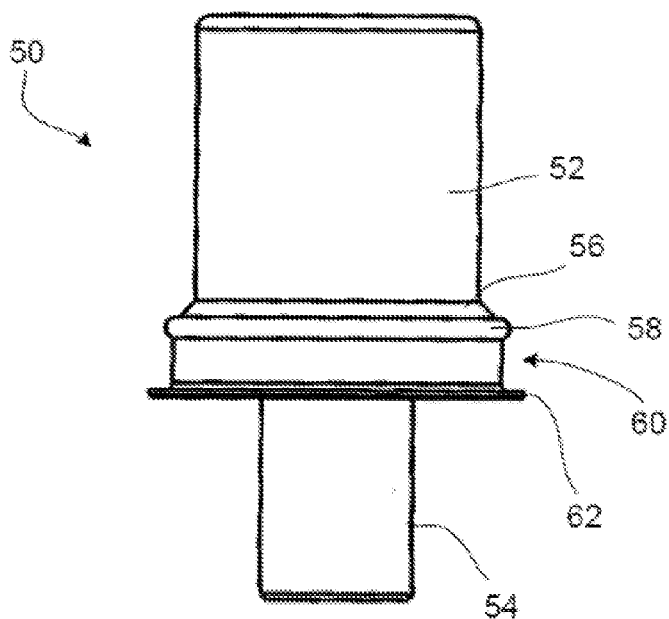
FIG. 2B is a side view of a cannula for coupling to the ventricular cuff.

Referring to FIGS. 2A and 2B, the cuff 20 defines an opening 30 that admits the inflow cannula 50. The cuff 20 includes a coupling mechanism, for example, a clamp 26 that couples the cuff 20 to the cannula 50. The cuff 20 also includes a locking mechanism in the form of a cam 28 that secures the clamp 26 in a closed position. The locking mechanism, by maintaining the position of the coupling mechanism, limits the possibility of the cuff 20 accidentally becoming uncoupled from the cannula 50. The locking mechanism can secure the cuff 20 to the cannula 50 such that, for example, removal of the cuff 20 from the cannula 50 requires more than one action, or the cannula 50 is no longer free to rotate or translate with respect to the cannula 50 without significant outside influence, such as by a clinician.

Figure 3:
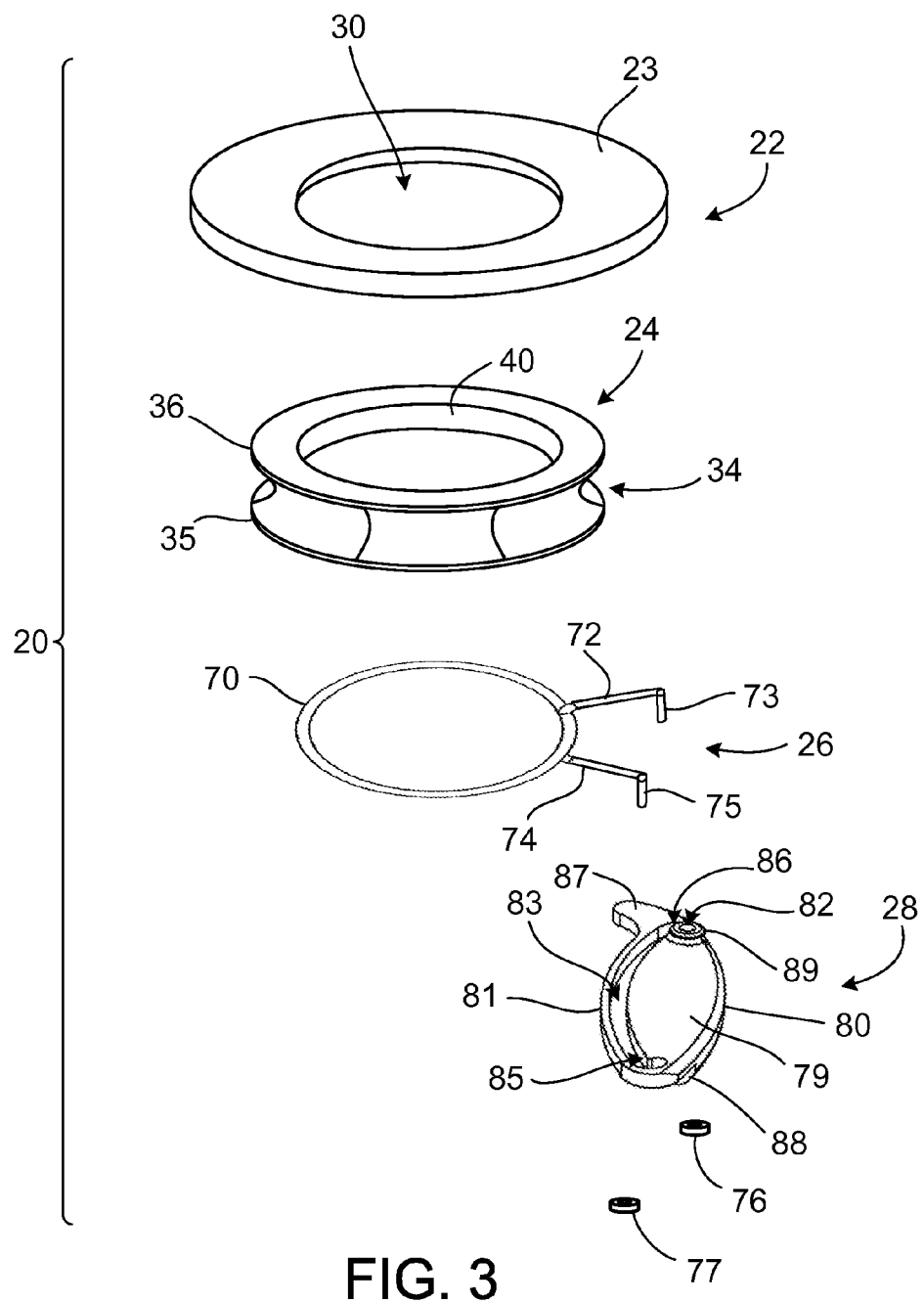
FIG. 3 is an exploded view of the ventricular cuff.

Referring to FIG. 3, the cuff 20 is illustrated in a view illustrating individual disassembled parts, including a fastening member 22, a linking member 24, the clamp 26, and the cam 28. The components illustrated can be preassembled and delivered to a clinician as a single unit. The fastening member 22 is generally ring-shaped and includes a contact surface 23 to contact heart tissue. The fastening member 22 is composed of a material through which sutures can be placed, for example a fabric such as polytetrafluoroethylene (PTFE) felt. In an implanted state, sutures or staples bind the fastening member 22 to heart tissue to couple the cuff 20 to the heart 14. In one embodiment, the fastening member 22 and the linking member 24 are pre-assembled together as one unit.

Figure 4A:
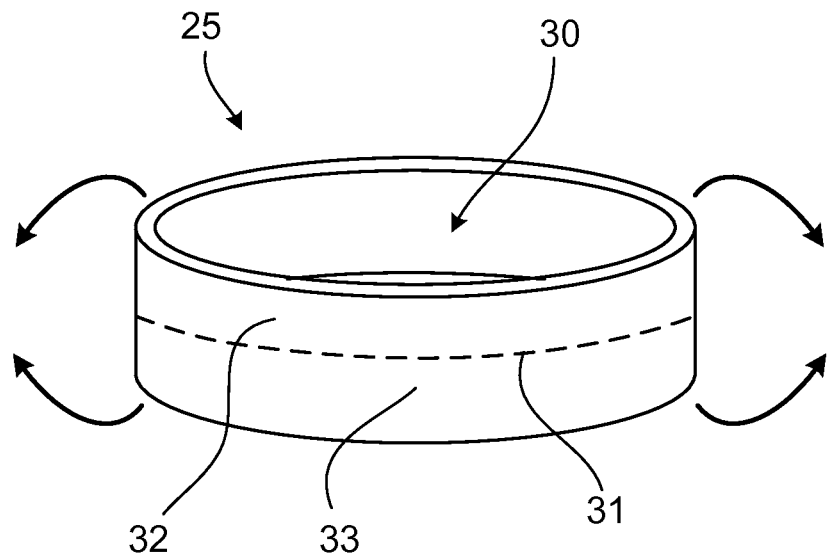
FIG. 4A is a perspective view of a tube from which a seal member of the ventricular cuff can be fabricated.
Figure 4B:
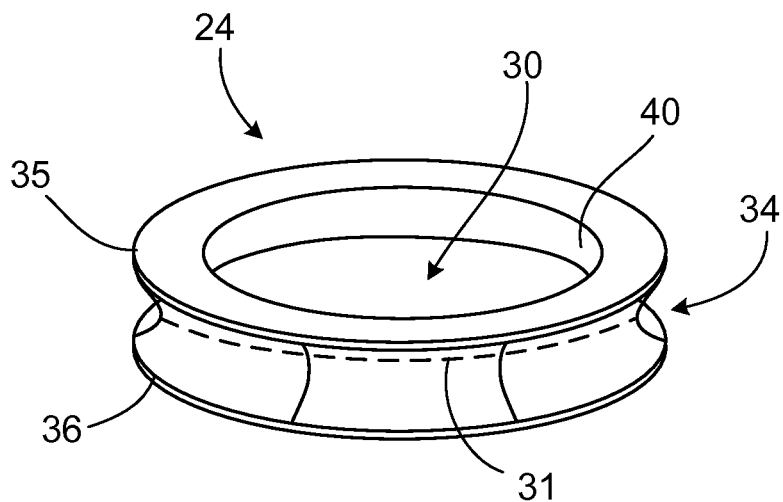
FIG. 4B is a perspective view of a seal member of the ventricular cuff.

Referring to FIGS. 4A and 4B, the linking member 24 can be fabricated by reshaping a tube 25 formed of, for example, an elastomer such as silicone. The linking member 24 is formed, for example, by folding an upper portion 32 of the tube 25 and a lower portion 33 of the tube 25 about an outer circumference 31 of the tube 25. The resulting linking member 24 defines a circumferential groove 34 between generally parallel ring-shaped portions 35, 36. The linking member 24 also includes a circumferential inner surface 40 that forms a seal with the cannula 50.

The linking member 24 can also be fabricated to include ring-shaped reinforcement members 37, 38 (FIG. 6) that includes, for example, a mesh material or a knitted fabric formed of a material such as polyester. A knitted fabric or mesh material is embedded into a silicone sheet. The silicone sheet is die-cut into ring-shaped portions 35, 36 that respectively include the ring-shaped reinforcement members 38, 37. The ring-shaped portions 35, 36 are then placed in a silicone mold and overmolded with additional silicone. The molded silicone binds the ring-shaped portions 35, 36 together and creates a flexible connection between the ring-shaped portions 35, 36, which include the reinforcement members 38, 37.

Referring to FIG. 2A and FIG. 3, the clamp 26 includes a circular portion 70 formed of a resilient material, such as metal wire. For example, the circular portion 70 can be formed of stainless steel or a cobalt chromium alloy, each of which can provide implantability, long term stability, and resiliency. In the assembled cuff 20, the circular portion 70 is disposed in the circumferential groove 34 of the linking member 24. The linking member 24 is thus couples the clamp 26 to the fastening member 22. Sutures 42 pass through the fastening member 22 and the ring-shaped portions 35, 36 of the linking member 24, capturing the circular portion 70 in the linking member 24 and coupling the linking member 24 to the fastening member 22. The reinforcement members 37, 38 limit tearing of the linking member 24 by the sutures 42. In addition to, or instead of, sutures 42, the linking member 24 can be coupled to the fastening member 22 by an adhesive or by overmolding the linking member 24 over a portion of the fastening member 22.

The clamp 26 has a relaxed position toward which it wants to return after a load is applied to open or close the clamp 26. The circular portion 70 is expanded by moving the arms 72, 74 closer together. The circular portion 70 is contracted by increasing the distance between the arms 72, 74. Expansion of the circular portion 70 beyond the relaxed position loads the circular portion 70, causing the circular portion 70 to exert a force that tends to contract the circular portion 70 (e.g., an inward radial force). Conversely, compression of the circular portion 70 beyond the relaxed position loads the circular portion 70 such that the circular portion 70 exerts a force to expand the circular portion 70 (e.g., an outward radial force).

The clamp 26 includes a pivot arm 72 and a travelling arm 74 that extend from the circular portion 70. The pivot arm 72 and the travelling arm 74 provide leverage to expand and contract the circular portion 70, thus opening and closing the clamp 26. The pivot arm 72 includes a pivot end 73, and the travelling arm 74 includes a travelling end 75. The ends 73, 75 extend generally perpendicular to their respective arms 72, 74. The ends 73, 75 each pass through the cam 28 and are captured in the cam 28 by a cap 76, 77.

Referring to FIGS. 5A to 5E, the cam 28 includes a top side 78, a bottom side 79, and opposite lateral sides 80, 81. The cam 28 can be formed of, for example, polyether ether ketone (PEEK) or stainless steel. The cam 28 defines a pivot hole 82 that admits the pivot end 73, and defines a channel 83 that admits the travelling end 75. About the pivot hole 82, in the top side 78, the cam 28 defines a recess 84 that receives the cap 76. Opposite the recess 84, the cam 28 includes a boss 89 that extends from the bottom side 79. The height, H, of the boss 89 maintains a space between the pivot arm 72 and the bottom side 79. By contrast, the travelling arm 74 can contact the bottom side 79. The two arms 72, 74 travel in different planes separated by the distance H. Because the boss 89 maintains the pivot arm 72 at a distance from the bottom side 79, the travelling arm 74 can move relative to the pivot arm 72 without contacting the pivot arm 72. The cap 77 is disposed adjacent to the top side 78 and the cap 76 is disposed in the recess 84 such that the caps 76, 77 do not contact each other during operation of the clamp 26.

The channel 83 defines a path, such as a curve, between a detent 85 and an end 86 located near the pivot hole 82. The detent 85 includes a hooked portion of the channel 83 that captures the travelling end 75 to secure the clamp 26 in the closed position.

The cam 28 includes an extension 87 that indicates proper placement of the cuff 20 relative to the pump 12. As the cuff 20 becomes coupled to the cannula 50, the extension 87 engages the surface 13 of the pump 12 to indicate proper placement of the cuff 20 relative to the pump 12. In addition, the extension 87 aligns the cam 28 in a plane generally parallel to the surface 13. Alignment of the cam 28 with respect to the surface 13 reduces the likelihood that the cam 28 may engage a portion of the pump 12 and improperly impede the clamp 26 from closing completely. The cam 28 also includes a raised portion 88 extending from the top side 78, which facilitates manipulation of the cam 28. The raised portion 88 is rounded to rest against the outer circumference of the pump 12 when the cam 28 is locked (see FIG. 9C). The raised portion 88 defines a slot 90 in which a tool or surgical instrument can be inserted to unlock the cam 28. The slot 90 can be used to pry open the clamp 26, for example, if tissue ingrowth makes manual manipulation of the cam 28 difficult.

Manipulation of the cam 28 moves the clamp 26 between open and closed positions. In the open position, the clamp 26 permits a proximal portion 52 of the cannula 50 to pass through the opening 30. In the closed position, the clamp 26 presses inward to couple the cuff 20 to the cannula 50. In the closed position, the clamp 26 presses the linking member 24 into engagement with the cannula 50, and the circumferential inner surface 40 of the linking member 24 forms a seal with the cannula 50.

Referring to FIG. 2B, the cannula 50 is shown by itself here but is generally an integrated component of the pump 12. In some implementations, the pump 12 can receive different interchangeable cannulas to achieve an appropriate fit in a particular anatomy. The cannula 50 includes the proximal portion 52 that passes through the opening 30 into the heart 14 and a distal portion 54 housed within the pump 12. Along the length of the cannula 50, between the proximal portion 52 and the distal portion 54, the cannula 50 includes a circumferential tapered portion 56, a circumferential ridge 58, and a circumferential flange 62. The cannula 50 defines a circumferential groove 60 in which the clamp 26 and the linking member 24 are received.

To couple the cannula 50 to the cuff 20, the proximal portion 52 is passed through the opening 30, such that the circumferential tapered portion 56 engages the circumferential inner surface 40 of the linking member 24, guiding the cannula 50 into alignment with the cuff 20. Further advancement of the cannula 50 causes the circumferential ridge 58 to travel past the circular portion 70 of the clamp 26. The action of the circumferential ridge 58 passing the circular portion 70 provides a clinician tactile feedback about the proper location of the components. The circumferential flange 62 limits further travel of the cannula 50 relative to the cuff 20, positioning the circular portion 70 of the clamp 26 about the circumferential groove 60. The fastening member 22 is disposed about the cannula 50, generally about the circumferential ridge 58.

The cuff 20 is sized so that the inner diameter of the cuff 20 is greater than the outer diameter of the proximal portion 52, which facilitates insertion of the proximal portion 52. With the clamp 26 in its open position, the size of the inner diameter of the cuff 20 approximates that of the outer diameter of the circumferential ridge 58. The circumferential ridge 58 is rounded, permitting the linking member 24 to slide over the circumferential ridge 58 and into the circumferential groove 60. Thus a clinician can determine that the cuff 20 is properly positioned relative to the cannula 50 by experiencing the tactile sensation of the linking member 24 entering the circumferential groove 60.

Figure 6:
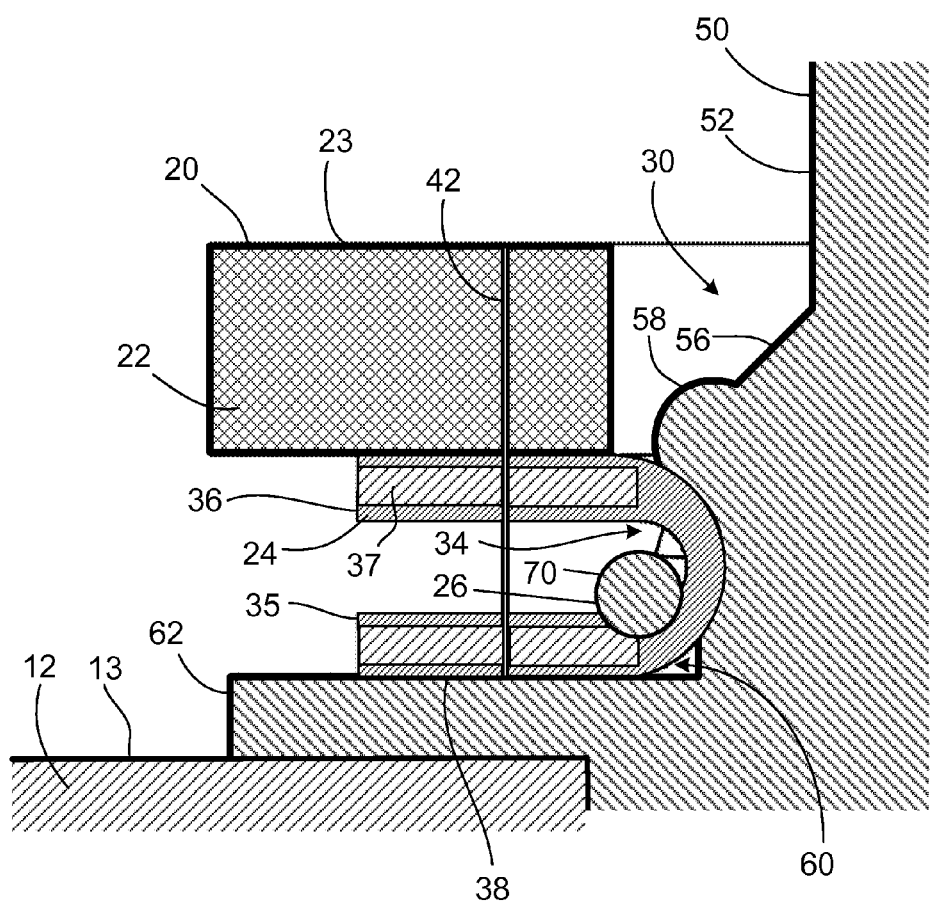
FIG. 6 is a side cross-sectional view of the ventricular cuff coupled to the cannula across line 6-6 of FIG. 8D.

Referring to FIG. 6, the cuff 20 is coupled to the cannula 50 by moving the clamp 26 to its closed position. In the closed position, the inner diameter of the clamp 26 is smaller than the outer diameter of the circumferential ridge 58. The clamp 26 presses the linking member 24 into the circumferential groove 60, forming a seal and capturing the cannula 50 in the cuff 20. The outer diameter of the cannula 50 at the circumferential groove 60 is larger than the outer diameter of the proximal portion 52. The differential in diameter allows passage of a coring tool through the cuff 20. In some instances, the coring tool can be slightly larger than the proximal portion 52 of the cannula 50. In addition, the differential in diameter can allow the clinician to further confirm proper placement of the cuff 20 relative to the cannula 50. A clinician can confirm proper placement by applying a small axial load that would tend to separate the cannula 50 from the cuff 20. If the cannula 50 and the cuff 20 separate easily, then the cuff 20 is improperly seated. If cannula 50 and the cuff 20 remain coupled, however, the cuff 20 is properly seated.

Figure 7A:
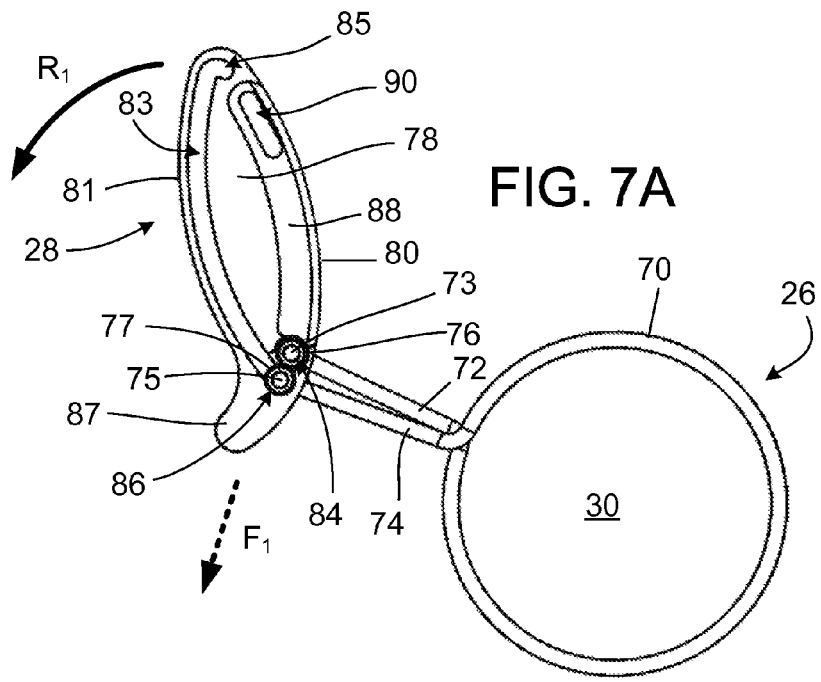
FIGS. 7A to 7D are top views illustrating the closing of a clamp of the ventricular cuff.
Figure 7B:
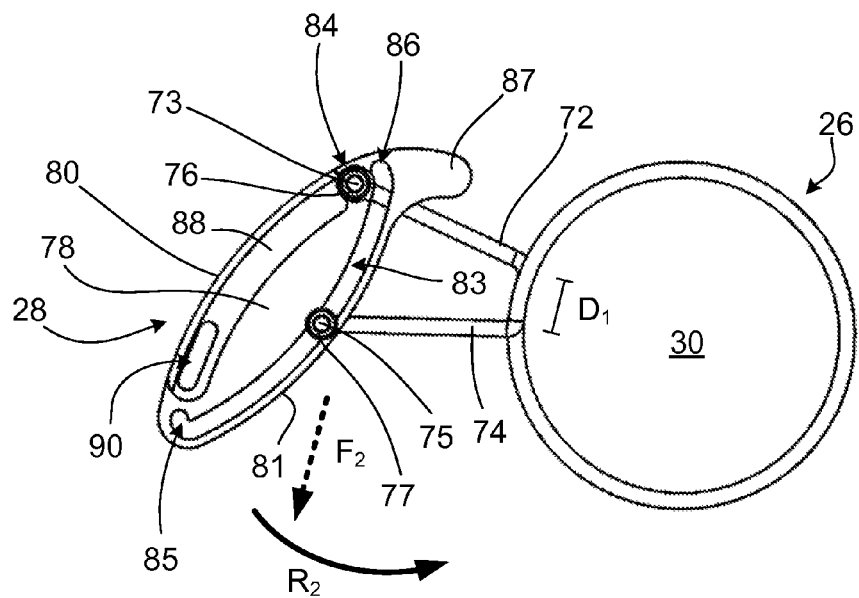
Figure 7C:
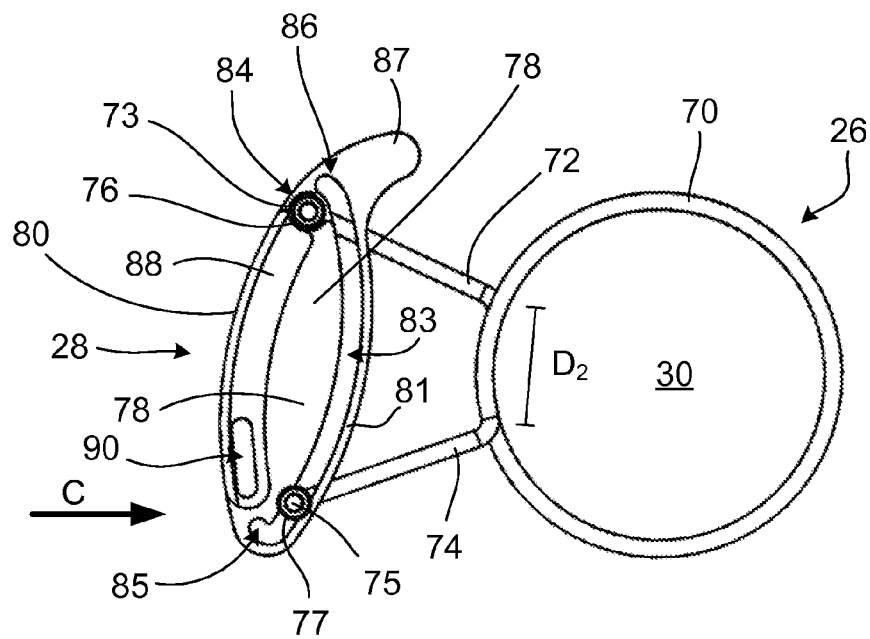

Referring to FIG. 7A, as the clamp 26 moves from the open position of FIG. 7A to the closed position of FIG. 7C, the cam 28 rotates about the pivot end 73 in a plane. As the cam 28 rotates, the travelling end 75 travels through the channel 83. In the open position, the pivot arm 72 and the travelling arm 74 are located near each other, and the circular portion 70 is expanded beyond its relaxed position. In this position, the clamp 26 can admit the circumferential ridge 58 of the cannula 50 through the opening 30. The travelling end 75 is located at the end 86 of the channel 83 nearest the pivot end 73.

Because the circular portion 70 is loaded, the circular portion 70 exerts a force on the end 75 in the direction of arrow $F_1$ to separate the pivot arm 72 and the travelling arm 74. Nevertheless, the open position is stable because the force acts away from the length of the channel 83 and instead presses the travelling end 75 into the end 86 of the channel 83. As a result, the open position can be maintained while the cannula 50 is placed relative to the clamp 26.

From the open position, a clinician closes the clamp 26 by exerting a force on the side 80 of the cam 28, causing the cam 28 to rotate in a plane about the pivot end 73. A small rotation of the cam 28 in the direction of arrow $R_1$ brings the length of the channel 83 into closer alignment with the direction of force, $F_1$, exerted by the circular portion 70 on the travelling end 75. The force exerted by the circular portion 70 continues the rotation of the cam 28 about the pivot end 73 as the clamp 26 continues to close.

Referring to FIG. 7B, the clamp 26 is in an unstable position between the open position and the closed position. Force exerted by the loaded circular portion 70 continues to rotate the cam 28 in the plane and close the clamp 26. The distance between the pivot arm 72 and the travelling arm 74 increases, and the circular portion 70 contracts, resulting in an overlap of the circular portion 70 of a distance, $D_1$. The clinician is not required to apply additional force on the cam 28 to move the clamp 26 to the closed position. The clamp 26 exerts a force in the direction of arrow $F_2$, moving the end 75 through the channel 83. As the travelling end 75 proceeds through the channel 83, the cam 28 continues to rotate about the pivot end 73, as indicated by arrow $R_2$.

Referring to FIG. 7C, with the clamp 26 in the closed position, the cannula 50 is captured within the clamp 26. The size of the circular portion 70 in the closed position can be selected to permit rotation of the cannula 50 relative to the cuff 20 or to limit such rotation.

The closed position is stable. The circular portion 70 is in its unloaded, relaxed position. As a result, the clamp 26 does not exert a force on the travelling end 75 in either direction along the channel 83. The travelling end 75 is located in the channel 83 near the detent 85 but not in the detent 85.

To lock the clamp 26, the clinician applies a force to the side 80 of the cam 28, in the direction of arrow C, which rotates the cam 28 further in the plane. As the cam 28 rotates, the cam 28 exerts a force on the travelling end 75 that is generally aligned with the channel 83, causing the arms 72, 74 to separate further. Rotation of the cam 28 moves the travelling end 75 into the detent 85 and loads the circular portion 70. This action closes the circular portion 70 beyond its relaxed position, reducing the diameter of the circular portion 70 to lock the clamp 26 about the circumferential groove 60 of the cannula 50. Locking the clamp 26 also causes the circular portion 70 to exert an inward radial force to compress the linking member 24 and press the circumferential inner surface 40 into the circumferential groove 60, forming a hemostatic seal.

Figure 7D:
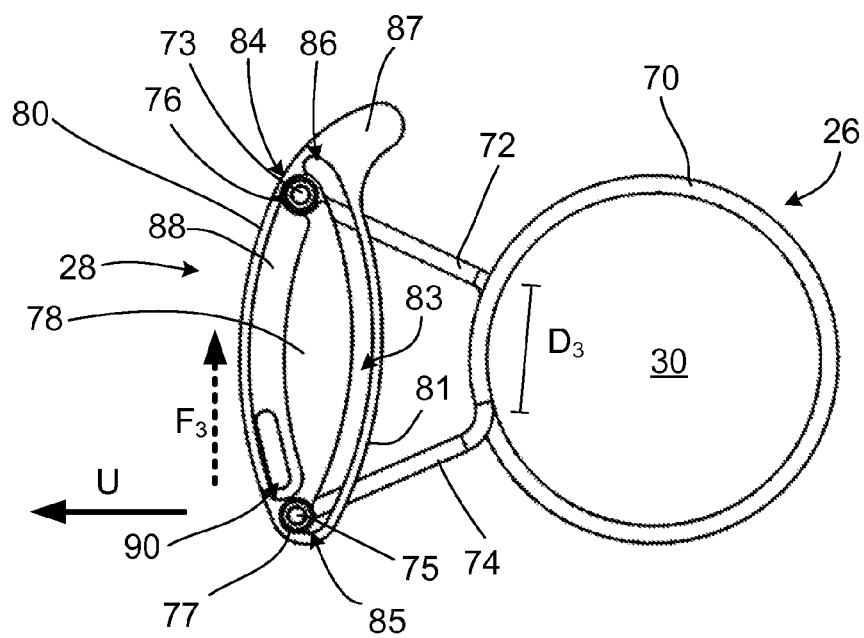

Referring to FIG. 7D, in the locked position of the clamp 26, the cam 28 impedes the clamp 26 from opening. The circular portion 70 is slightly compressed beyond its relaxed position, such that the overlap distance $D_3$ is larger than $D_2$. The loaded circular portion 70 exerts a force on the travelling end 75 in the direction of arrow $F_3$, which presses the travelling end 75 into the detent 85. Because the circular portion 70 forces the travelling end 75 into the detent 85, the travelling end 75 is impeded from traveling through the channel 83 and moving the clamp 26 into the open position.

To open the clamp 26 from the locked position, the travelling end 75 must be dislodged from the detent 85. The clinician applies a force, for example, in the direction of arrow U, to overcome the force of the loaded circular portion 70. The force rotates the cam 28 in the plane such that the travelling end 75 slides out of the detent 85.

From the closed position (FIG. 7C), the clamp 26 can be opened by exerting a force on the side 81 away from the circular portion 70, which rotates the cam 28 opposite the direction of arrows $R_1$ and $R_2$ until the open position is reached. The cannula 50 can then be removed or repositioned relative to the clamp 26 before the clamp 26 is closed again.

Figure 8A:
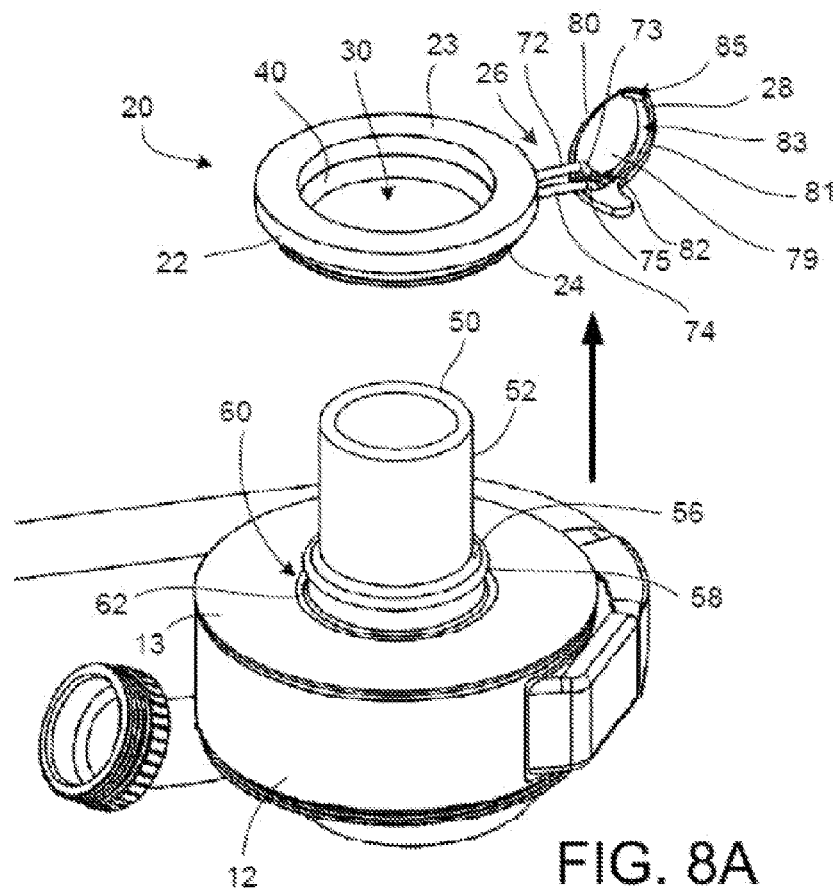

Referring to FIG. 8A, the cuff 20 is in the open position before being coupled to the cannula 50 of the pump 12. Generally, during the implantation process, the cuff 20 will first be attached to the heart 14 and then heart tissue will be removed to admit the proximal portion 52 of the cannula 50. In addition, or alternatively, heart tissue can also be removed before the cuff 20 is attached to the heart 14.

The cannula 50 is fixedly coupled to the pump 12, for example, the cannula 50 can be sealed and welded to the pump 12. Alternatively, the cannula 50 can be removably coupled to the pump 12, for example, by a threaded connection or by a mechanism that permits the cannula 50 to snap into place. A clinician can select a cannula 50 that best fits the anatomy of the patient, and can couple the cannula 50 to the pump 12 prior to or during a procedure. When the cannula 50 is coupled to the pump 12, the distal portion 54 is housed within the pump 12 and the proximal portion 52 extends from a top surface 13 of the pump 12. A clinician may select a cannula 50 that extends an appropriate distance into the heart 14. For example, a clinician may a cannula 50 with a first length for a left VAD so that the cannula 50 extends the proper distance into the heart 14. For implantation of a right VAD, however, the clinician may use a cannula with a different length so that the cannula extends a different distance into a heart.

To couple the cannula 50 to the cuff 20, the pump 12 and the cannula 50 are advanced toward the cuff 20 so that the proximal portion 52 of the cannula 50 enters the opening 30. As the cannula 50 travels relative to the cuff 20, the circumferential ridge 58 engages the circumferential inner surface 40 of the linking member 24. Further travel of the cannula 50 relative to the cuff 20 advances the circumferential ridge 58 through the linking member 24, so that the clamp 26 and the linking member 24 are disposed about the circumferential groove 60.

Advancing the circumferential ridge 58 through the linking member 24 produces tactile feedback for the clinician, such as a snap-like sensation. The tactile feedback indicates that the cuff 20 is properly seated against the circumferential flange 62 and that the circular portion 70 is disposed about the circumferential groove 60. In some implementations, as the circumferential ridge 58 engages the linking member 24 disposed over the circular portion 70, the circumferential ridge 58 slightly expands the circular portion 70. When the circumferential ridge 58 passes through the clamp 26, the clamp 26 contracts to its open position, contributing to the tactile feedback experienced by the clinician.

Figure 8B:
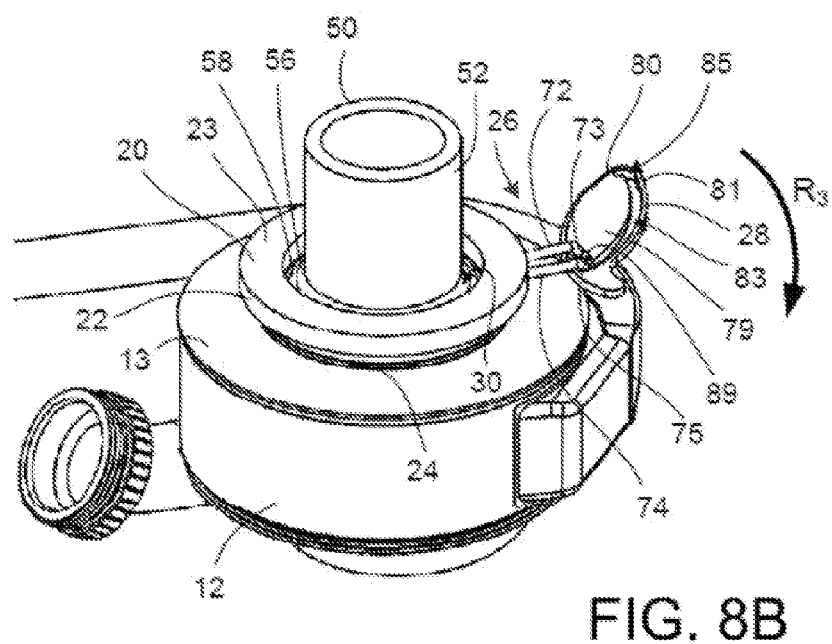

Referring to FIGS. 8B and 9A, the cuff 20 is disposed about the cannula 50, with the linking member 24 partially disposed in the circumferential groove 60. In this position, the clamp 26 can be closed to capture the cannula 50 in the cuff 20. To close the clamp 26, the clinician manipulates the cam 28 to begin rotating the cam 28 about the pivot end 73, in the direction of arrow $R_3$.

Figure 8C:
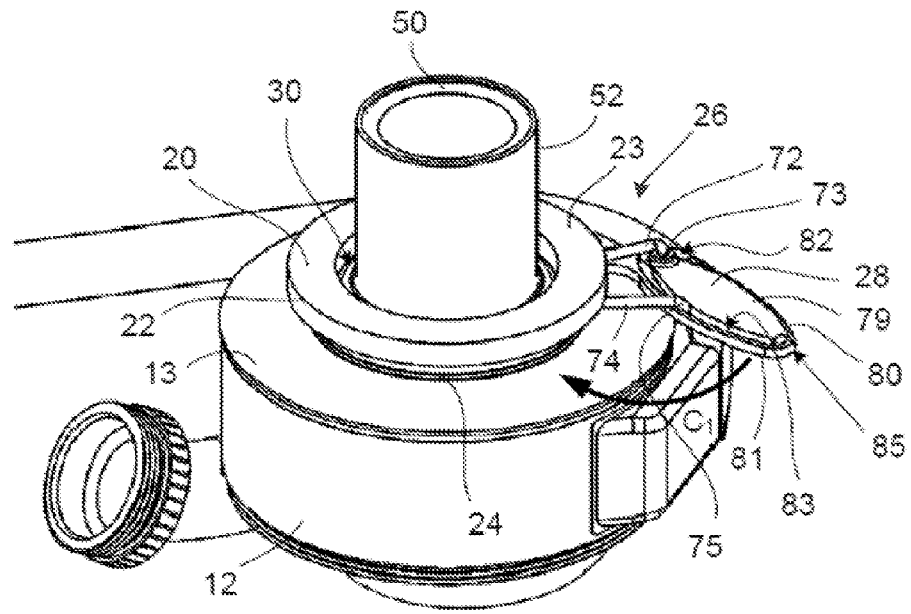

Referring to FIGS. 8C and 9B, the resilient force of the clamp 26 moves the travelling end 75 through the channel 83 defined in the cam 28, continuing the rotation of the cam 28 about the pivot end 73, in the direction of arrow $C_1$. The circular portion 70 of the clamp 26 contracts and presses the linking member 24 into the circumferential groove 60. The contraction of the circular portion 70 captures the cannula 50 within the cuff 20 because the circumferential ridge 58 cannot pass through the circular portion 70.

Figure 8D:
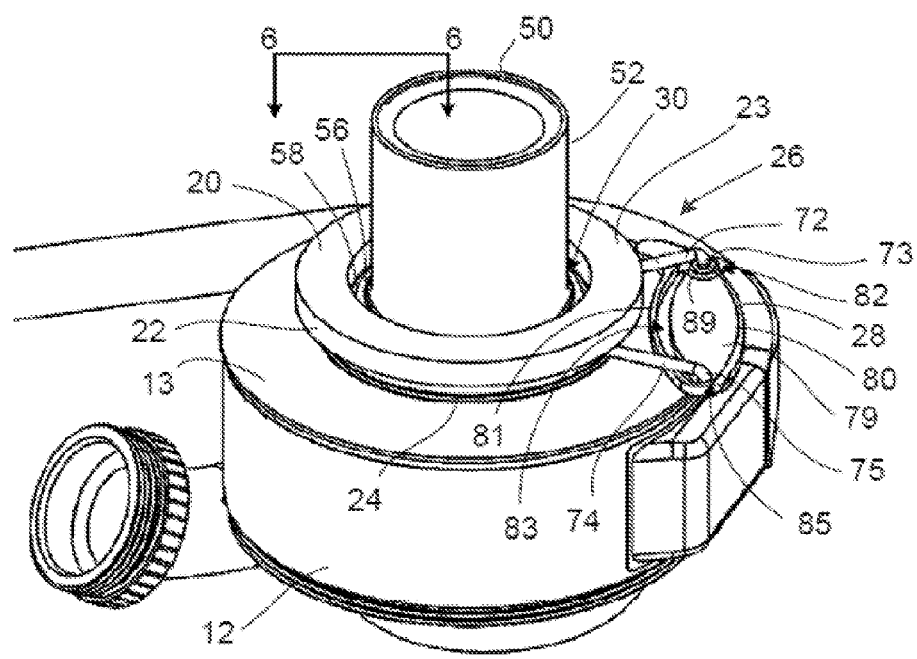

Referring to FIGS. 8D and 9C, the clamp 26 is in a closed position and the cam 28 is in a locked position, maintaining the clamp 26 in the closed position. The travelling end 75 of the clamp 26 is located in the detent 85 defined in the cam 28. From this position, the clamp 26 is unlikely to be opened accidentally, because significant force is required to remove the travelling end 75 from the detent 85. The top side 78 of the cam 28 is disposed against the top surface 13 of the pump 12, and the raised portion 88 of the cam 28 rests against the outer circumference of the pump 12.

Figure 10A:
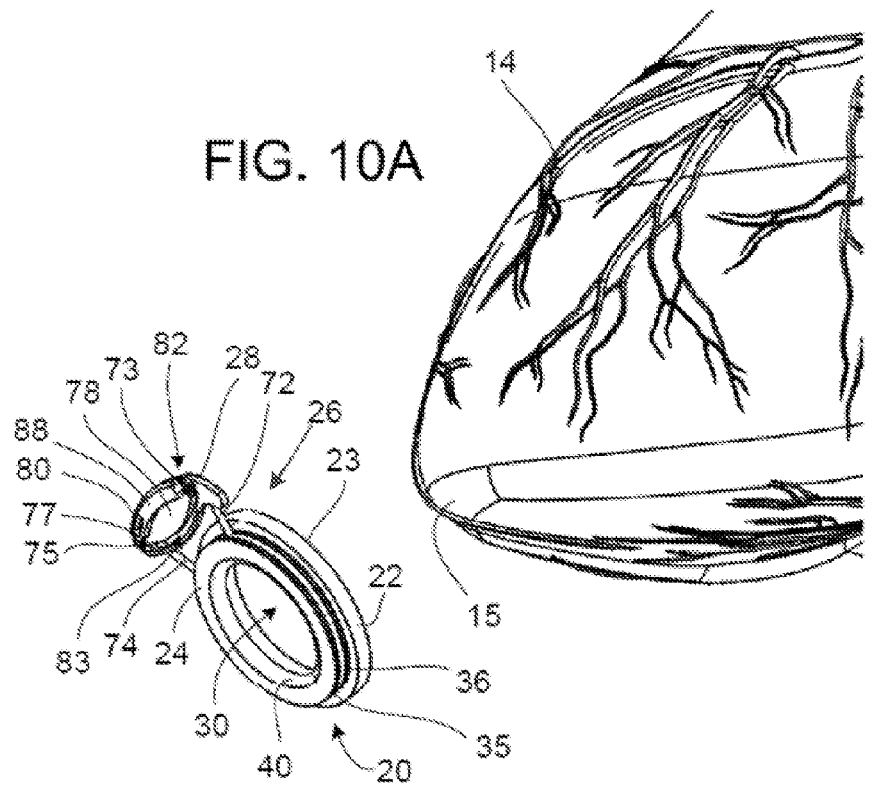
FIGS. 10A to 10D are perspective views illustrating a process for implanting the ventricular cuff and the pump.

Referring to FIG. 10A, implantation of pump 12 to the heart 14 can include selecting a location to attach the cuff 20. For example, the apex 15 of the left ventricle can be selected as an operation site.

Figure 10B:
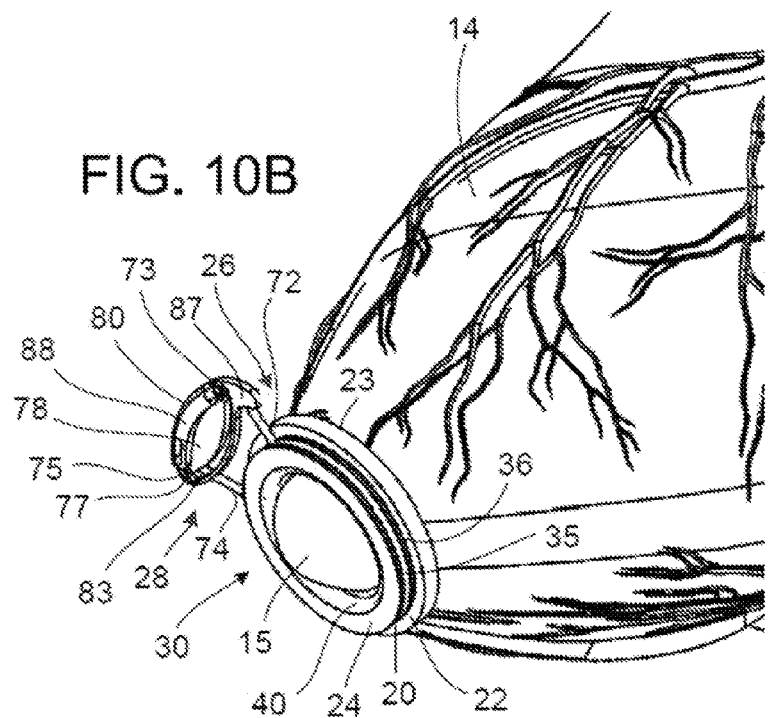

Referring to FIG. 10B, the cuff 20 is placed in contact with the heart 14 at the selected operation site. The cuff 20 is attached to the heart 14, for example, with sutures. In some embodiments, a cardiac bypass system is activated so that blood does not circulate through the heart 14. A core section of heart tissue is removed through the opening 30 of the cuff 20. Alternatively, in some embodiments, the cuff 20 can be attached to the heart 14 and a core section of heart tissue can be removed in the absence of a cardiac bypass. As another alternative, in some implementations, the core section of heart tissue can be removed before attaching the cuff 20 to the heart 14.

Figure 10C:
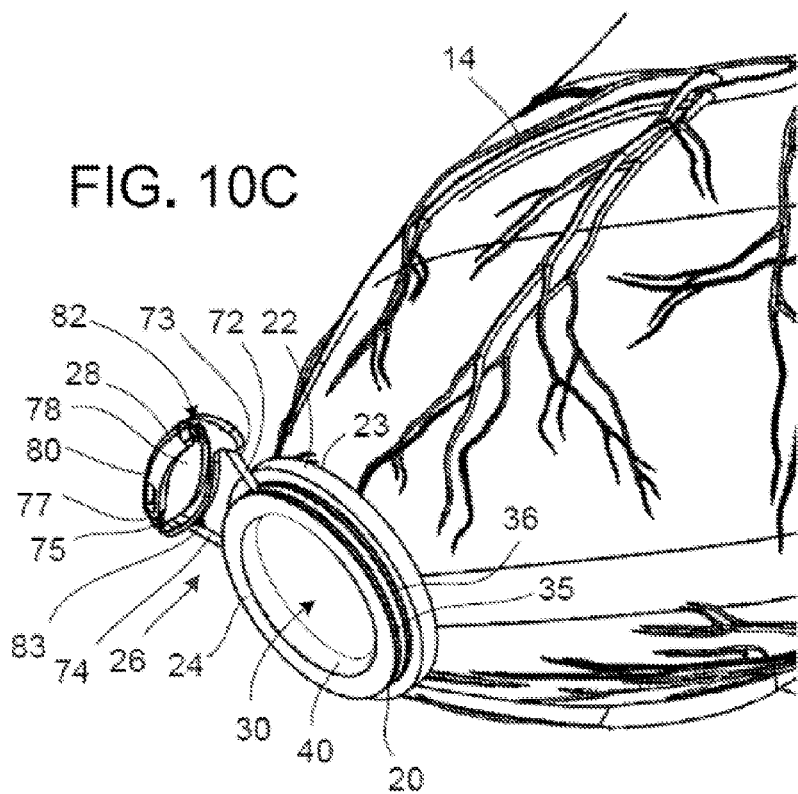

Referring to FIG. 10C, heart tissue has been removed so that the proximal portion 52 can be admitted through the opening 30 of the cuff 20. The clamp 26 of the cuff 20 is moved to its open position (not shown) and the proximal portion 52 of the cannula 50 is received through the opening 30.

Figure 10D:
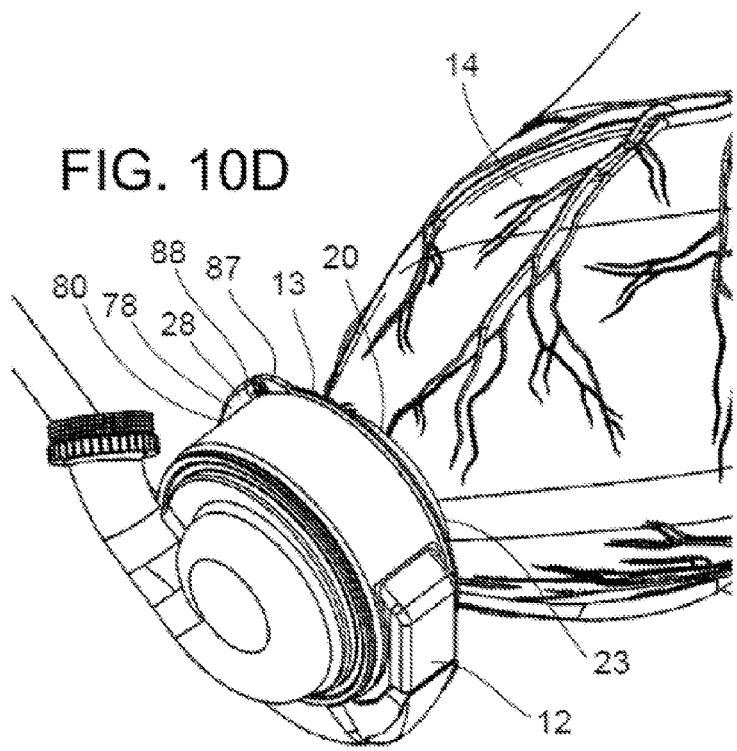

Referring to FIG. 10D, the proximal portion 52 advances through the opening 30 until the circular portion 70 of the clamp 26 is disposed about the circumferential groove 60. The clinician determines that the circular portion 70 is located about the circumferential groove 60 based on (i) snap-like tactile feedback of the circumferential ridge 58 passing through the linking member 24 and (ii) engagement of the linking member 24 to the circumferential flange 62. The clinician couples the cuff 20 to the cannula 50 by rotating the cam 28 in a plane generally parallel to the top surface 13 of the pump 12. Rotation of the cam 28 moves the clamp 26 to its closed position, in which the cannula 50 is captured within the cuff 20. The clinician rotates the cam 28 further in the plane to engage the locking mechanism of the cam 28, impeding the clamp 26 from leaving the closed position. By engaging the locking mechanism of the cam 28, orientation of the cuff 20 to the cannula 50 can be secured such that axial movement of the cannula 50 relative to the cuff 20 and rotation of the cannula 50 relative to the cuff 20 are both impeded.

The size of the cuff 20 can be selected such that, when the pump 12 is coupled to the cuff 20, the distance between the heart 14 and the top surface 13 of the pump 12 is small. For example, the total height of the cuff 20 may be, for example, between approximately 2 mm and approximately 10 mm. Because the cam 28 can be moved to a locked position by planar movement, the locking mechanism does not require clearance between the cuff 20 and the top surface 13.

In addition, the inflow cannula 50 can define two or more circumferential grooves between two or more circumferential ridges. Multiple circumferential grooves can provide different locations along the length of the cannula 50 at which the cuff 20 can be coupled. A clinician couple the cuff 20 at a particular circumferential groove to select the distance that the cannula 50 will extend into the heart 14.

The thickness of the fastening member 22 can be selected to adjust the length that the cannula 50 extends into the heart 14. The use of a thicker fastening member 22 can result in the cannula 50 extending a shorter depth into the heart 14 than the use of a thinner fastening member 22. A clinician may select a cuff 20 that includes a fastening member 22 of an appropriate thickness to set the distance that the cannula 50 extends into the heart 14.

A clinician may also adjust the distance that the cannula 50 extends into the heart by adding one or more spacers, such as a ring-shaped fabric washer, between the cuff 20 and the heart 14. For example, a clinician may place a spacer between the surface of the heart 14 and the contact surface 23 of the fastening member 22. Sutures can be placed through the fastening member 22 and through the spacer to attach the cuff 20 at an appropriate distance from the heart 14.

In some implementations, the length of the proximal portion 52 of the cannula 50 can be varied to achieve a desired length of extension of the proximal portion 52 into the heart 14. For example, several inflow cannulas having proximal portions of different lengths can be fabricated. A clinician can select an inflow cannula that has a proximal portion corresponding to the desired length of extension into the heart of a particular patient, and can couple the selected inflow cannula to a pump before or during a procedure.

As an alternative to the clamp 26, the cuff 20 may include a resilient metal split ring. A break or gap in the split ring permits the diameter of the split ring to expand as it travels over the circumferential groove 58 of the cannula 50. Once the split ring is located about the circumferential groove 60, the split ring contracts into the circumferential groove 60 to couple the cuff 20 to the cannula 50. The split ring may thus be operated without arms extending from the split ring and without a cam.

Figure 11A:
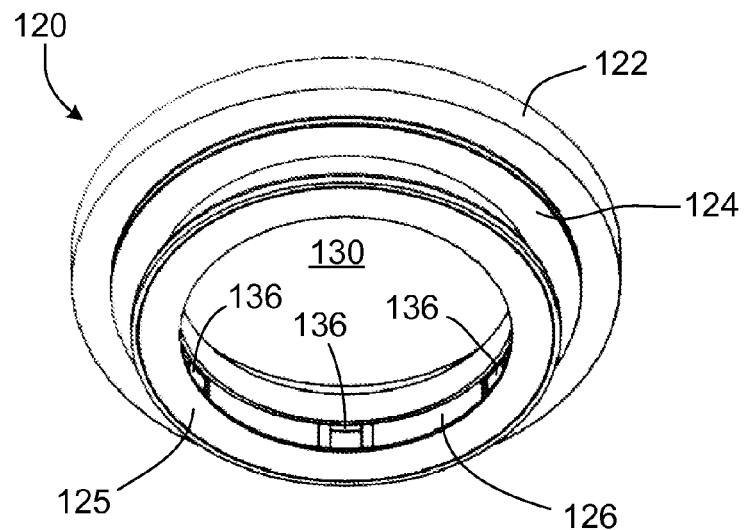
FIG. 11A is a perspective view of a ventricular cuff.
Figure 11B:
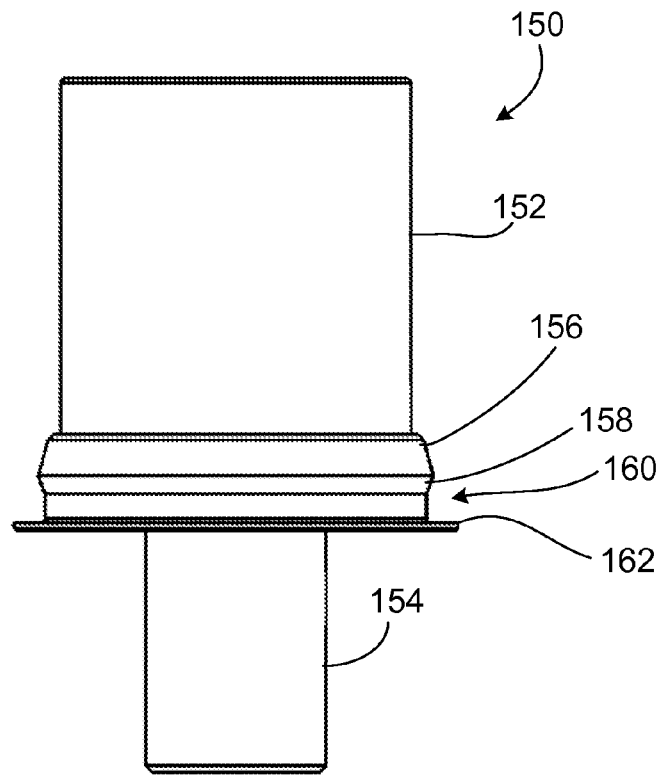
FIG. 11B is a side view of a cannula for coupling to the ventricular cuff of FIG. 11A.

Referring to FIGS. 11A and 11B, an alternative cuff 120 and an alternative cannula 150 can be used to couple a pump 250 (FIG. 14A) to heart tissue. A coupling mechanism, for example, an attachment member 126, couples the cuff 120 to the cannula 150. A locking mechanism in the form of a clip 200 (FIG. 13A) impedes the cuff 120 from becoming uncoupled from the cannula 150.

The cuff 120 defines an opening 130 that admits a proximal portion 152 of the cannula 150. The cuff 120 includes an annular fastening member 122, a linking member 124, and the attachment member 126. The fastening member 122 can be sutured to heart tissue, and can include, for example, a fabric such as PTFE felt.

The linking member 124 is formed of, for example, an elastomer such as silicone, and includes a reinforcement member 128 (FIG. 16) such as a mesh ring. The linking member 124 is disposed about an outer circumference of the attachment member 126 and serves as a linking member to couple the attachment member 126 to the fastening member 122, as discussed further below. The linking member 124 is coupled to the fastening member 122 by, for example, sutures. The linking member 124 can also be molded directly to the fastening member 122. The linking member 124 includes a bottom surface 125 configured to engage a generally flat circumferential flange 162 of the cannula 150, forming a face seal with the circumferential flange 162.

The cannula 150 includes the proximal portion 152 that enters the opening 130 of the cuff 120 and a distal portion 154 that is housed in the pump 250. The cannula 150 includes a first circumferential taper 156 that engages extensions 136 of the attachment member 126 and deflects them away from the cannula 150 as the cannula 150 advances through the opening 130. The cannula 150 includes a second circumferential taper 158 and defines a circumferential groove 160 between the second circumferential taper 158 and the circumferential flange 162.

Figure 12A:
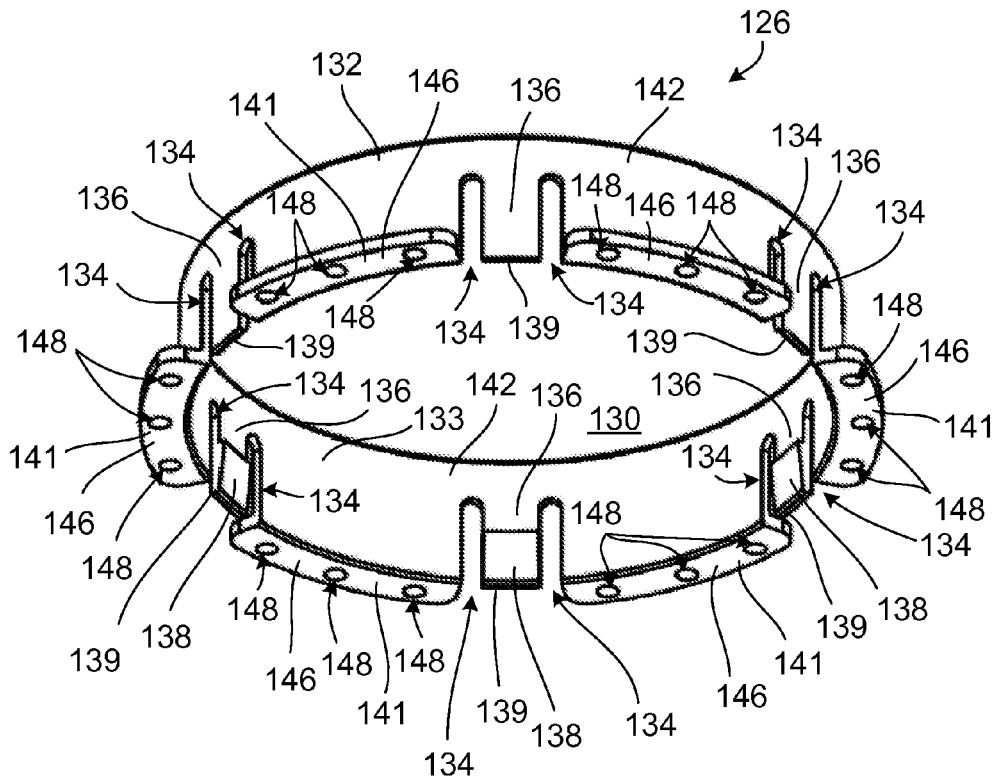
FIG. 12A is a perspective view of an attachment member of the ventricular cuff of FIG. 11A.
Figure 12B:
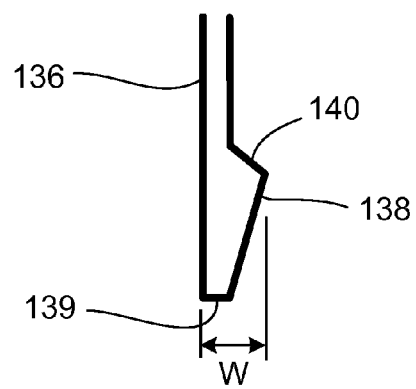
FIG. 12B is a side cutaway view of an extension of the attachment member.

Referring to FIGS. 12A and 12B, the attachment member 126 is formed of, for example, a rigid material such as metal. The attachment member 126 includes a ring portion 132 having a wall 133 with cutouts 134 that define flexible extensions 136. Each extension 136 includes a lower tapered portion 138 (FIG. 12B) disposed on a free end 139 of the extension 136, facing inward toward the opening 130. As the first circumferential taper 156 of the cannula 150 is inserted through the opening 130, the lower tapered portions 138 engage the first circumferential taper 156, causing the extensions 136 to flex outward from the opening 130 and permit the first circumferential taper 156 to pass through the opening 130. When the lower tapered portions 138 are disposed in the circumferential groove 160, the lower tapered portions 138 engage the second circumferential taper 158 of the cannula 150 to impede the cannula 150 from easily exiting the cuff 120. Each lower tapered portion 138 includes upper tapered portion 140, and the width of each lower tapered portion 138, W, decreases along the length of each lower tapered portion 138, between the upper tapered portion 140 and the free end 139.

The extensions 136 can have equal sizes or can be selected to have differing sizes. For example, asymmetrical lengths of the extensions 136 can cause the extensions 136 to engage the circumferential tapers 156, 158 sequentially rather than consecutively during travel of the cannula 150 relative to the cuff 120, reducing the force required to couple the cannula 150 to the cuff 120 or to uncouple the cannula 150 from the cuff 120.

The amount of force required to deflect the extensions is correlated with the angle of the taper of the circumferential tapers 156, 158 and the tapered portions 138, 140. The steepness of the taper angles can be selected such that different amounts of force along the length of the cannula 150 are required to couple the cuff 120 to the cannula 150 can remove the cuff 120 from the cannula 150. The engagement of tapers with a steep angle results in a lower percentage of axial force being transmitted radially outward than the engagement of shallower tapers. Thus to allow the cuff 120 to be coupled to the cannula 150 with a smaller force than the force required to remove the cuff 120 from the cannula 150, the tapers of the lower tapered portions 138 and the circumferential taper 156 are less steep than the tapers of the upper tapered portions 140 and the circumferential taper 158. Accordingly, more force is required to decouple the cuff 120 than to couple the cuff 120 to the cannula 150. The amount of force required to couple the cuff 120 to and decouple the cuff 120 from the cannula 150 can be adjusted by the materials selected for the attachment member 126, the thickness of the extensions 136, the length and width of the extensions 136, and the geometry of the cutouts 134.

The attachment member 126 includes flanged portions 146, disposed between the extensions 136 along the outer circumference of the attachment member 126, at the bottom 141 of the attachment member 126. The flanged portions 146 extend generally perpendicular to the wall 133. When the cuff 20 is coupled to the cannula 150, the flanged portions 146 are disposed in a plane generally parallel to the circumferential flange 162 of the cannula 150. When the cuff 20 is locked to the cannula 150, the flanged portions 146 are captured between the clip 200 and the circumferential flange 162, impeding the cuff 120 from becoming uncoupled from the cannula 150.

Figure 16:
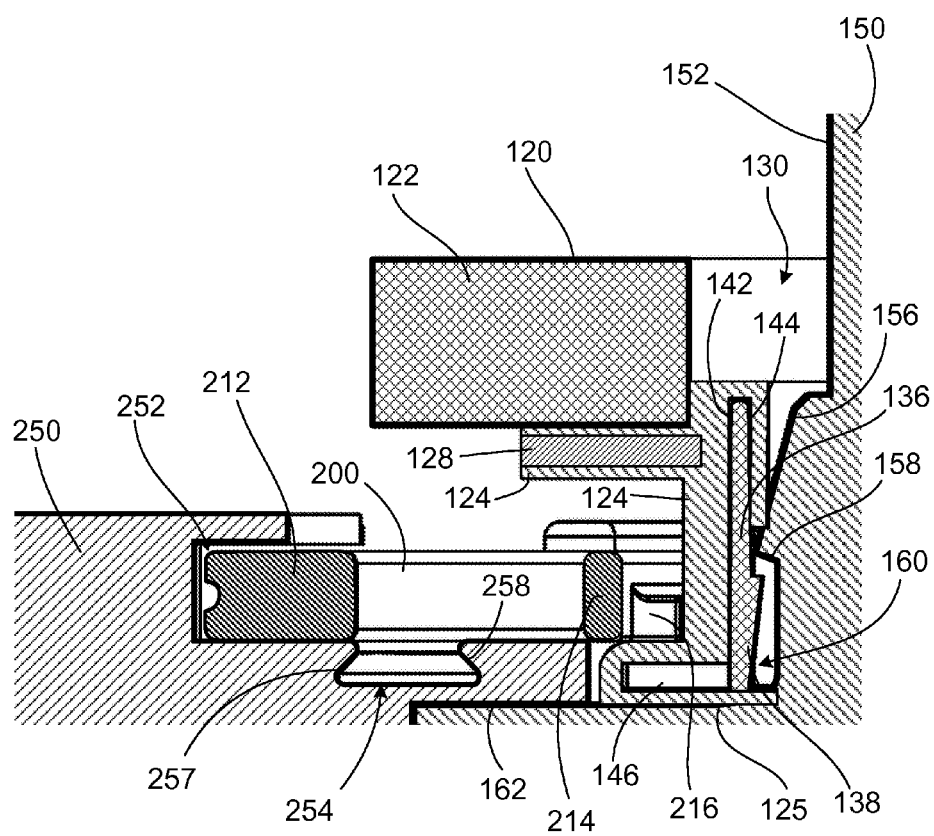
FIG. 16 is a side cross-sectional view of the ventricular cuff of FIG. 11A coupled to the cannula of FIG. 11B across line 16-16 of FIG. 15C.

The flanged portions 146 define holes 148 through which material of the linking member 124 is molded or adhesive is applied to form mechanical locks that secure the linking member 124 to the attachment member 126. Material of the linking member 124 is also molded or adhesively bonded through the cutouts 134 and over the ring portion 132. For example, silicone can be molded over the attachment member 126 and can be molded over a portion of the fastening member 122. The linking member 124 can also be coupled to the attachment member 126 with adhesive or sutures. The linking member 124 covers the flanged portions 146, an outer surface 142 of the wall 133, and a portion of an inner surface 144 of the wall 133 (FIG. 16).

The flanged portions 146 and extensions 136 are disposed symmetrically along the circumference of the attachment member 126, permitting the extensions 136 to engage the circumferential tapers 156, 158 evenly about the cannula 150, and permitting the flanged portions 146 to evenly press the bottom surface 125 of the linking member 124 into engagement with the circumferential flange 162. The attachment member 126 can include more or fewer flanged portions 146 and extensions 136 than those illustrated.

To couple the cannula 150 to the cuff 120, a clinician inserts the proximal portion 152 of the cannula 150 through the opening 130. As the cannula 150 advances through the opening 130, the first circumferential taper 156 passes the upper tapered portion 140 of the lower tapered portions 138. The engagement of the lower tapered portions 138 with the first circumferential taper 156 (which resists advancement of the cannula 150 by deflecting the extensions 136) ends abruptly, permitting the extensions 136 to straighten so that the lower tapered portions 138 reside in the circumferential groove 160. The sudden decrease in resistance to advancement of the cannula 150 produces a tactile snap-like sensation, indicating to the clinician that the cannula 150 is coupled to the cuff 120. The upper tapered portion 140 of the lower tapered portions 138 engage the second circumferential taper 158, impeding the cannula 150 from separating from the cuff 120. The bottom surface 125 of the linking member 124 engages the circumferential flange 162, limiting further advancement of the cannula 150 relative to the cuff 120.

After the cannula 150 and cuff 120 are coupled, the cannula 150 can be separated from the cuff 120 by a force sufficient to deflect the extensions 136. Engagement of the upper tapered portions 140 with the second circumferential taper 158 deflects the extensions 136, allowing the cannula 150 to be removed from the cuff 120.

Figure 13A:
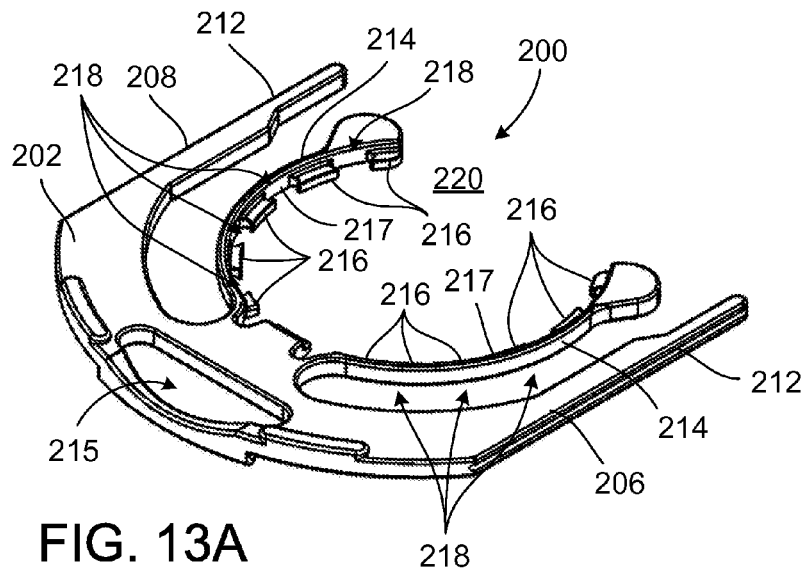
FIG. 13A is a perspective view illustrating the top of a clip.
Figure 13C:
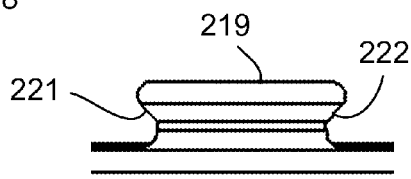
FIG. 13C is a side view of a post of the clip.
Figure 13B:
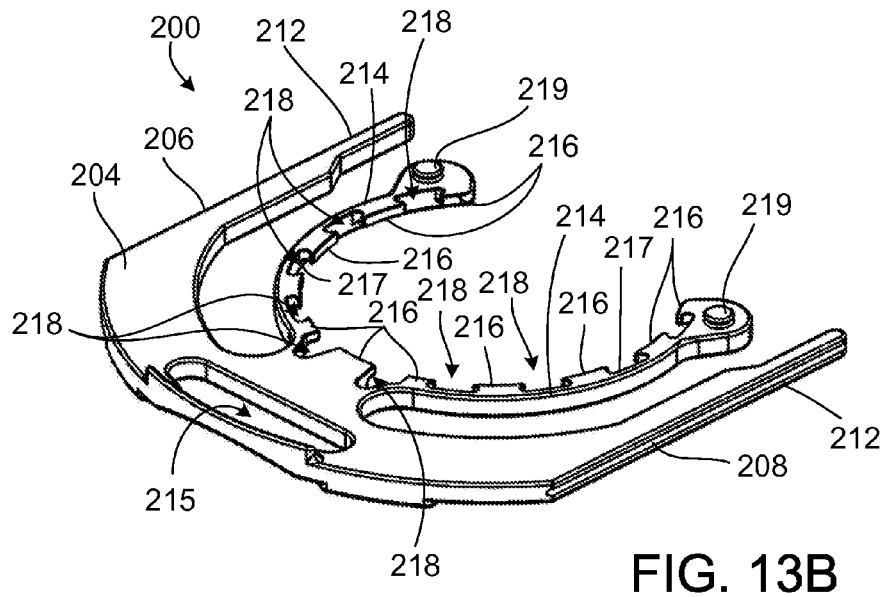
FIG. 13B is a perspective view illustrating the bottom of the clip.

Referring to FIGS. 13A and 13B, the clip 200 is used to secure the cuff 120 about the cannula 150. The clip 200 cooperates with features of the pump 250, described below, to limit travel of the cuff 120 relative to the cannula 150. The clip 200 includes a top side 202, a bottom side 204, and opposite lateral sides 206, 208. The clip 200 can be formed of, for example, a rigid plastic, such as PEEK, or metal, such as titanium.

The clip 200 includes guide rails 212 and arms 214, and defines a recess or opening 215 or opening. The guide rails 212 guide the clip 200 through a linear motion as the clip 200 is received by the pump 250. The opening 215 admits a tool or a finger of the clinician to facilitate disengagement of the clip 200 from its locked position relative to the cuff 120. The arms 214 are curved and resilient, and define an opening 220. As the clip 200 moves relative to the pump 250, the pump 250 forces the arms 214 laterally outward, expanding the opening 220 and allowing the arms 214 to extend about the linking member 124 of the cuff 120. In the locked position of the clip 200, the pump 250 forces the arms 214 laterally inward to engage the linking member 124 and to secure the cuff 120 to the pump 250.

The arms 214 include teeth 216 that extend from inner walls 217 of the arms 214 toward the opening 220. In the locked position of the clip 200, the teeth 216 are disposed over the flanged portions 146 of the attachment member 126, thus capturing the flanged portions 146 between the teeth 216 and the circumferential flange 162 of the cannula 150. Between the teeth 216 are gaps 218 that permit the arms 214 to flex laterally as the clip 200 is received by the pump 250. When the clip 200 is in a locked position about the cuff 120, the teeth 216 engage the linking member 124 of the cuff 120 to impede rotation of the cuff 120 relative to the clip 200 and the pump 250.

Each arm 214 includes a post 219 extending from the bottom side 204 that is received in one of the channels 254 (FIG. 14A) defined by the pump 250. As the pump 250 receives the clip 200, the posts 219 travel through the channels 254, directing the lateral flexion of the arms 214. The posts 219 each include angled walls 221, 222 (FIG. 13C) that engage angled walls 257, 258 (FIG. 16) of the pump 250 that define the channels 254, capturing the posts 219 in the channels 254.

Figure 14A:
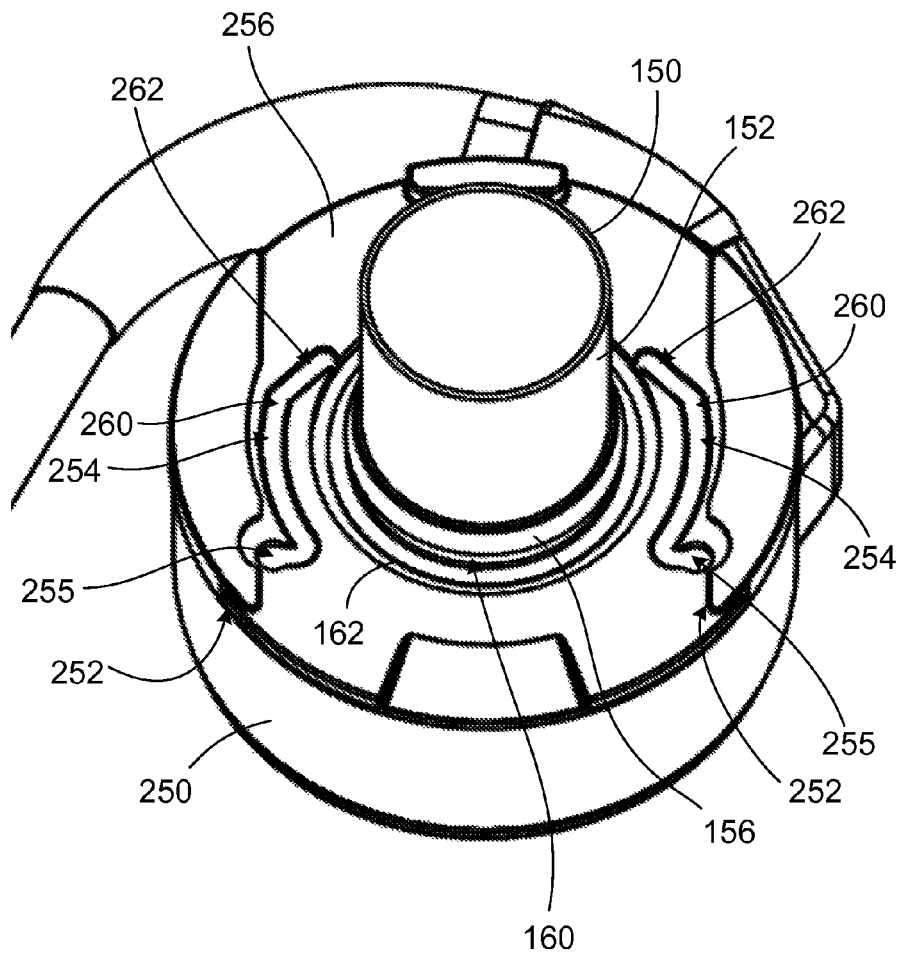
FIGS. 14A to 14C are perspective views illustrating the engagement of the clip with a pump.

Referring to FIG. 14A, the pump 250 is coupled to the cannula 150 and receives a clip 200. The pump 250 defines generally parallel slots 252 that receive the guide rails 212 of the clip 200. The pump 250, in a top side 256, also defines the channels 254 that receive the posts 219 between the angled walls 257, 258 (FIG. 16). The angled walls 257, 258 capture the posts 219, impeding the posts 219 from leaving the channels 254 and maintaining the arms 214 in a plane above the top side 256. The portion of the pump 250 that defines the channels 254 can be an integral component of, for example, a motor housing of the pump, or can be a separate component that attaches to the pump 250, for example, with welds, screws, or other fastening mechanisms.

The pump 250 defines an entry recess 255 at each channel 254 that admits the post 219. The distance between the entry recesses 255 is larger than the distance between the posts 219 when the arms 214 of the clip 200 are not flexed.

To insert the posts 219 into the channels 254, the clinician flexes the arms 214 outward, loading the resilient arms 214 and permitting the posts 219 to enter the channels 254 at the entry recesses 255. After the posts 219 are positioned in the entry recesses 255, the arms 214 flex inward to their natural resting condition, moving the posts 219 in the channels 254 away from the entry recesses 255. Because the posts 219 are captured in the channels 254, the clip 200 will not separate from the pump 250 until the clinician flexes the arms 214 outward and upward, permitting the posts 219 to leave the channels 254 at the entry recesses 255. The pump 250 can be provided with the clip 200 already positioned in the channels 254, and thus already captured by the pump 250, to streamline the implantation procedure.

A first portion 260 of the channels 254 curves outward about the cannula 150 to spread the arms 214, permitting the arms 214 to extend about the cannula 150 and the linking member 124 of the cuff 120. A second portion 262 of the channels 254 curves inward toward the cannula 150, moving the arms 214 inward about the cannula 150.

Figure 14B:
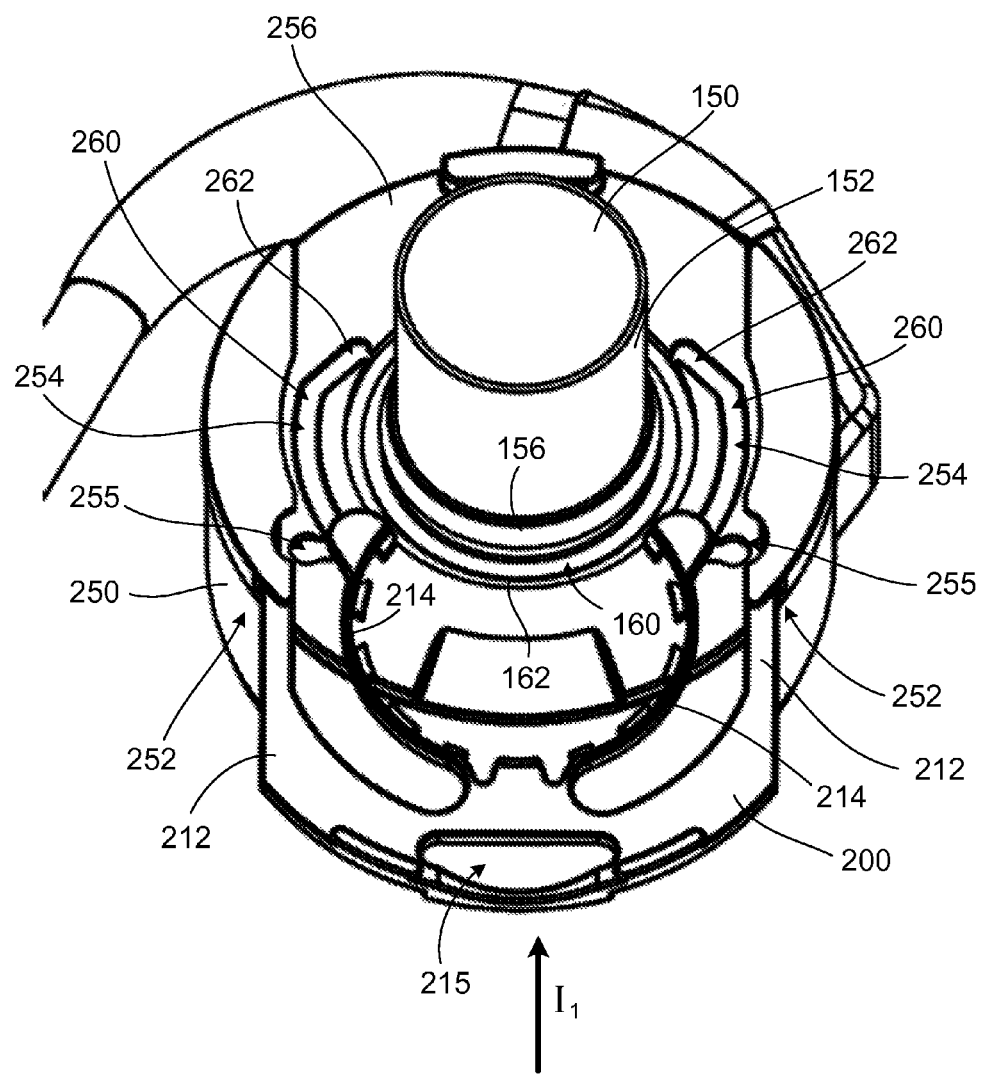
Figure 14C:
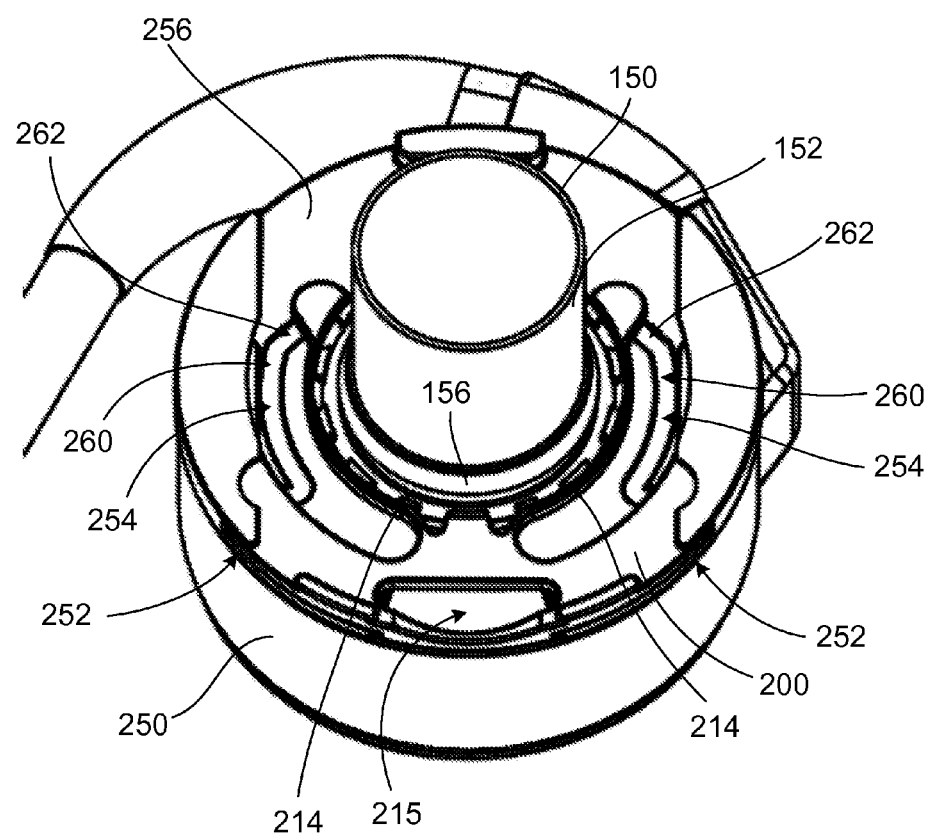

Referring to FIG. 14B, the guide rails 212 of the clip 200 enter the slots 252, and the posts 219 are captured in the channels 254. The clip 200 travels in a generally linear direction relative to the pump 250, in the direction of arrow $I_1$, until the clip 200 reaches the position of FIG. 14C. As the clip 200 is advanced into the pump 250, the force in the direction of arrow $I_1$ causes the posts 219 to deflect outward in the channels 254. Once the posts 219 have reached the peak distance between the channels 254, the insertion force required in the direction of arrow $I_1$ lessens as the inward deflection force of the arms 214 drive the clip 200 through the second portion 262 of the channels 254. The clip 200 travels linearly as the posts 219 travel through the channels 254, until the position of FIG. 14C is reached in which the arms 214 are in their relaxed position.

To move the clip 200 back to the unlocked position, the clip 200 is retracted in a direction opposite the arrow $I_1$, and the posts 219 travel in the opposite direction through the channels 254. During removal of the clip 200, the second portion 262 expands the arms 214 and the first portion 260 permits the arms 214 to become closer together. The angle of the first portion 260 is less steep than the angle of the second portion 262, which results in the force to remove the clip 200 being higher than the force to move the clip 200 into the locking position.

Figure 15A:
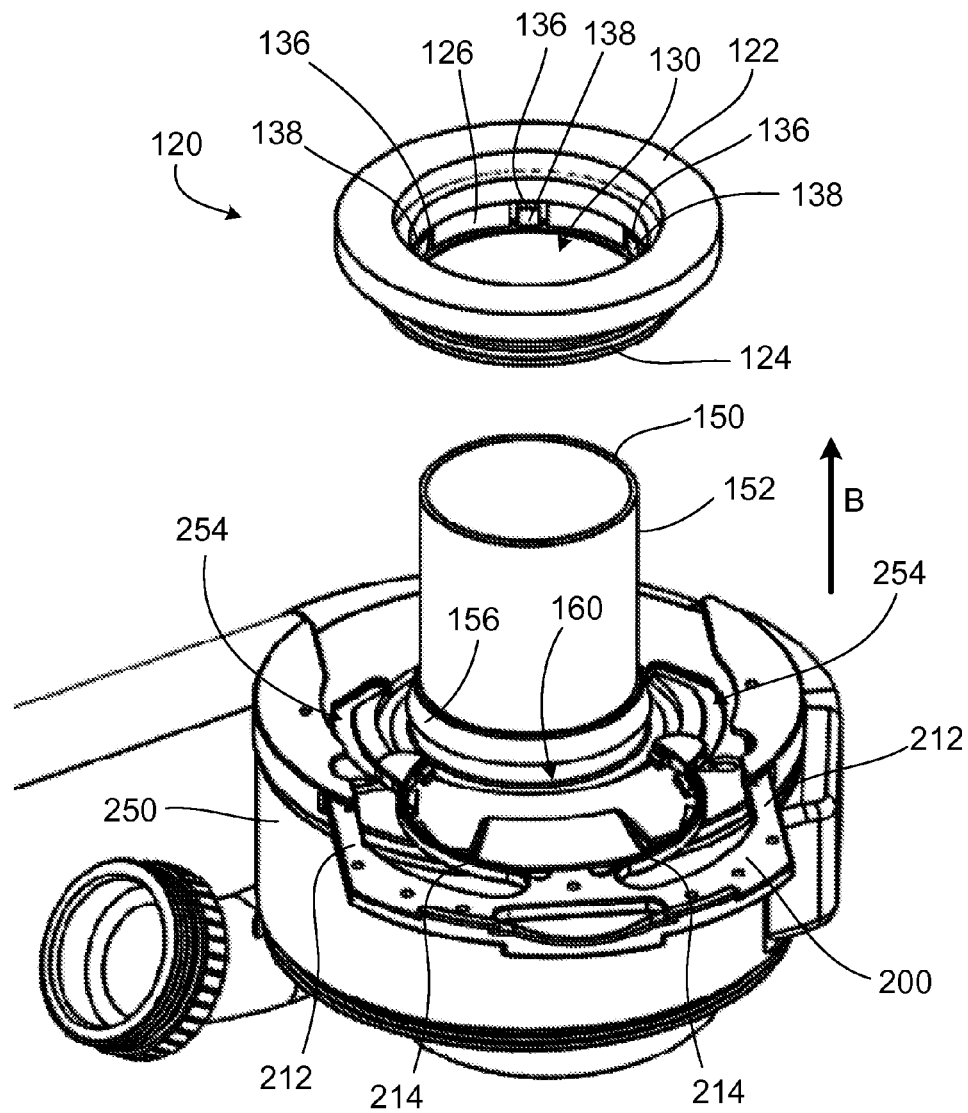
FIGS. 15A to 15C are perspective views illustrating the coupling of the pump of FIG. 14A to the ventricular cuff of FIG. 11A using the clip.

Referring to FIG. 15A, a clinician moves the pump 250 and the cannula 150 relative to the cuff 120, in the direction of arrow B, so that the proximal portion 152 enters the opening 130 of the cuff 120. As the cannula 150 advances, the first circumferential taper 156 deflects the extensions 136 away from the cannula 150. The first circumferential taper 156 and the second circumferential taper 158 advance past the tapered portions 138 of the extensions 136. As the first circumferential taper 156 advances past the tapered portions 138, the deflected extensions 136 straighten, forcing the tapered portions 138 into the circumferential groove 160. The clinician experiences tactile feedback, such as a snap-like sensation, that indicates that the cannula 150 is coupled to the cuff 120. The bottom surface 125 of the linking member 124 engages the circumferential flange 162 of the cannula 150. In some implementations, the bottom surface 125 engages a surface of the pump 250 as an alternative to, or in addition to, engaging a portion of the cannula 150.

Figure 15B:
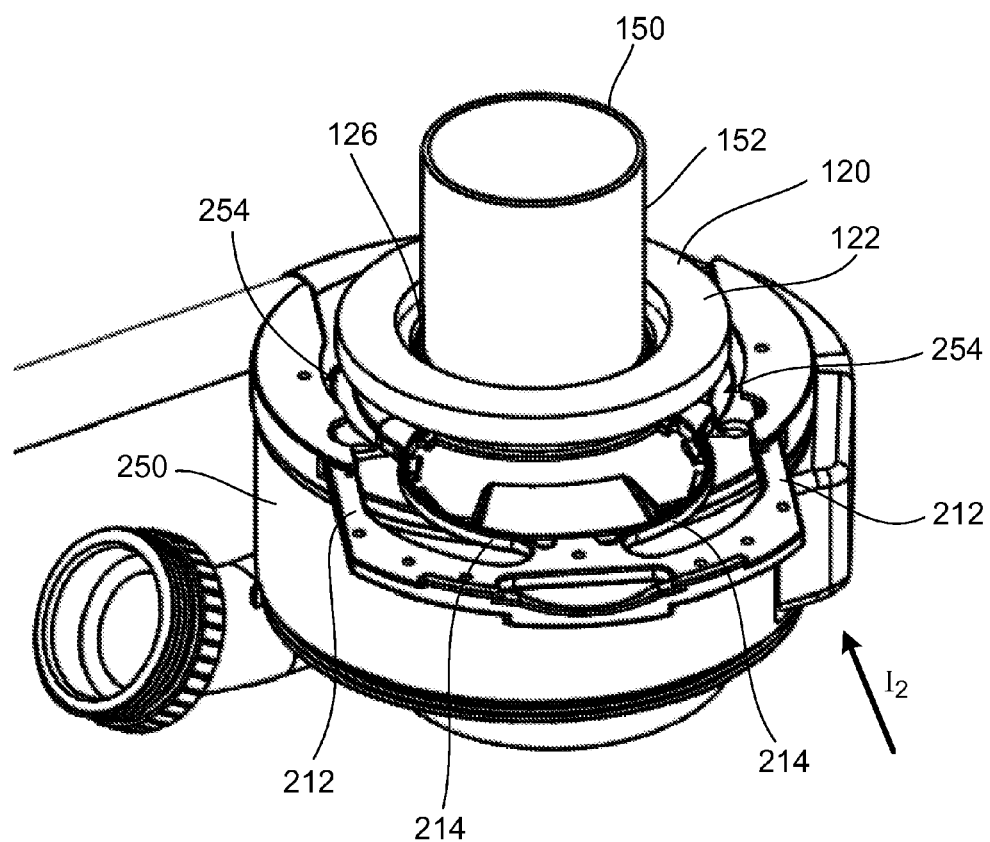

Referring to FIG. 15B, the clinician advances the clip 200 into the pump 250. The guide rails 212 of the clip 200 travel in the slots 252, guiding the clip 200 as it travels linearly in a plane above the top side 256, in the direction of arrow $I_2$. As the clip 200 travels relative to the pump 250, the arms 214 flex laterally due to engagement of the posts 219 with the angled walls 257, 258 defining the channels 254. The arms 214 move laterally outward to admit the linking member 124 and then laterally inward to engage the linking member 124.

Figure 15C:
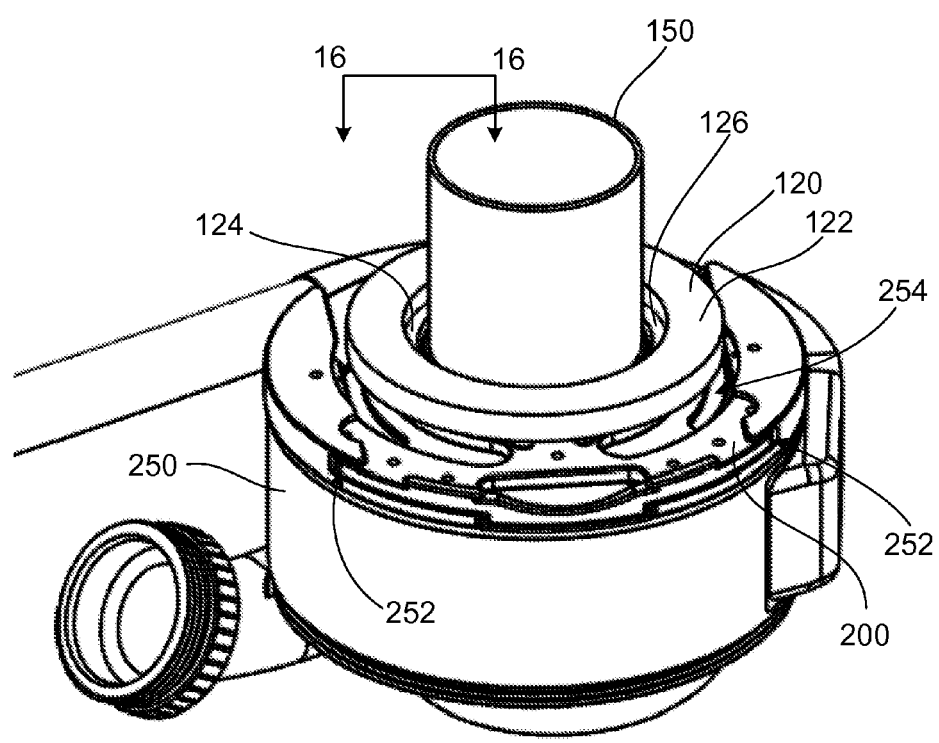

Referring to FIG. 15C, the clip 200, in its locked position, limits travel of the cuff 120 relative to the cannula 150. The engagement of the posts 219 with the angled walls 257, 258 that define the channels 254 forces the arms 214 inward such that the teeth 216 of the arms 214 are disposed over the flanged portions 146 of the attachment member 126. The flanged portions 146 are captured between the teeth 216 and the circumferential flange 162. The engagement of the teeth 216 to the linking member 124 presses the bottom surface 125 against the circumferential flange 162, forming a seal (FIG. 16).

In an implanted state, after the clip 200 is in its locked position, the pump 250 and the cannula 150 are in a position suitable for long-term stability relative to the cuff 120 and the heart. While the clip 200 is in its locked position, an extremely large force is required to remove the cuff 120 from the cannula 150. For example, the force required to forcibly separate the pump 250 or cannula 150 from the cuff 120 while the clip 200 is in its locked position can be as large as the force required to tear the cuff 120 from the heart.

The distance that the cannula 150 extends into a heart can be selected in a similar manner as described above. For example, a cannula 150 with a proximal portion 152 having a particular length can be selected, one or more spacers can be placed between the fastening member 122 and a heart, or the thickness of the fastening member 122 can be selected for a particular patient.

Figure 17A:
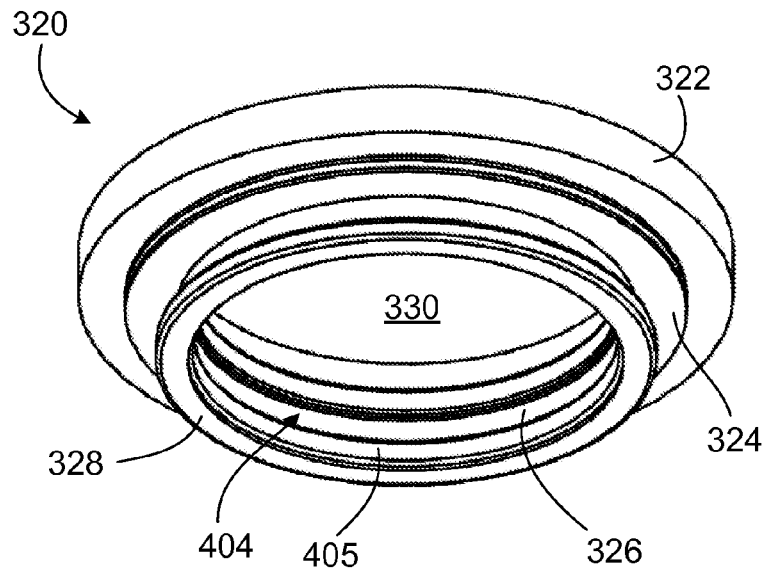
FIG. 17A is a perspective view of a ventricular cuff.
Figure 17B:
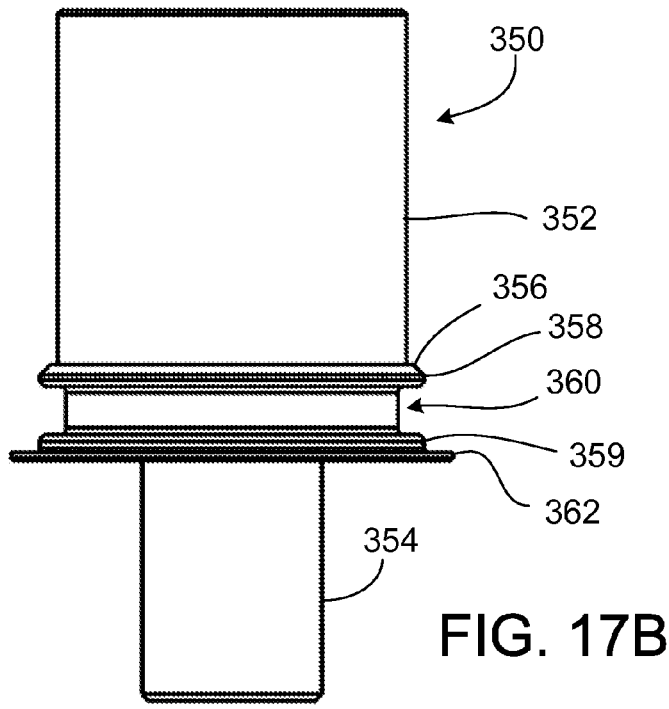
FIG. 17B is a side view of a cannula for coupling to the ventricular cuff of FIG. 17A.

Referring to FIGS. 17A and 17B, an alternate implementation includes a cuff 320 and a cannula 350 configured to cooperate with the pump 250 and the clip 200. The cuff 320 defines an opening 330 that admits a proximal portion 352 of the cannula 350. A coupling mechanism in the form of an attachment member 326 engages a sealing ring 502 (FIG. 19A), such as an o-ring, disposed about the cannula 350 to couple the cuff 320 to the cannula 350. The clip 200 (FIG. 13A) acts as a locking mechanism to impede the cuff 320 from becoming uncoupled from the cannula 350.

The cuff 320 includes an annular fastening member 322 that a clinician can fasten to heart tissue. For example, the fastening member 322 can be formed of a fabric such as PTFE felt. The cuff 320 includes a linking member 324 coupled to the fastening member 322, for example, by sutures or direct molding. The linking member 324 is formed of, for example, an elastomer such as silicone. The linking member 324 includes a reinforcement member 325 (FIG. 18B), such as a mesh ring. The linking member 324 couples the attachment member 326 to the fastening member 322, as described below.

The linking member 324 includes a bottom surface 328 that engages a circumferential flange 362 of the cannula 350. The primary sealing mechanism between the cuff 320 and the cannula 350 is the sealing ring 502, and as a result, the linking member 324 and the circumferential flange 362 are not required to form a seal. Nevertheless, in some implementations, the linking member 324 may form a secondary seal with the circumferential flange 362. In some implementations, the bottom surface 328 engages a surface of the pump 250 as an alternative to, or in addition to, engaging a portion of the cannula 350.

The cannula 350 includes the proximal portion 352, the circumferential flange 362, and a distal portion 354 housed within the pump 250. The cannula 350 includes a circumferential taper 356 that engages a circumferential taper 405 of the attachment member 326, guiding the cuff 320 into alignment with the cannula 350. The cannula 350 defines a circumferential groove 360 between a first circumferential ridge 358 and a second circumferential ridge 359. The circumferential groove 360 receives the sealing ring 502.

Figure 18A:
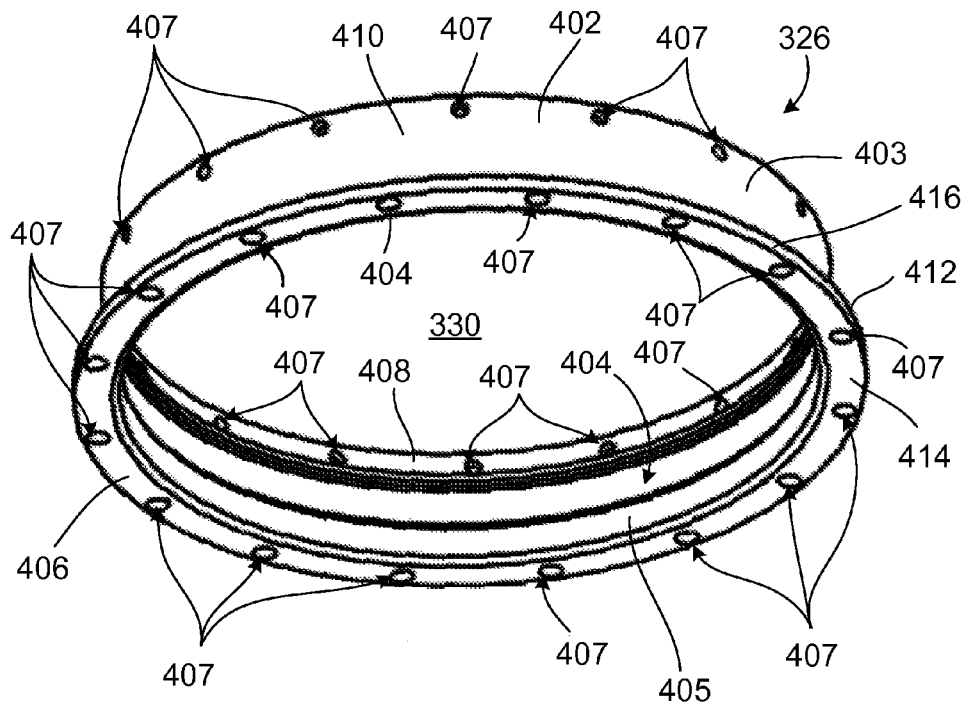
FIG. 18A is a perspective view of an attachment member of the ventricular cuff of FIG. 17A.
Figure 18B:
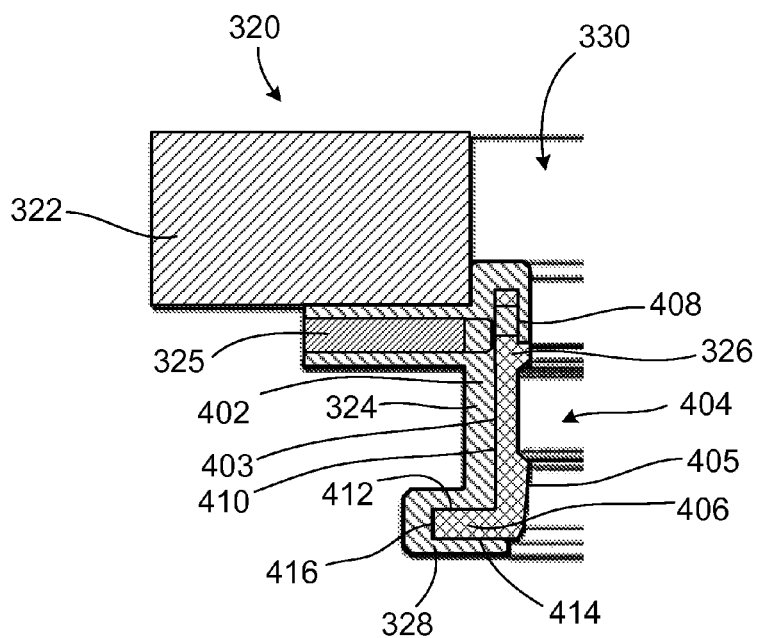
FIG. 18B is a cross-sectional view of a portion of the ventricular cuff of FIG. 17A.

Referring to FIGS. 18A and 18B, the attachment member 326 is formed of, for example, a rigid material such as metal or PEEK. The attachment member 326 includes a cylindrical portion 402, which defines an inner circumferential groove 404 that admits a portion of the sealing ring 502. The sealing ring 502 is formed of, for example, an elastomer such as silicone or implantable-grade ethylene propylene diene monomer (EPDM). In some implementations, the attachment member 326 does not define an inner circumferential groove 404 and instead has a substantially cylindrical inner surface.

The attachment member 326 includes a flanged portion 406, for example, a circumferential flange that extends in a plane generally perpendicular to an outer wall 403 of the cylindrical portion 402. The attachment member 326 includes the inner circumferential taper 405 that engages the sealing ring 502, compressing the sealing ring 502 and permitting the sealing ring 502 to enter the inner circumferential groove 404.

The linking member 324 is molded over the attachment member 326, and the flanged portion 406 and the cylindrical portion 402 define holes 407 that admit material of the linking member 324. The material of the linking member 324 that extends through the holes 407 forms mechanical locks that couple the linking member 324 to the attachment member 326. The linking member 324 is molded over an inner circumferential wall 408 and an outer circumferential surface 410 of the cylindrical portion 402, as well as a top surface 412, a bottom surface 414, and a circumferential side surface 416 of the flanged portion 406.

Figure 19A:
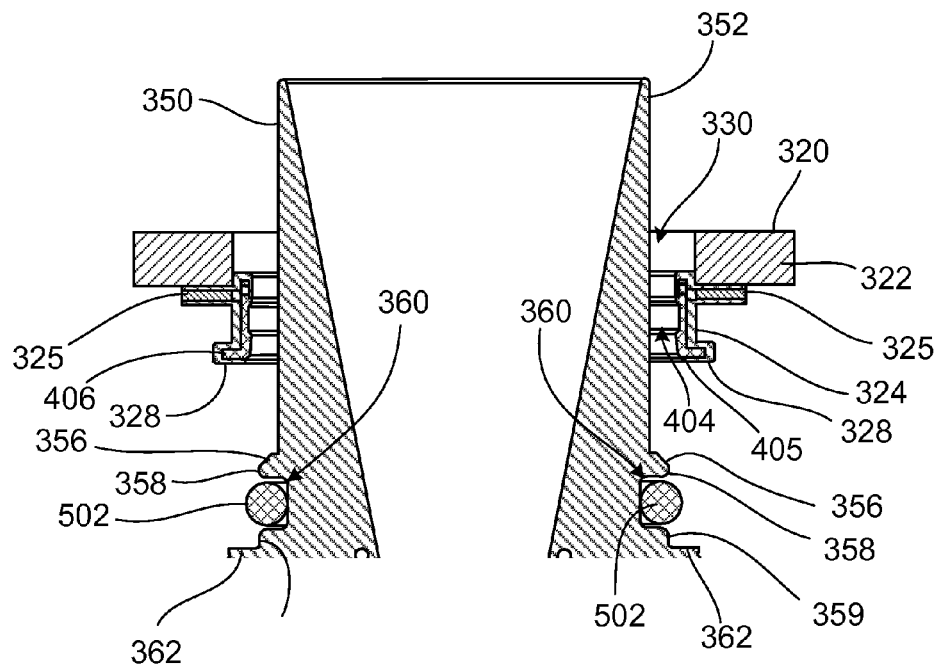
FIGS. 19A and 19B are cross-sectional views illustrating the engagement of the ventricular cuff of FIG. 17A with the cannula of FIG. 17B.
Figure 19B:
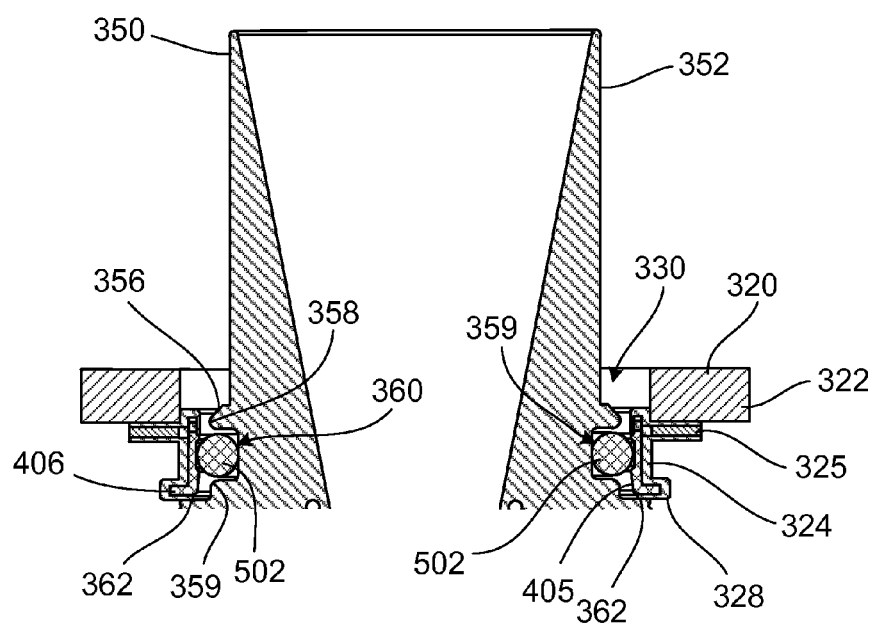

Referring to FIGS. 19A and 19B, the sealing ring 502 is disposed in the circumferential groove 360. To couple the cannula 350 to the cuff 320, the clinician moves the proximal portion 352 through the opening 330 of the cuff 320. The sealing ring 502 engages the circumferential taper 405 of the attachment member 326, compressing the sealing ring 502 into the circumferential groove 360.

As the cannula 350 advances through the opening 330, the sealing ring 502 advances past the circumferential taper 405 to the position of FIG. 19B. The sealing ring 502 expands into the circumferential groove 404 of the attachment member 326 and the bottom surface 328 of the linking member 324 engages the circumferential flange 362. The sealing ring 502 is partially disposed in the circumferential groove 404 and partially disposed in the circumferential groove 360 of the cannula 350. The engagement of the sealing ring 502 between the cuff 320 and the cannula 350 limits travel of the cannula 350 relative to the cuff 320, coupling the cannula 350 to the cuff 320. The expansion of the sealing ring 502 into the circumferential groove 404 provides snap-like tactile feedback to the clinician, indicating that the cannula 350 is coupled to the cuff 320. The sealing ring 502 also creates a hemostatic seal between the cannula 350 and the cuff 320.

Figure 20:
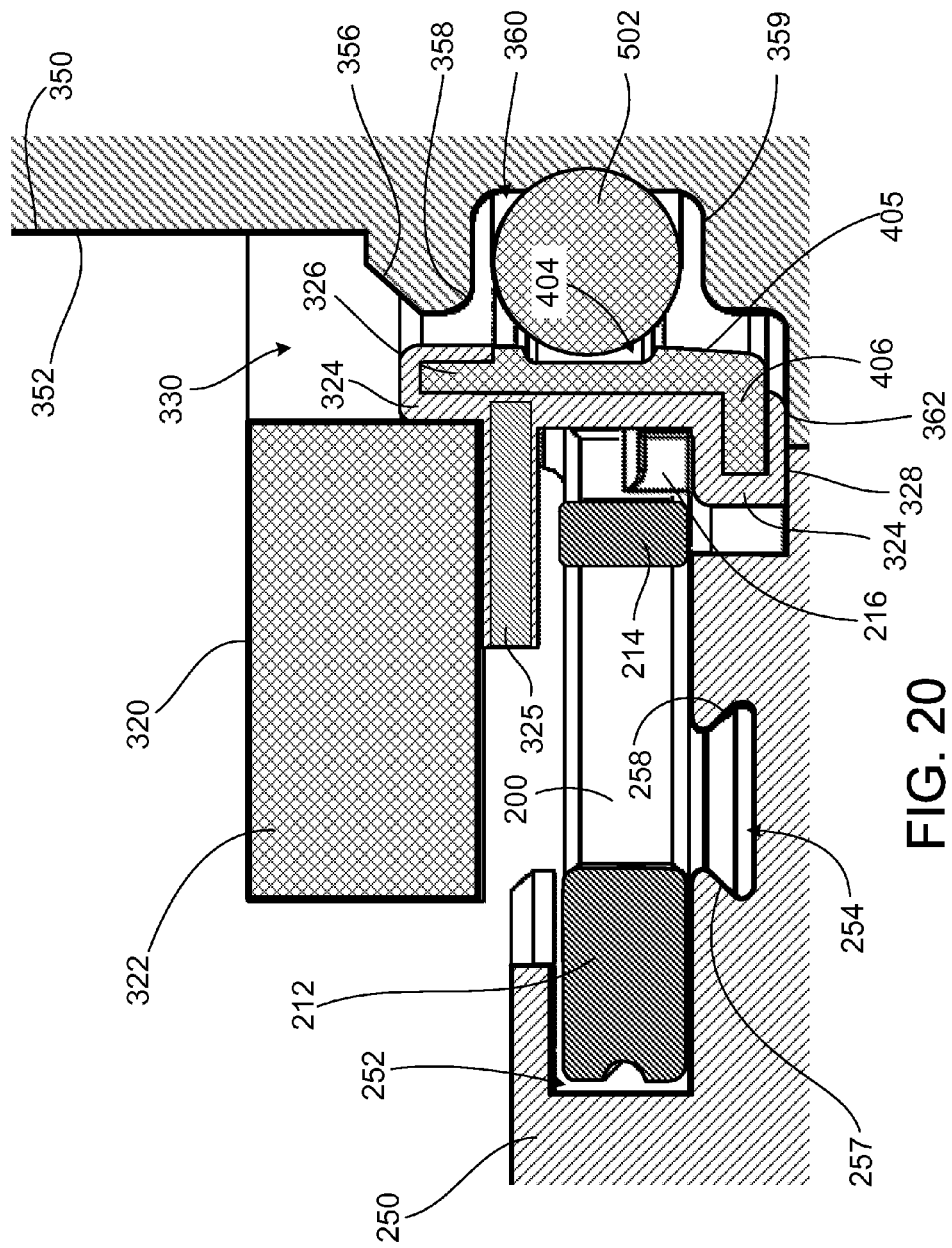
FIG. 20 is a side cross-sectional view of the ventricular cuff of FIG. 17A coupled to the cannula of FIG. 17B and secured to the pump of FIG. 14A using the clip.

From the position of FIG. 19B, the clinician can move the clip 200 into a locked position about the cuff 320 as described above with reference to FIGS. 14A to 14C. With the clip 200 in its locked position (FIG. 20), the flanged portion 406 is captured between the clip 200 and the circumferential flange 362, impeding the cuff 320 from becoming separated from the cannula 350.

The distance that the cannula 350 extends into a heart can be selected in a similar manner as described above. For example, a cannula 350 with a proximal portion 352 having a particular length can be selected, one or more spacers can be placed between the fastening member 322 and a heart, or the thickness of the fastening member 322 can be selected for a particular patient.

Figure 21:
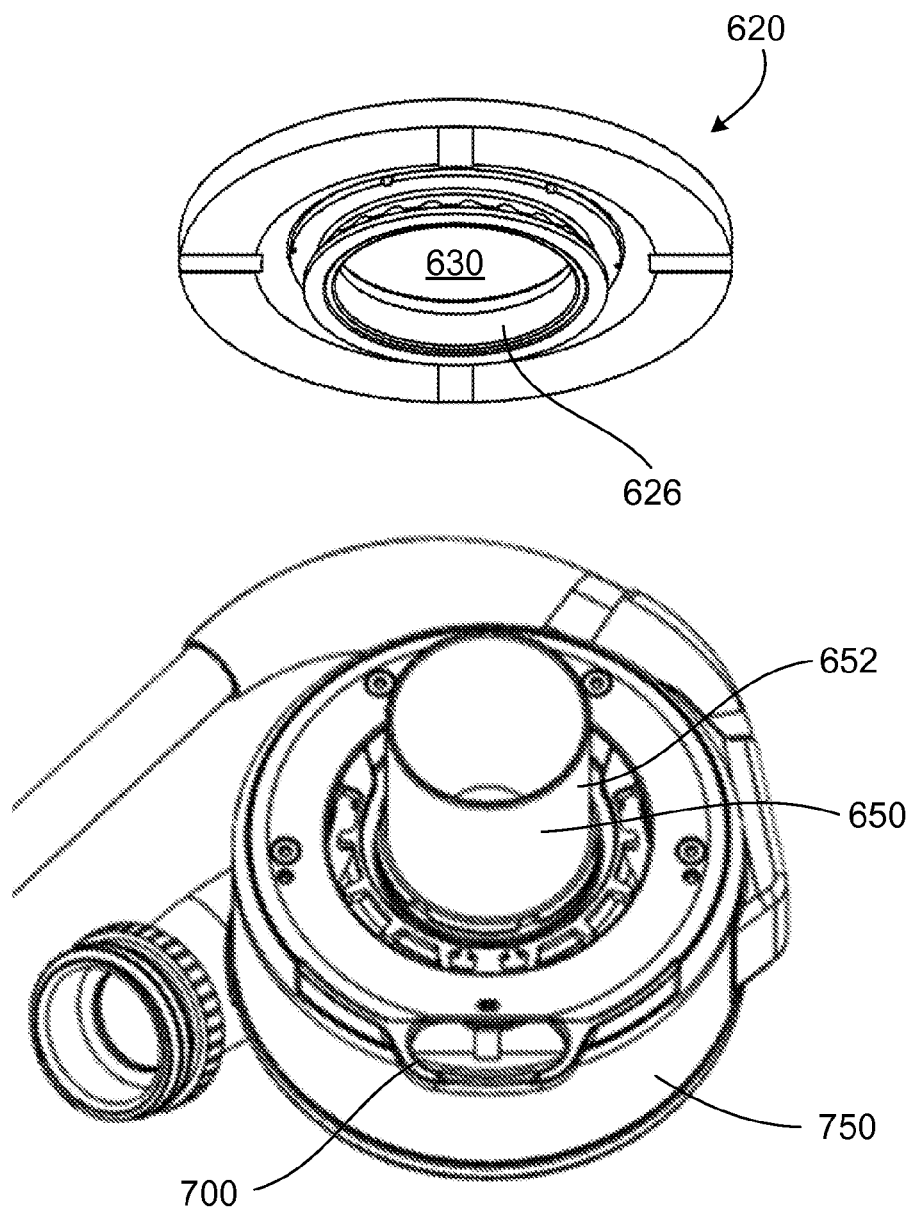
FIG. 21 is a perspective view of a pump, a cannula, and a ventricular cuff.

Referring to FIG. 21, an alternate implementation includes a cuff 620 that couples to a cannula 650 of a pump 750. The cuff 620 defines an opening 630 that admits a proximal portion 652 of the cannula 650. A coupling mechanism in the form of an attachment member 626 engages a sealing ring 802 (FIG. 23B), for example, an o-ring disposed about the cannula 650, to couple the cuff 620 to the cannula 650. A clip 700 (FIG. 25A) acts as a locking mechanism to impede the cuff 620 from becoming uncoupled from the cannula 650.

Like the implementations described above, the cuff 620 can be coupled to the pump 750 with a low profile, for example, in a distance from a heart that is approximately the height of the cuff 620 along the cannula 650. The cuff 620 is coupled to the pump 750 by moving the cannula 650 axially through the cuff 620. The locking mechanism, for example, the clip 700, can then be engaged to secure the position of the cuff 620 about the cannula 650. Similar to the cam 28 and the clip 200, the clip 700 moves into a locked position by moving in a plane perpendicular to a cannula, which facilitates attachment of the cuff 620 to the pump 750 in the low profile.

Figure 22A:
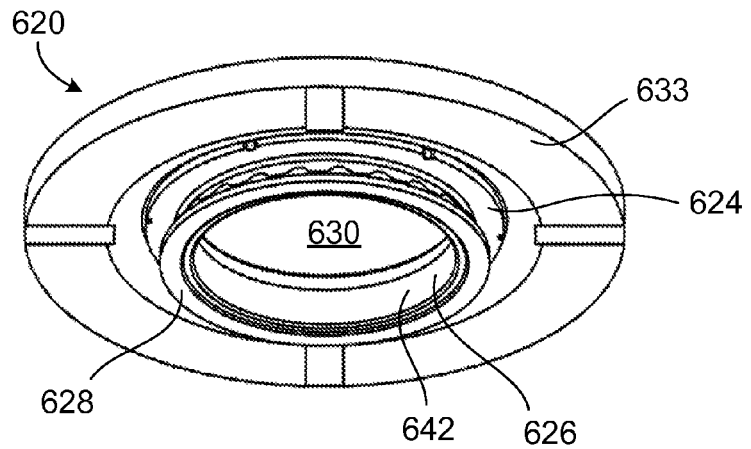
FIG. 22A is a perspective view of the cuff of FIG. 21.
Figure 22B:
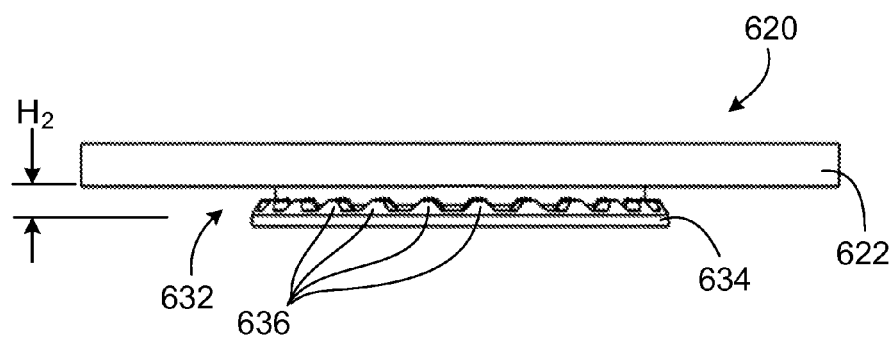
FIG. 22B is a side view of the ventricular cuff of FIG. 21.

Referring to FIGS. 22A and 22B, the cuff 620 includes an annular fastening member 622 that a clinician can fasten to heart tissue. For example, the fastening member 622 can be formed of a fabric such as PTFE felt. The cuff 620 includes a linking member 624 coupled to the fastening member 622, for example, by sutures or direct molding. The linking member 624 is formed of, for example, an elastomer such as silicone. The linking member 624 includes a reinforcement member 625 (FIG. 22D), such as a mesh ring. The linking member 624 couples the attachment member 626 to the fastening member 622, as described below.

The linking member 624 includes a bottom surface 628 that engages a circumferential flange 662 (FIG. 23B) of the cannula 650. The primary sealing mechanism between the cuff 620 and the cannula 650 is the sealing ring 802, and as a result, the linking member 624 need not form a seal about the cannula 650. Nevertheless, in some implementations, the linking member 624 may form a secondary seal through engagement with the circumferential flange 662. In some implementations, the bottom surface 628 engages a surface of the pump 750 as an alternative to, or in addition to, engaging a portion of the cannula 650.

The linking member 624 defines a circumferential groove 632 in the outer diameter of the cuff 620, located between the fastening member 622 and a flanged portion 634 of the linking member 624. The circumferential groove 632 receives a portion of the clip 700 to secure the cuff 620 to the pump 750, as described further below. The linking member 624 includes ridges 636 in the circumferential groove 632, for example, disposed on the flanged portion 634. The ridges 636 are spaced apart and extend approximately halfway along the height, $H_2$, of the circumferential groove 632. When the clip 700 is in a locked position about the cuff 620, the clip 700 engages the ridges 636 to limit rotation of the cuff 620 about the cannula 650.

Figure 22C:
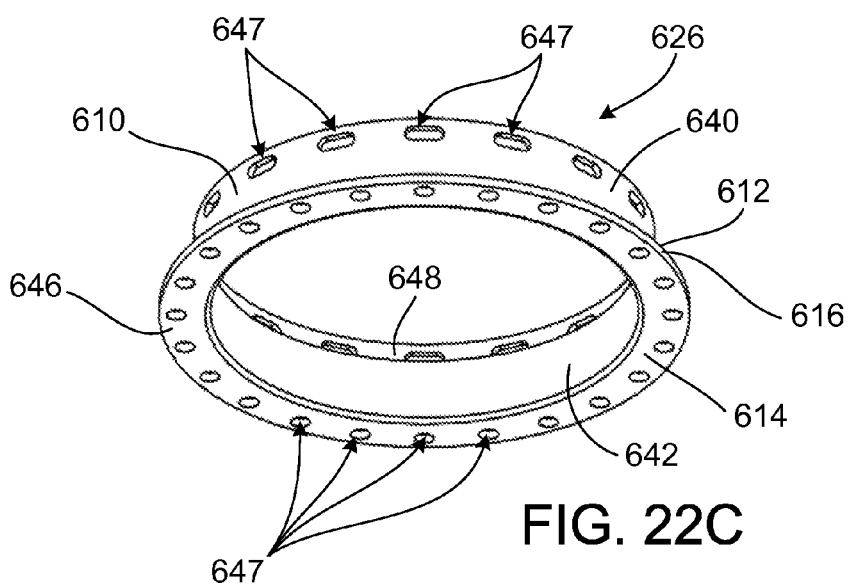
FIG. 22C is a perspective view of an attachment member of the ventricular cuff of FIG. 21.

Referring to FIG. 22C, the attachment member 626 is formed of, for example, a rigid material such as metal or PEEK. The attachment member 626 includes a cylindrical portion 640 that has an outer wall 644 and an inner surface 642 that engages the sealing ring 802. The attachment member 626 includes a flanged portion 646, for example, a circumferential flange that extends in a plane generally perpendicular to the outer wall 644.

Figure 22D:
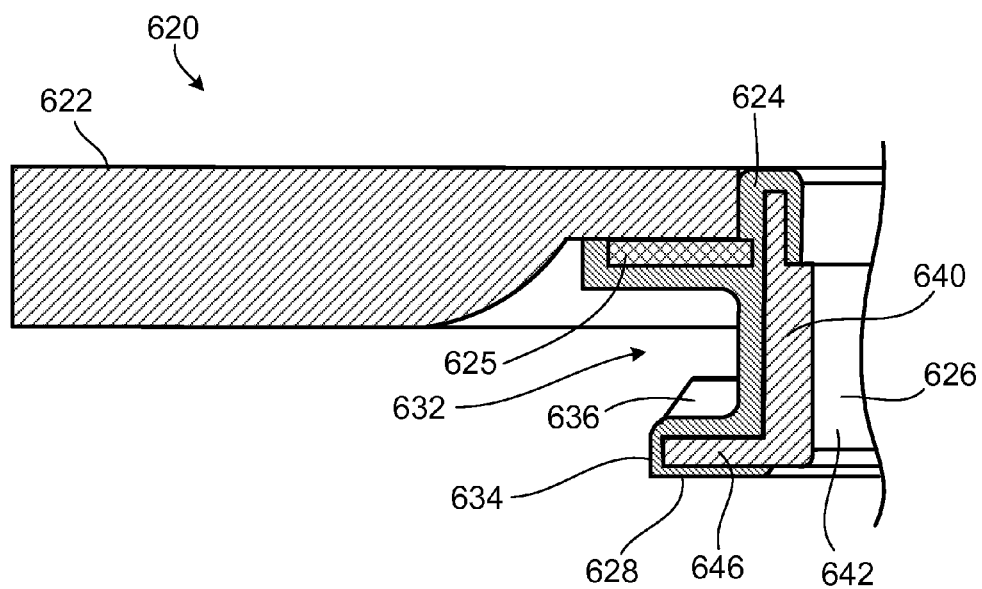
FIG. 22D is a side cutaway view of the ventricular cuff of FIG. 21.

Referring to FIG. 22D, the linking member 624 is molded over the attachment member 626. The flanged portion 646 and the cylindrical portion 640 define holes 647 that admit material of the linking member 624. The material of the linking member 624 that extends through the holes 647 forms mechanical locks that couple the linking member 624 to the attachment member 626. The linking member 624 is molded over an inner circumferential wall 648, which can have a larger inner diameter than the rest of the cylindrical portion 640. The linking member 624 is also molded over an outer circumferential surface 610 of the cylindrical portion 640, as well as a top surface 612, a bottom surface 614, and a circumferential side surface 616 of the flanged portion 646. The inner surface 642 of the attachment member 626 remains exposed.

Figure 23A:
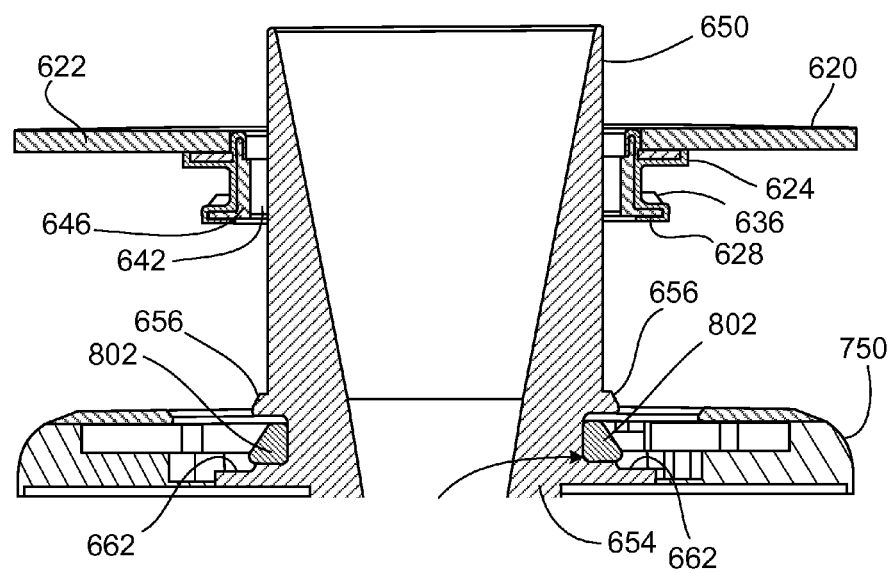
FIGS. 23A and 23B are side cutaway views of the cannula and ventricular cuff of FIG. 21.
Figure 23B:
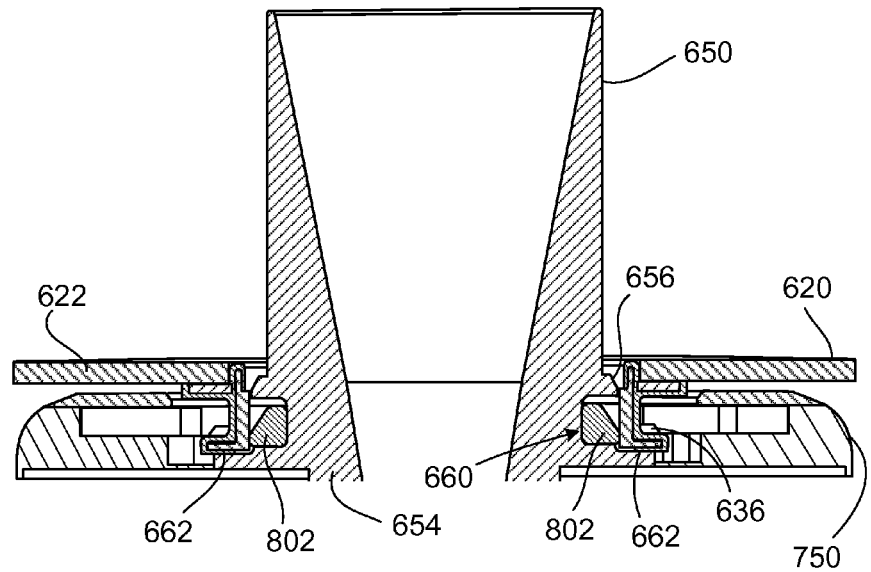

Referring to FIGS. 23A and 23B, the cannula 650 includes the proximal portion 652, the circumferential flange 662, and a distal portion 654 housed within the pump 750. The cannula 650 includes a circumferential taper 656 that engages the attachment member 626, guiding the cuff 620 into alignment with the cannula 650. The cannula 650 defines a circumferential groove 660 between a first circumferential ridge 658 and a second circumferential ridge 659. The sealing ring 802 is disposed in the circumferential groove 660 and is formed of, for example, an elastomer such as silicone or implantable-grade EPDM.

To couple the cannula 650 to the cuff 620, the clinician moves the proximal portion 652 through the opening 630 of the cuff 620 (FIG. 23A). As the cannula 650 advances further, the sealing ring 802 engages the inner surface 642 of the attachment member 626, compressing the sealing ring 802 into the circumferential groove 660 (FIG. 23B). The engagement of the sealing ring 802 with the inner surface 642 and the engagement of the bottom surface 628 with the circumferential flange 662 provide tactile feedback to the clinician that the appropriate position has been achieved.

The engagement of the sealing ring 802 between the cuff 620 and the cannula 650 limits travel of the cannula 650 relative to the cuff 620, coupling the cannula 650 to the cuff 620. The compression of the sealing ring 802 between the cuff 620 and the cannula 650 also creates a hemostatic seal between the cannula 650 and the cuff 620. From the position shown in FIG. 23B, the clinician can move the clip 700 into a locked position about the cuff 620 to secure the cuff 620 about the cannula 650, as described further below.

Figure 24A:
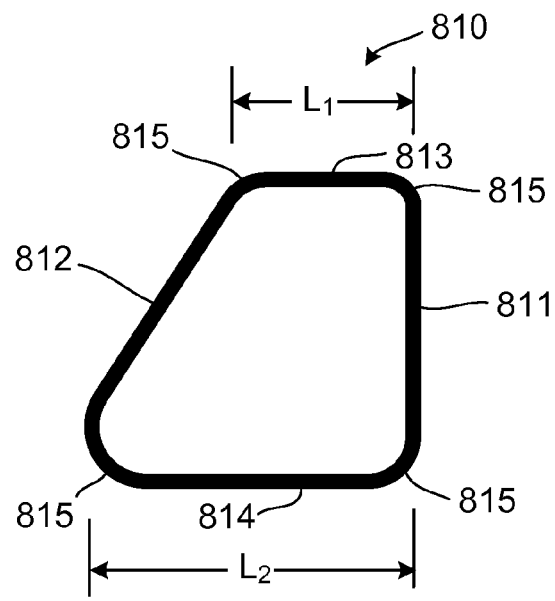
FIGS. 24A and 24B are cross-sectional view of sealing rings.

Referring to FIG. 24A, the sealing ring 802 has a cross-section 810 that is substantially trapezoidal. The force required to insert the cannula 650 into the cuff 620 using the sealing ring 802 is typically smaller than the force required to insert the cannula 650 using a sealing ring that has a round cross-section and a similar cross-sectional width. In some instances, a lower insertion force is desirable to facilitate installation of the cannula 650 relative to the implanted cuff 620.

The cross-section 810 has an inner side 811, and outer side 812, a top side 813, and a bottom side 814. Adjacent sides 811, 812, 813, 814 are connected by rounded corners 815. The inner side 811 faces toward the cannula 650 and is substantially flat. As a result, the inner surface of the sealing ring 810 is substantially cylindrical. The top side 813 faces away from the pump 750, and the bottom side 814 faces toward the pump 750. The top side 813 and the bottom side 814 are substantially parallel to each other, for example, both sides 813, 814 are substantially perpendicular to the inner side 811.

The top side 813 and the bottom side 814 have different lengths. The length, $L_1$, of the top side 813 can be, for example, between one-fourth and three-fourths of the length, $L_2$, of the bottom side 814. For example, the length, $L_1$, of the top side 813 can be approximately half or approximately two-thirds of the length, $L_2$, of the bottom side 814. The outer side 812 is angled, for example, forming substantially straight angled edge.

Figure 24B:
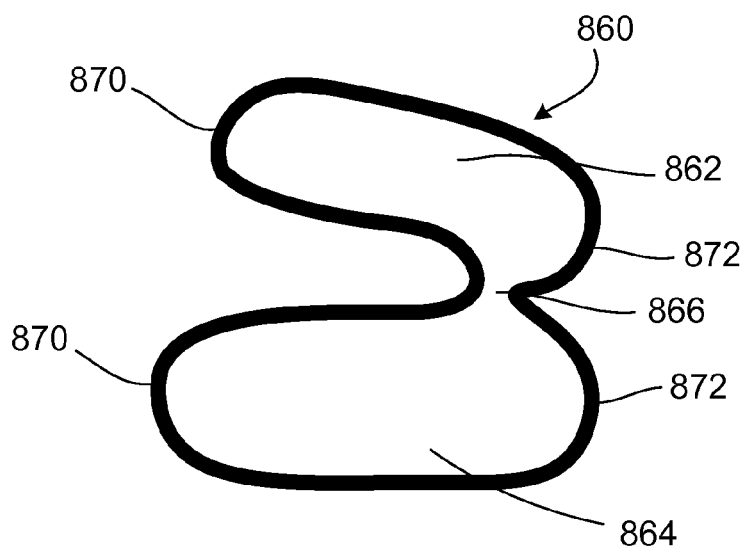

Referring to FIG. 24B an alternative sealing ring has a cross-section 860. The cross-section 860 includes an upper portion 862 and a lower portion 864, connected by a narrow neck 866. The sealing ring 850 thus includes two stacked discs, connected by an annular band. The cross-section 860 includes outer sides 870 engage the inner surface 642 of the cuff 620, and inner sides 872 that engage the cannula 650 in the circumferential groove 660.

Figure 25A:
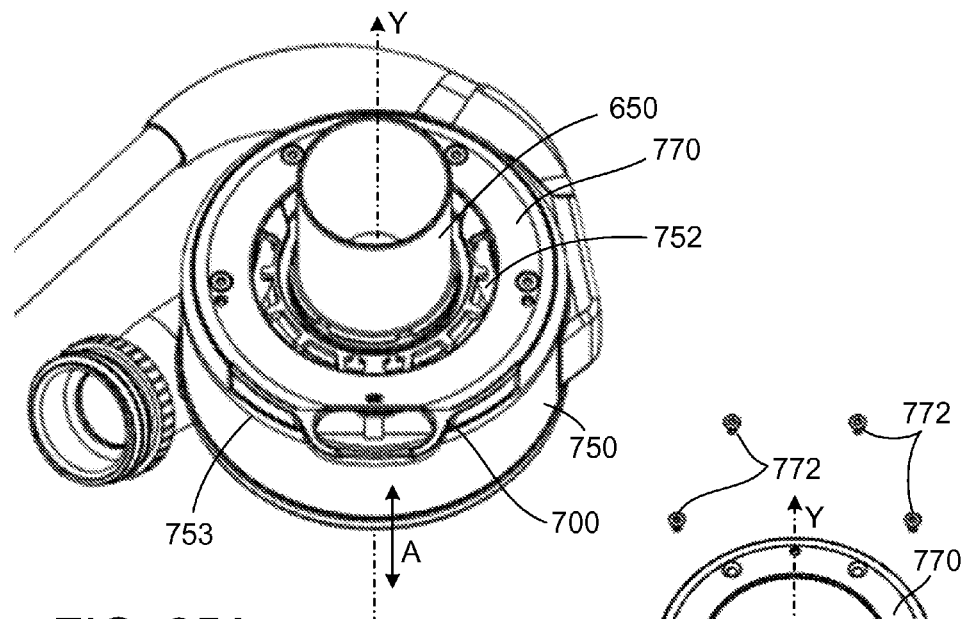
FIG. 25A is a perspective view of the pump of FIG. 21.
Figure 25B:
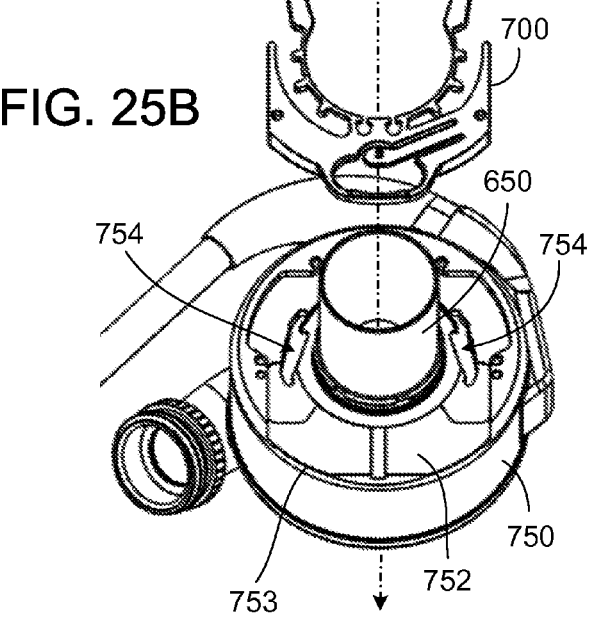
FIG. 25B is an exploded view of the pump of FIG. 21.

Referring to FIGS. 25A and 25B, the clip 700 cooperates with features of the pump 750, described below, to limit movement of the cuff 620 (not shown) relative to the cannula 650. The clip 700 has an unlocked position, in which the cuff 620 can be coupled about the cannula 650. The clip 700 also has a locked position, in which the clip 700 secures the cuff 620 relative to the cannula 650. A component, such as a motor housing 753 or an element attached to the motor housing 753, provides an upper surface 752 that defines channels 754. The clip 700 includes arms 714 that extend into the channels 754 and travel along the channels 754 as the clip 700 moves into its locked position.

The pump 750 captures the clip 700 between the upper surface 752 and a cover 770. The cover 770 is attached over the upper surface 752 by, for example, screws 772 or welds. The upper surface 752 and the cover 770 define a slot 740 for the clip 700 to travel within. The slot 740 permits the clip 700 to travel in a plane, for example, to travel in a linear direction, A, in a plane perpendicular to a longitudinal axis, Y, of the cannula 650.

Figure 26A:
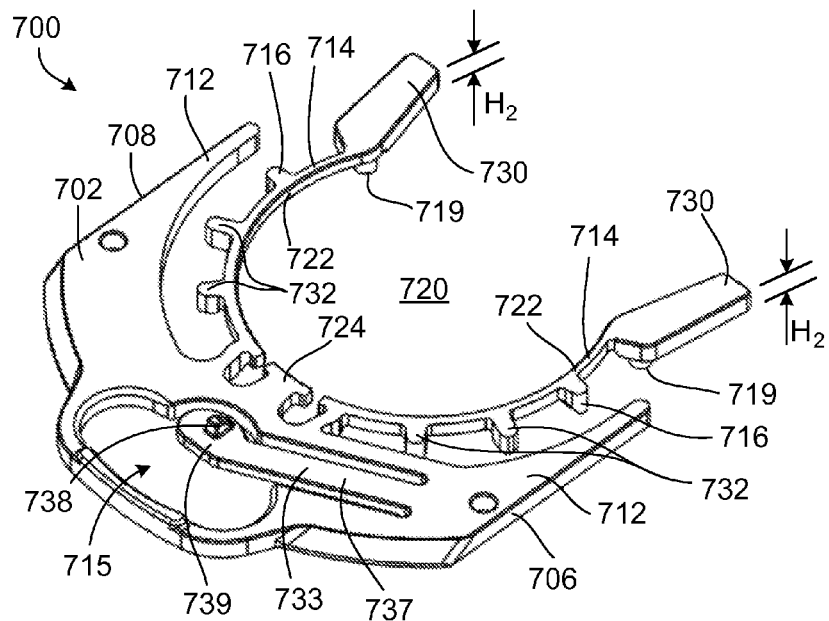
FIG. 26A is a top perspective view of a clip that cooperates with the pump and the ventricular cuff of FIG. 21.
Figure 26B:
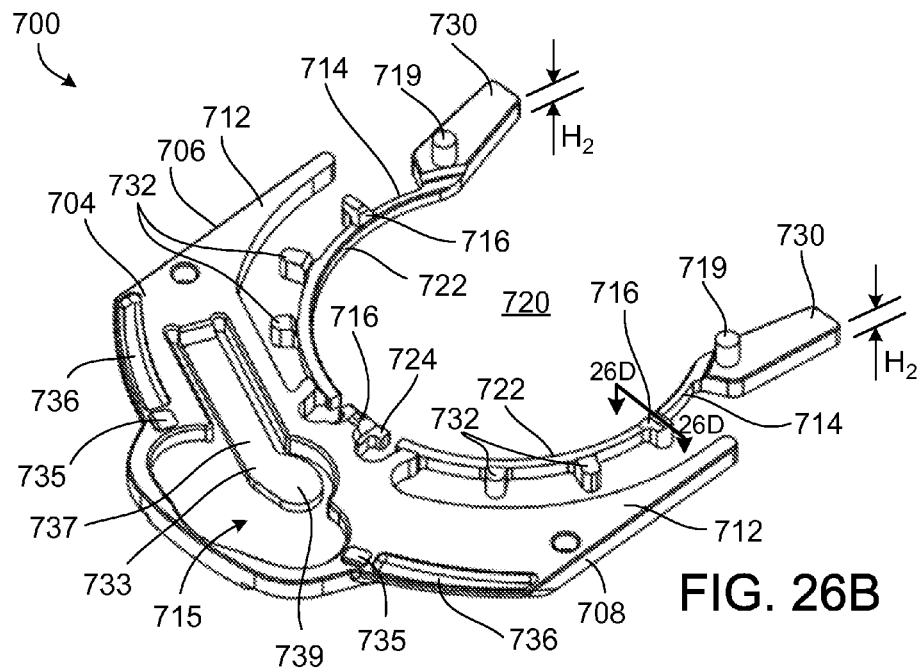
FIG. 26B is a bottom perspective view of the clip of FIG. 26A.
Figure 26C:
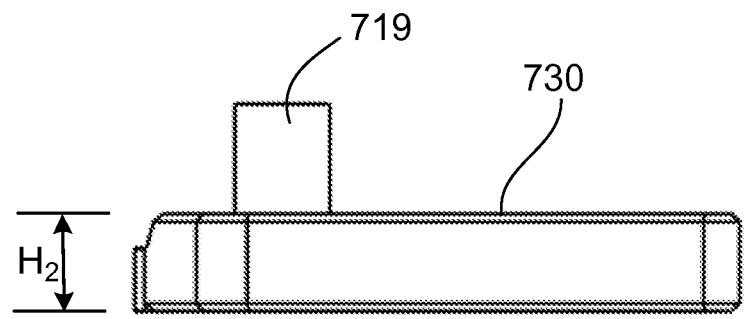
FIG. 26C is a side view of an end portion of an arm of the clip of FIG. 26A.

Referring to FIGS. 26A-26C, the clip 700 includes a top side 702 that faces the cover 770, a bottom side 704 that faces the upper surface 752, and opposite lateral sides 706, 708. The clip 700 can be formed of, for example, metal, such as titanium, or a rigid plastic, such as PEEK. The clip 700 includes guide rails 712 and defines a recess or opening 715. The guide rails 712 stabilize the clip 700 laterally and guide the clip 700 through a linear motion in the slot 740. The opening 715 admits a tool or a finger of the clinician to facilitate refraction of the clip 700.

The arms 714 of the clip 700 are curved and define an opening 720. The arms 714 are resilient and can deflect laterally to capture the cuff 620. Each arm 714 includes a post 719 that extends from the bottom side 704 of the clip 700. Each post 719 is received in one of the channels 754 (FIG. 25B) defined in the upper surface 752. The posts 719 are substantially cylindrical and extend perpendicular to, for example, a plane defined along the top side 702 of the clip 700. When the clip 700 is located in the slot 740, the posts 719 extend substantially parallel to the longitudinal axis, Y, of the cannula 650. As the clip 700 moves relative to the pump 750, the posts 719 travel through the channels 754.

In the locked position of the clip 700, the arms 714 extend about the cuff 620 and extend into the circumferential groove 632. The arms 714 have a substantially smooth inner surface 722 that engages the linking member 624 in the circumferential groove 632. The arms 714 also include teeth 716 (FIG. 26B) that fit between the ridges 636 to limit rotation of the cuff 620 relative to the clip 700. The teeth 716 can be disposed on the arms 714 and on a central extension 724 of the clip 700. Three teeth 716 are shown, positioned to press radially inward on the cuff 620 when the clip 700 is in its locked position. More teeth or fewer than three teeth can be used to promote rotational stability of the cuff 620.

Figure 26D:
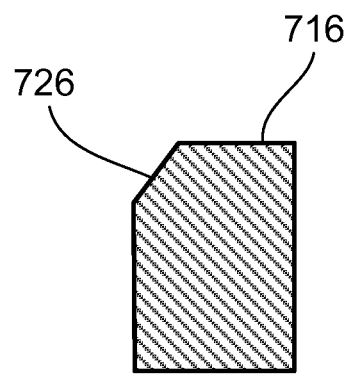
FIG. 26D is a side cross-sectional view of a tooth of the clip of FIG. 26A.

The teeth 716 have an angled or chamfered edge 726 (FIG. 26D), permitting the teeth 716 to engage the cuff 620 when the cuff 620 is not fully seated against the circumferential flange 662. As the clip 700 moves into its locked position, the teeth 716 move radially inward toward the circumferential groove 632. The chamfered edge 726 engages the flanged portion 634 of the cuff 620, forcing the cuff 620 toward the upper surface 752 into a fully seated position against the circumferential groove 662.

The clip 700 includes substantially flat end portions 730 that are captured between the upper surface 752 and the cover 770. The cover 770 impedes the end portions 730 from moving away from the surface 752, and thus holds the posts 719 in the channels 754. Engagement of the end portions 730 between the upper surface 752 and the cover 770 also limits twisting along the arms 714 in response to axial loads exerted along the arms 714. The end portions 730, the teeth 716, and stabilizing posts 732 on the arms 714 can each have a height, $H_2$, along the longitudinal axis, Y, that is substantially the same as a corresponding height of the slot 740, thereby limiting travel of the clip 700 along the longitudinal axis and limiting tilting of the clip 700 within the slot 740.

The clip 700 includes a latch 733 that engages the cover 770 to limit retraction of the clip 700 from the locked position. The latch 733 includes a deflection beam 737 and an extension 738 located on a free end 739 of the deflection beam 737. The extension 738 extends from the top side 702 of the clip 700. The deflection beam 737 provides a resilient force that holds the extension 738 in a mating receptacle of, for example, the cover 770, unless overcome by a sufficient force.

The clip 700 includes ramp features 735 that extend from the bottom side 704. The ramp features 735 wedge the clip 700 between the cover 770 and the upper surface 752, stabilizing the clip 700 along the longitudinal axis, Y, of the cannula 650 when the clip 700 is in the locked position. By forcing the top side 702 toward the cover 770, the ramp features 735 also force engagement of the latch 733 to the mating receptacle.

The clip 700 includes visual indicators 736 on the bottom side 704 that indicate when the clip 700 is out of the locked position. The visual indicators 736 are, for example, recesses containing a colored material that is easily noticeable by a clinician. The visual indicators 736 are exposed, and thus visible from the bottom of the pump 750, when the clip 700 is not in the locked position. The visual indicators 736 are obscured when the clip 700 is in the locked position.

Figure 27:
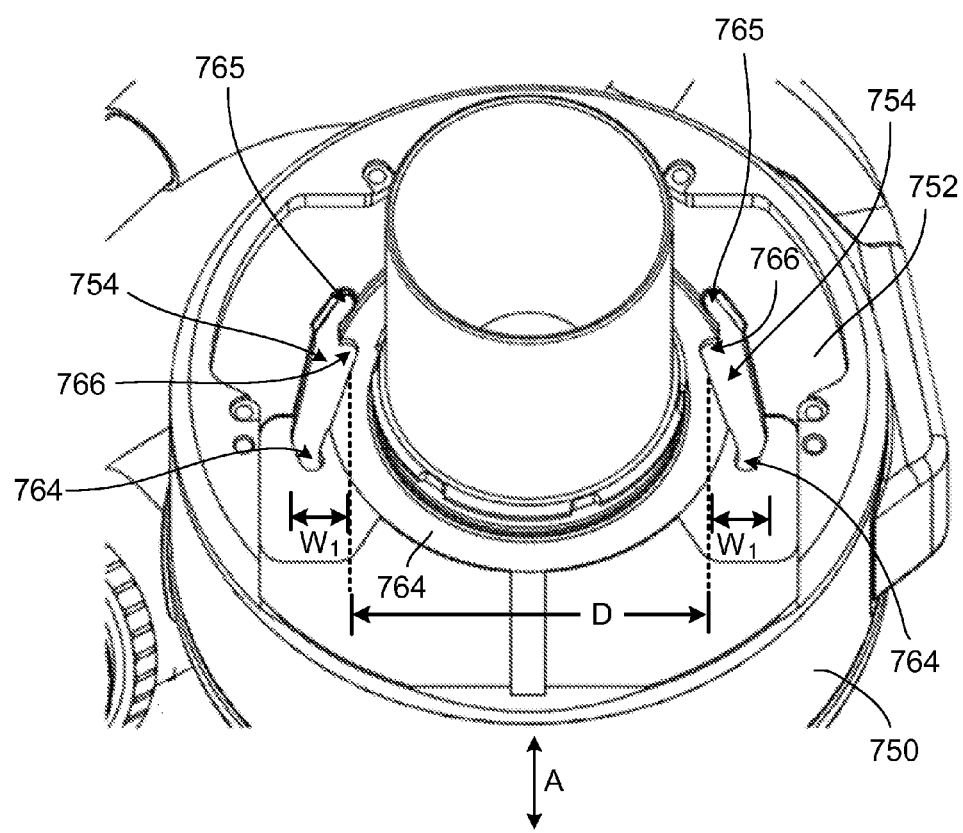
FIG. 27 is a perspective view of a surface of the pump of FIG. 21.

Referring to FIG. 27, the channels 754 in the surface 752 direct travel of the arms 714 as the clip 700 moves in the slot 740. As the clip 700 moves between an unlocked position to the locked position, the posts 719 move through the channels 754. The channels 754 have a width, $W_2$, that is larger than a diameter of the posts 719, which permits different lateral positions of the posts 719 in the channels 754. As described further below, the width, $W_2$, permits the posts 719 travel along different paths in the channels 754, rather than being constrained to travel along a single path.

The channels 754 are defined by inner walls 760 and outer walls 762. A lateral distance, D, between the inner walls 760 is greater than a distance between the posts 719 when the arms 714 are not flexed. As a result, positioning the posts 719 in the channels 754 flexes the arms 714 away from each other, causing the arms 714 to exert a resilient inward force against the inner walls 760. As the clip 700 travels in the slot 740, the posts 719 slide along the inner walls 760 unless displaced by, for example, the cuff 620.

The channels 754 define features that receive the posts 719. Each channel 754 defines, for example, a first end 764, a second end 765, and a detent 766, each of which can receive one of the posts 719. The posts 719 reside in the first ends 764 in an unlocked position of the clip 700, for example, when the clip 700 is fully retracted. At the first ends 764, the posts 719 engage the walls to impede the clip 700 from separating from the pump 750 by sliding out of the slot 740 along arrow A. The posts 719 reside in the second ends 765 when the clip 700 is in the locked position. The posts 719 reside in the detents 766 when the clip 700 is in a restrained position, for example, in which engagement of the posts 719 in the detents 766 impedes the clip 700 from travelling further toward the locked position. The unlocked position, the locked position, and the restrained position are stable positions of the clip 700 within the slot 740.

Figure 28A:
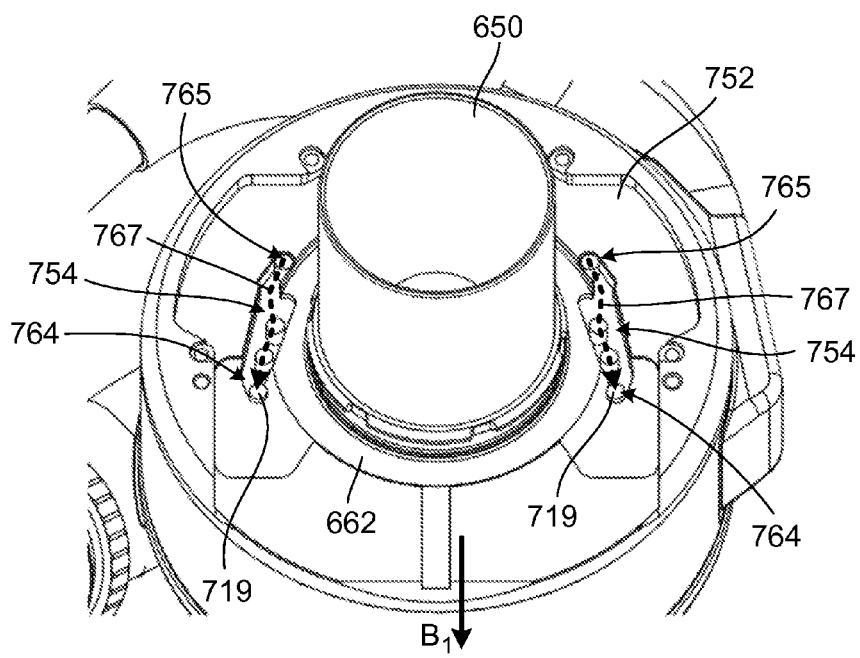
FIGS. 28A to 28C are perspective views illustrating different motions of the clip of FIG. 26A relative to the pump of FIG. 21.

Referring to FIG. 28A, the clip 700 is retracted in the direction of arrow $B_1$, and each post 719 travels along a path 767 between the second end 765 and the first end 764. Various positions of the posts 719 are shown, but other features of the clip 700 are not shown. The pump 750 can be provided to a clinician with the clip 700 in the locked position, with the posts 719 residing in the second ends 765. In some implementations, the arms 714 are in a relaxed state in the locked position. The clinician retracts the clip 700 to permit the cannula 650 to be coupled to the cuff 620.

Figure 28B:
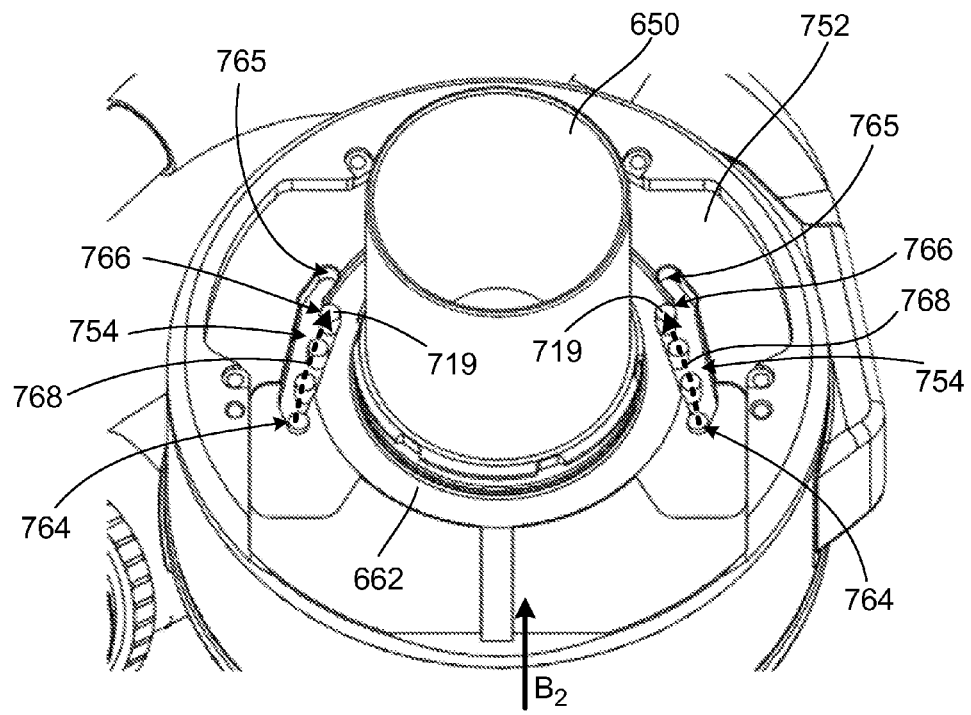

Referring to FIG. 28B, when the cuff 620 is not coupled about the cannula 650, advancing the clip 700 from the unlocked position toward the locked position places the clip 700 in the restrained position. As the clip 700 advances in the direction of arrow $B_2$, the arms 714 exert a lateral force inward toward the cannula 650, causing the posts 719 to travel in a path 768 along the inner walls 760. The posts 719 enter the detents 766 to impede the clip 700 from entering the locked position.

The clip 700 enters the restrained position when the cuff 620 is not properly coupled to the cannula 650, for example, when the cuff 620 is not located about the cannula 650 or the cuff 620 is improperly placed about the cannula 650. The placement of the clip 700 in the restrained discourages premature locking of the clip 700 and indicates to the clinician that the cuff 620 is not properly placed about the cannula 650. Patient safety is enhanced because the clip 700 does not enter the locked position if doing so would not actually secure the cuff 620 to the pump 750.

In some implementations, the clip 700 can enter the restrained position when only one of the posts 719 engages one of the detents 766. Either post 719 can independently impede the clip 700 from entering the locked position. In some instances, the cuff 620 may be seated only partially against the circumferential flange 662. For example, the cuff 620 may be placed in a tilted orientation such that the cuff 620 is not aligned in a plane perpendicular to the cannula 650. With the cuff 620 partially seated, one of the posts 719 may avoid the detent 766. Engagement of the other post 719 with its corresponding detent 766, however, will place the clip 700 in the restrained position rather than permitting the clip 700 to enter the locked position.

Figure 28C:
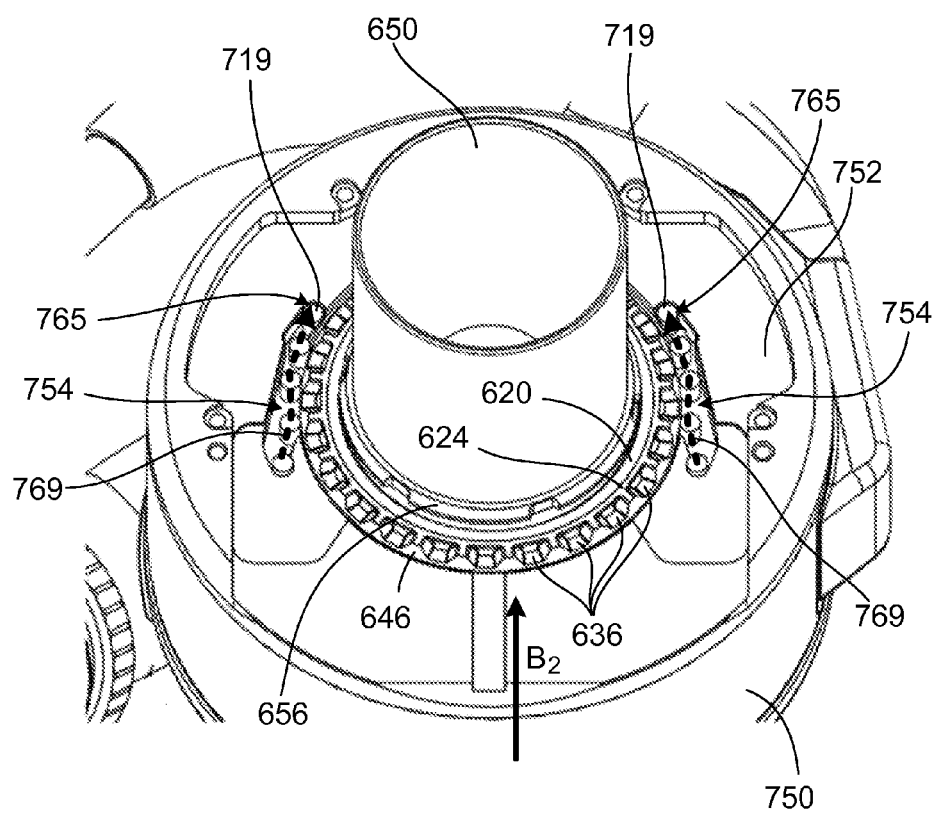

Referring to FIG. 28C, when the cuff 620 is properly coupled to the cannula 650, advancing the clip 700 in the direction of arrow $B_2$ moves the clip 700 into the locked position about the cuff 620. For clarity in illustration, the fastening member 622 and portions of the linking member 624 are not shown.

When the cuff 620 is coupled to the cannula 650, the flanged portions 634, 646 of the cuff 620 cover the detents 766. The cuff 620 blocks the posts 719 from entering the detents 766 and permits the posts 719 to enter the second ends 765. Between the unlocked position and the locked position, the posts 719 move along a path 769. The posts 719 slide along the outer circumference of the flanged portion 646, engaged to the cuff 620 by the resilient force of the arms 714, until the posts 719 reach the second ends 765. In the locked position, the arms 714 (not shown) extend into the circumferential groove 632, capturing the flanged portions 634, 646 between the arms 714 and the circumferential flange 662 of the cannula 650. The teeth 716 extend radially inward into the circumferential groove 632, becoming enmeshed between the ridges 636 to limit rotation of the cuff 620 relative to the cannula 650.

Figure 29A:
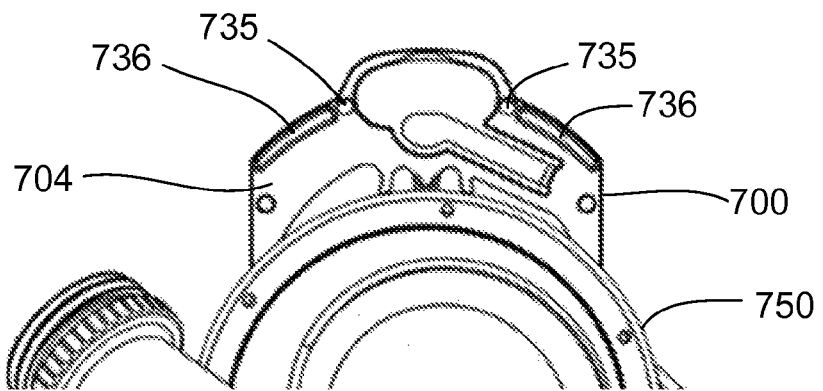
FIGS. 29A to 29C are bottom views of different positions of the clip of FIG. 26A relative to the pump of FIG. 21.
Figure 29B:
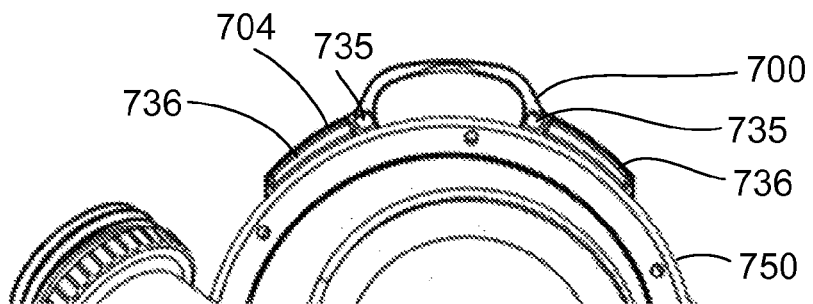

Referring to FIGS. 29A and 29B, when a clinician installs the pump 750, the visual indicators 736 on the clip 700 are exposed to the clinician's view. The visual indicators 736 indicate that the clip 700 is not securing the cuff 620, and thus that installation is incomplete. The visual indicators 736 are exposed in the unlocked position (FIG. 29A) and in the restrained position (FIG. 29B).

Figure 29C:
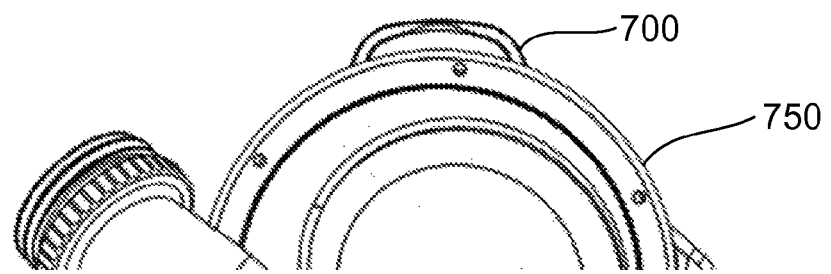

Referring to FIG. 29C, when the clip 700 enters the locked position, the pump 750 obscures the visual indicators 736, indicating to the clinician that the clip 700 has been properly locked about the cuff 620.

Figure 30A:
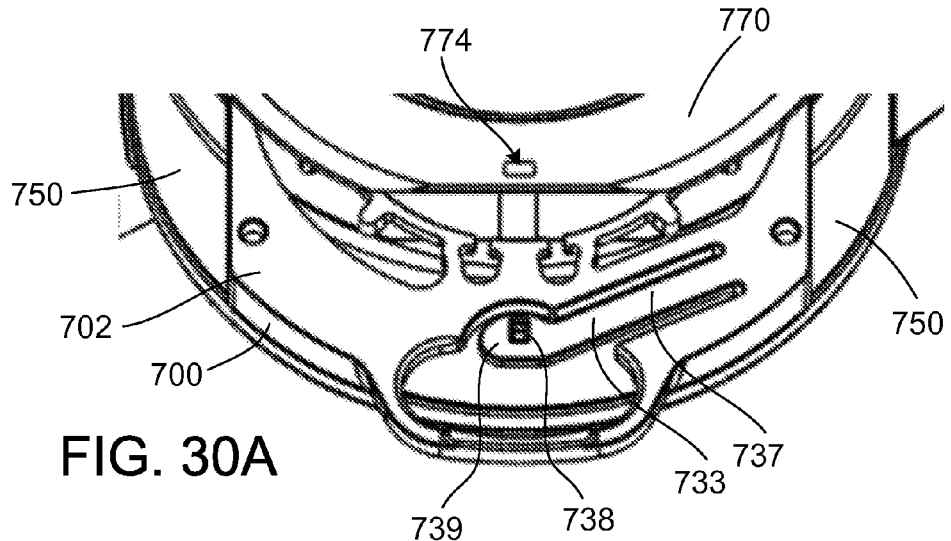
FIGS. 30A to 30C are top perspective views of different positions of the clip of FIG. 26A relative to the pump of FIG. 21.
Figure 30B:
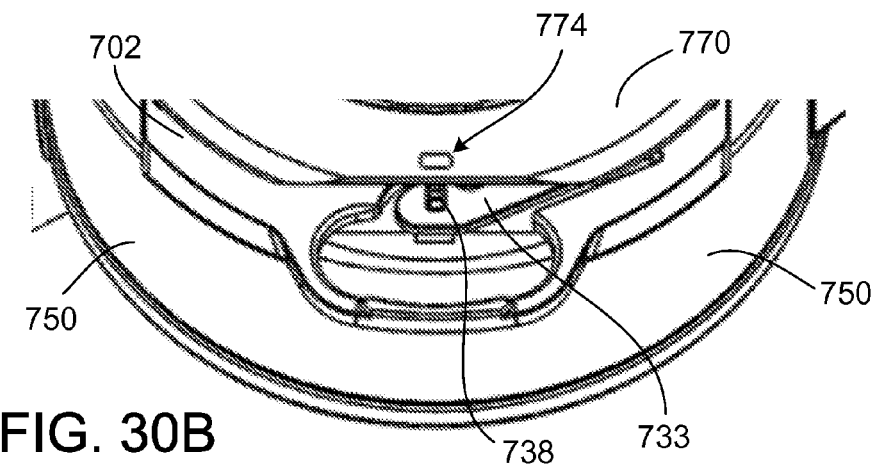
Figure 30C:
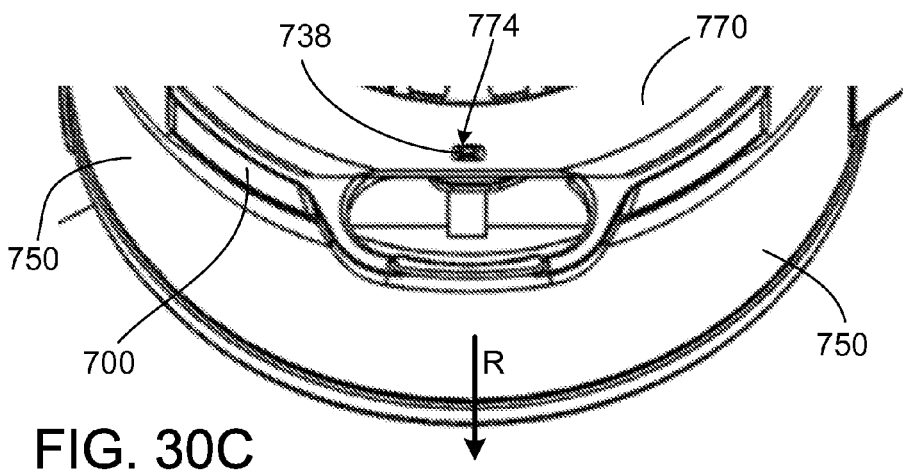

Referring to FIGS. 30A-30C, the cover 770 defines a mating receptacle 774, for example, a recess or an opening, that cooperates with the latch 733. The latch 733 does not secure the position of the clip 700 in the unlocked position (FIG. 30A) or the restrained position (FIG. 30B). In the locked position (FIG. 30C), the extension 738 extends into the mating receptacle 774 to impede retraction of the clip 700 in the direction of the arrow R.

Figure 31:
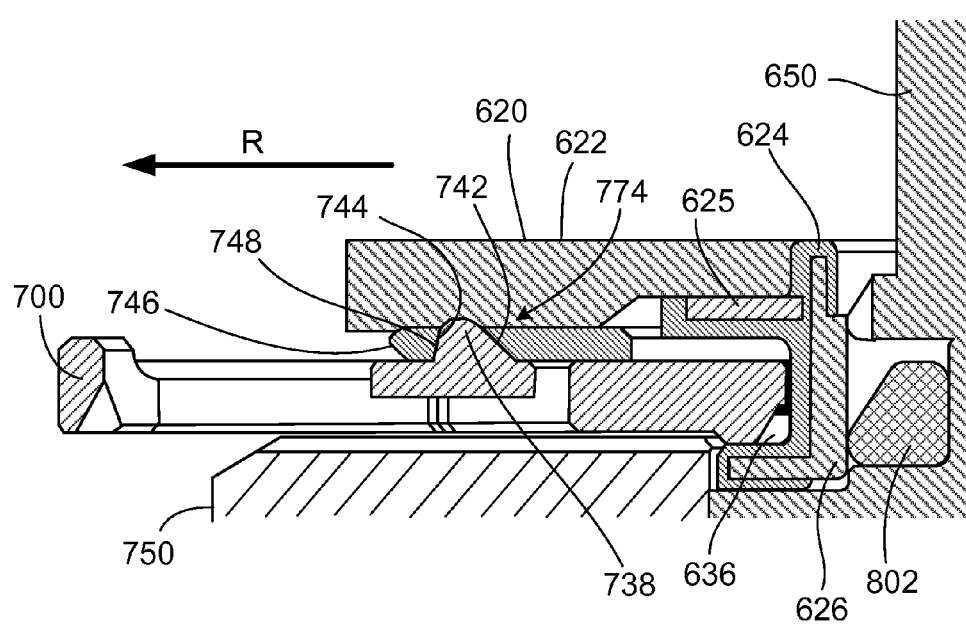
FIG. 31 is a side cutaway view of the pump, the cannula, and the ventricular cuff of FIG. 21.

Referring to FIG. 31, the extension 738 includes an angled leading edge 742 and an angled trailing edge 744 that engage the cover 770. The leading edge 742 engages an outer edge 746 of the cover 770 as the clip 700 travels into the locked position. The engagement of the leading edge 742 with the outer edge 746 deflects the deflection beam 737, permitting the extension 738 to slide under the outer edge 746 and into the mating receptacle 774. The trailing edge 744 engages an inner surface 748 of the mating receptacle 774 to limit removal of the clip 700.

The trailing edge 742 has a steeper slope than the leading edge 742. For example, the trailing edge 742 can have a slope of between approximately 70 degrees and approximately 85 degrees, and the leading edge can have a slope of between approximately 10 degrees to approximately 60 degrees. As a result, the amount of force required to dislodge the extension 738 from the mating receptacle 774 is greater than the force required to insert the extension into the mating receptacle 774. When removal of the clip 700 is desired, a clinician can engage a tool with the deflection beam 737 to move the extension 738 out of the mating receptacle 774, which permits the clip 700 to be refracted.

In some implementations, a plug can be fabricated for a cuff 20, 120, 320, 620. A plug can be placed in the opening 30, 130, 330, 630 of an implanted cuff 20, 120, 320, 620 after a pump 12, 250, 750 has been explanted. The plug can fill the opening 30, 130, 330, 630 to prevent blood from escaping through the cuff 20, 120, 320, 620 after the pump 12, 250, 750 is removed. Plugs can include features similar to those described for the cannulas 50, 150, 350, 650. As a result, a plug can be coupled to a corresponding cuff 20, 120, 320, 620 using one or more of the same mechanisms that couple a cuff 20, 120, 320, 620 to a cannula 50, 150, 350, 650. A plug can be further secured to a heart or to a cuff 20, 120, 320, 620 by sutures. A plug may further be configured to fill the opening through any of the further cuffs described below.

Figure 32:
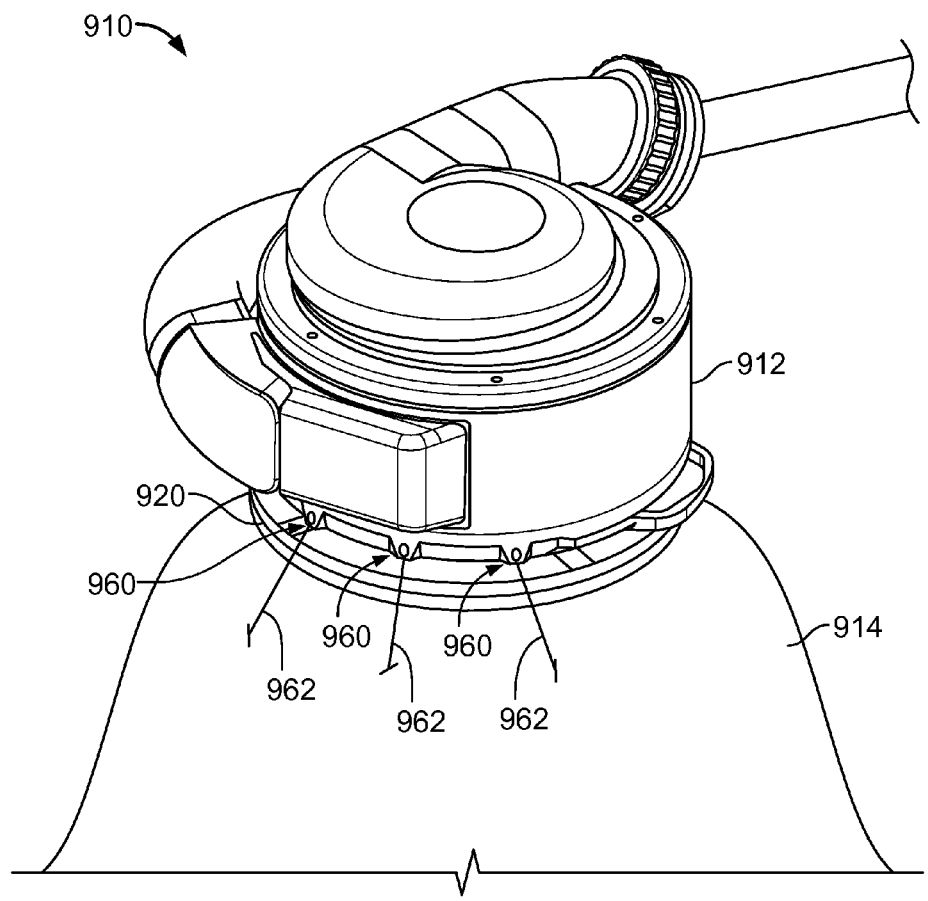
FIG. 32 is a perspective view of a pump installed at a heart.
Figure 33:
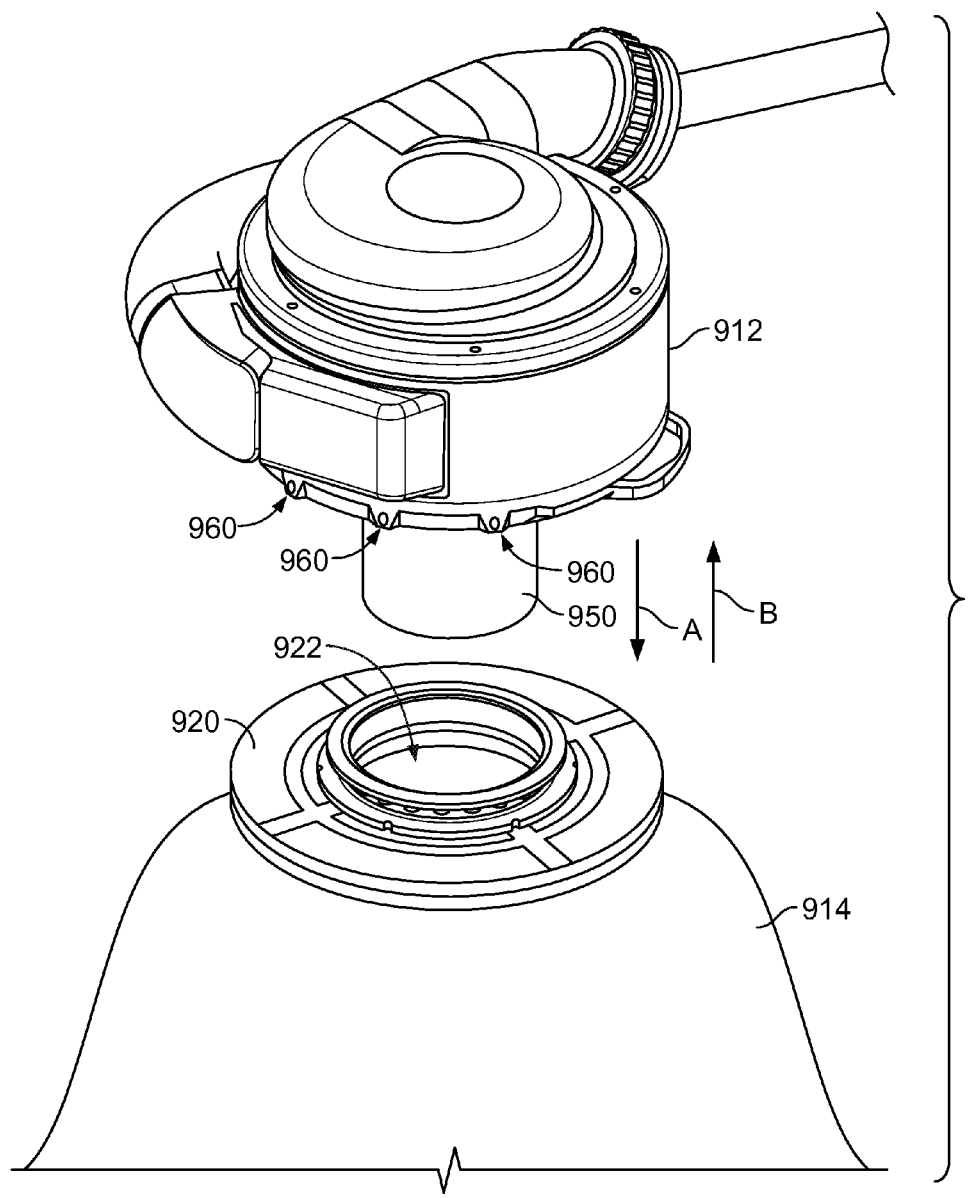
FIG. 33 is a perspective view of the pump of FIG. 32 and a cuff attached to the heart.

Referring to FIGS. 32 and 33, a ventricular assist system 910 for treating, for example, a patient with a weakened left ventricle, includes a blood pump 912 that receives blood from a patient's heart 914. The pump 912 is coupled to a cuff 920, which in turn is attached to the heart 914. The cuff 920 is attached to the heart 914 by, for example, sutures that attach a portion of the cuff 920 to the apex of the left ventricle of the heart 914. The pump 912 receives blood from the heart through an inflow cannula 950 (FIG. 33) of the pump 912 disposed through an opening 922 (FIG. 33) in the cuff 920.

The ventricular assist system 910 may be implanted in the thoracic cavity of a patient. After implantation, the cuff 920 limits the risk of inflow cannula malposition due to potential post-operative pump migration. Inflow cannula malposition is an adverse clinical event that may reduce pump performance and endanger the patient. The cuff 920 helps maintain a space around the inflow cannula 950 so that the inflow cannula 950 does not become partially or completely occluded by surfaces of the heart (e.g., by the septal wall of the heart). For example, the cuff 920 is sufficiently stiff to promote flattening of the myocardium when the sewing ring is attached to the heart 914. In other words, after installation of the cuff 920, the rigidity or resilience of the cuff 920 reshapes the myocardium in a manner that the geometry of the myocardium in the region of the cuff 920 is flatter than the natural or previous geometry of the myocardium. The cuff 920 can exert a resilient force that resists bending of the cuff 920 and flattens an area of the myocardium in contact with the cuff 920.

The cuff 920 also aids installation of the pump 912. Exemplary cuff 920 is relatively rigid and has a higher bending resistance to bending than conventional ventricular cuffs. The relatively increased stiffness of the cuff 920 permits a clinician to hold the cuff 920 (e.g., at outer edges of the cuff 920) and apply counter-pressure with the cuff 920 against the inflow cannula 950 during installation of the pump 912.

The pump 912 includes anchors 960, such as eyelets or other openings defined in the housing 964, where sutures 962 or other fasteners can attach to the pump 912. The sutures 962 secure the pump 912 to, for example, the cuff 920, the myocardium of the heart 914, ribs of the patient, or other structures. The sutures 962 limit rotation of the pump 912 relative to the heart 914 and other movement of the pump 912 relative to the heart 914. Securing the pump 912 using the anchors 960 and flattening the myocardium in the region of the pump 912 help limit the risk of inflow cannula malposition, as discussed further below.

Figure 34A:
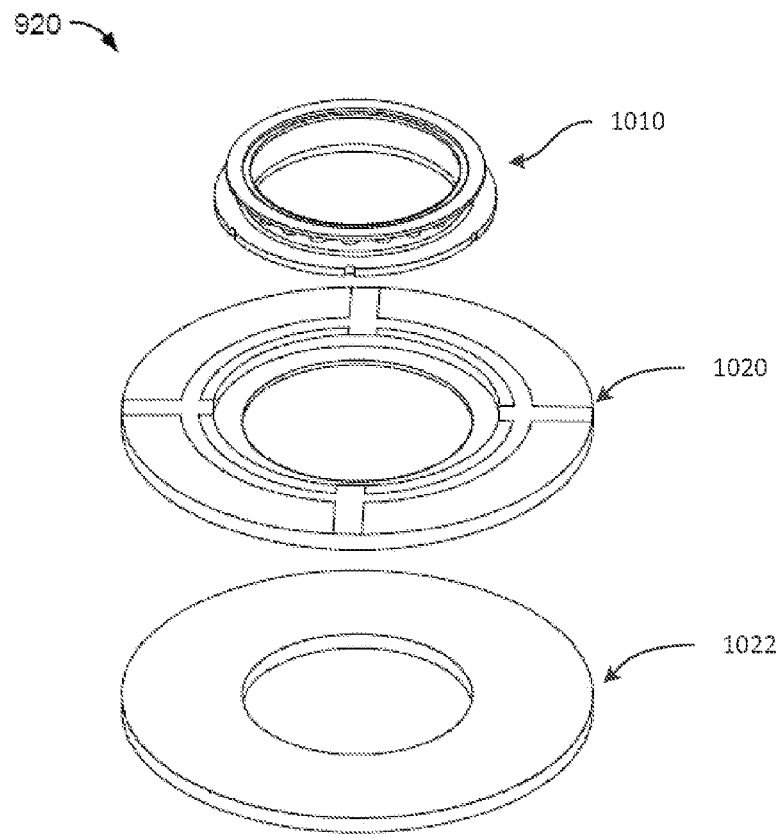
FIG. 34A is an exploded view of the cuff of FIG. 33.
Figure 34B:
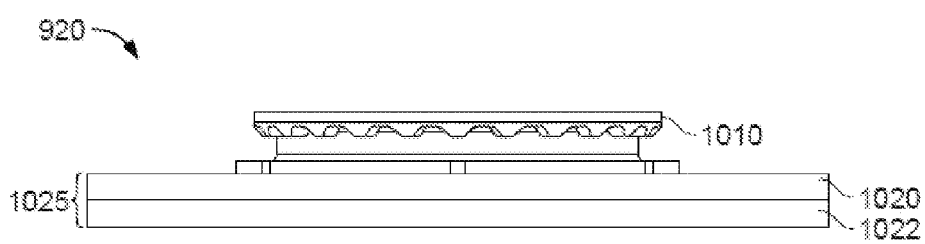
FIG. 34B is a side view of the cuff of FIG. 33.

Referring to FIGS. 34A and 34B, the cuff 920 includes an attachment component such as a ring 1010 that engages the inflow cannula 950 and/or other portions of the pump 912 to secure the cuff 920 and pump 912 together. In the example illustrated, the ring 1010 is formed by a patterned metal component (e.g. titanium) covered with, for example, silicone. The ring 1010 may include, for example, an attachment member (having one or more features of any of the attachment members 26, 126, 326, 626), and a linking member (having one or more features of any of the linking members 24, 124, 324, 624). The cuff 920 is secured to the pump 912 using the techniques described above. For example, the cuff 920 may be coupled to and locked to the pump 912 in the same manner that any of the cuffs 20, 120, 320, 620 are locked and coupled to the pumps 12, 250, 750. A clinician may lock the cuff 920 to the pump 912 using any of the locking mechanisms described above, such as using the clips 200, 700.

The cuff 920 includes two disc-shaped layers 1020, 1022, and together, the layers 1020, 1022 form a sewing ring 1025. To install the cuff 920, a clinician places sutures, staples, or other fasteners through the sewing ring 1025 and the heart 914. In some implementations, only one disc or more than two discs are included in the sewing ring 1025.

The layers 1020, 1022 are formed of, for example, a felt, a mesh, a woven material, or another fabric. The layers 1020, 1022 are formed of polytetrafluoroethylene (PTFE), polyethylene terephthalate (PET) (e.g., Dacron), polyester, or another material. In some implementations, the layers 1020, 1022 are each formed of PTFE felt. In some implementations, the layers 1020, 1022 are each formed of a woven polyester.

The layers 1020, 1022 are joined together by sutures, for example, sutures at the inner diameter and outer diameter of the layers 1020, 1022. In some implementations, the layers 1020, 1022 are additionally or alternatively joined by an adhesive, such as a silicone adhesive, or another fastener.

The layers 1020, 1022 have a stiffness that tends to flatten the myocardium of the heart 914 when the cuff 920 is installed. This flattening reduces the probability of inflow cannula malposition. As an additional advantage, in some implementations, the stiffness of the layers 1020, 1022 (and of the sewing ring 1025 as a whole) makes the cuff 920 easier for the clinician to hold. The relative stiffness of the cuff 920 may aid a clinician in pressing the cuff 920 against the pump 912 when attaching the pump 912 and the cuff 920. For example, the clinician may more easily apply a counterforce against the pump 912 when the inflow cannula 950 is inserted into the cuff 920, permitting the cuff 920 to be more easily seated against the pump 912.

In some implementations, the sewing ring 1025 has a flexural modulus of greater than 50 psi (pound-force per square inch). In some implementations, the flexural modulus of the sewing ring 1025 is at least 60 psi, at least 75 psi, at least 90 psi, at least 100 psi, at least 125 psi, or at least 150 psi. The sewing ring 1025 may have a flexural modulus in one of these ranges along a portion of, a majority of, or substantially all of the sewing ring 1025. In some implementations, the sewing ring 1025 has a flexural modulus in one of the ranges indicated above across the entire diameter of the sewing ring 1025. In some implementations, the flexural modulus of the sewing ring 1025 is, for example, less than 1500 psi, less than 1000 psi, or less than 750 psi. A flexural modulus under one of these ranges can facilitate insertion of a needle through the sewing ring 1025 without requiring an excessive amount of insertion force.

The fabric of the layers 1020, 1022 can provide the rigidity that causes the sewing ring 1025 to have a flexural modulus in these ranges, without any additional component formed of, for example, metal or polymer. Because the sewing ring 1025 is fabric, in some implementations, a clinician is able to insert a needle through any exposed portion the sewing ring 1025 without the needle being impeded by structures of the sewing ring 1025. In some implementations, another component in the sewing ring 1025, such as the insert 1030 described below, can contribute to the rigidity of the sewing ring 1025, so that the sewing ring 1025 as a whole has a flexural modulus in one of the ranges indicated above.

In some implementations, one or more of the layers 1020, 1022 individually has a flexural modulus of greater than 50 psi, for example, a flexural modulus at least 60 psi, at least 75 psi, at least 90 psi, at least 100 psi, at least 125 psi, or at least 150 psi. In addition, the flexural modulus of each of the layers 1020, 1022 can be, for example, less than 1500 psi, less than 1000 psi, or less than 750 psi. In some implementations, the sewing ring 1025 includes only a single layer of fabric or other material that provides a flexural modulus in the ranges indicated above.

Referring to FIG. 33, to install the pump 912, the cuff 920 may be installed at the heart 914. A clinician or a tool holds the cuff 920 by the ring 1010 and/or the sewing ring 1025 as the pump 912 is subsequently positioned relative to the cuff 920. For example, a tool or the clinician's fingers may grasp the cuff 920 by pressing against the outer edges of the sewing ring 1025. The clinician moves the pump 912 toward the cuff 920 in the direction of arrow A. As the pump 912 moves relative to the cuff 920, a coupling mechanism attaches the cuff 920 to the pump 912. For example, features of the ring 1010 engage features of the inflow cannula 950. The cuff 920 may be required to provide a particular amount of counterforce for the pump 912 to become coupled to the cuff 920. The cuff 920, held by the clinician's fingers or a tool, provides counterforce in the direction of arrow B, to permitting the coupling mechanism to engage. The sewing ring 1025 may be sufficiently rigid that, while the cuff 920 is held through inward force from the outer edges of the sewing ring 1025, the sewing ring 1025 does not buckle or deform, and the cuff 920 exerts a sufficient amount of force against the pump 912 that a coupling mechanism the pump 912 and the cuff 920.

Referring again to FIGS. 34A and 34B, in some implementations, the layers 1020, 1022 each have a thickness of between approximately 1.3 mm and 2.3 mm, or approximately 1.8 mm, and may have a maximum water permeability of between approximately 450 ml/cm2/min and 650 ml/cm2/min, or approximately 550 ml/cm$^2$/min. Accordingly the use of two such layers 1020, 1022 together in the sewing ring 1025 provides a higher stiffness than a single layer of lower density, higher porosity PTFE felt, for example, a single layer having a thickness of approximately 2.9 mm and a maximum water permeability of approximately 750 ml/cm$^2$/min. A high-density, low-porosity felt material for the layers 1020, 1022 may be obtained by compressing a lower density felt material, (such as compressing the 2.9 mm thick felt with 750 ml/cm$^2$/min maximum water permeability to approximately half of its initial thickness).

Figure 34C:
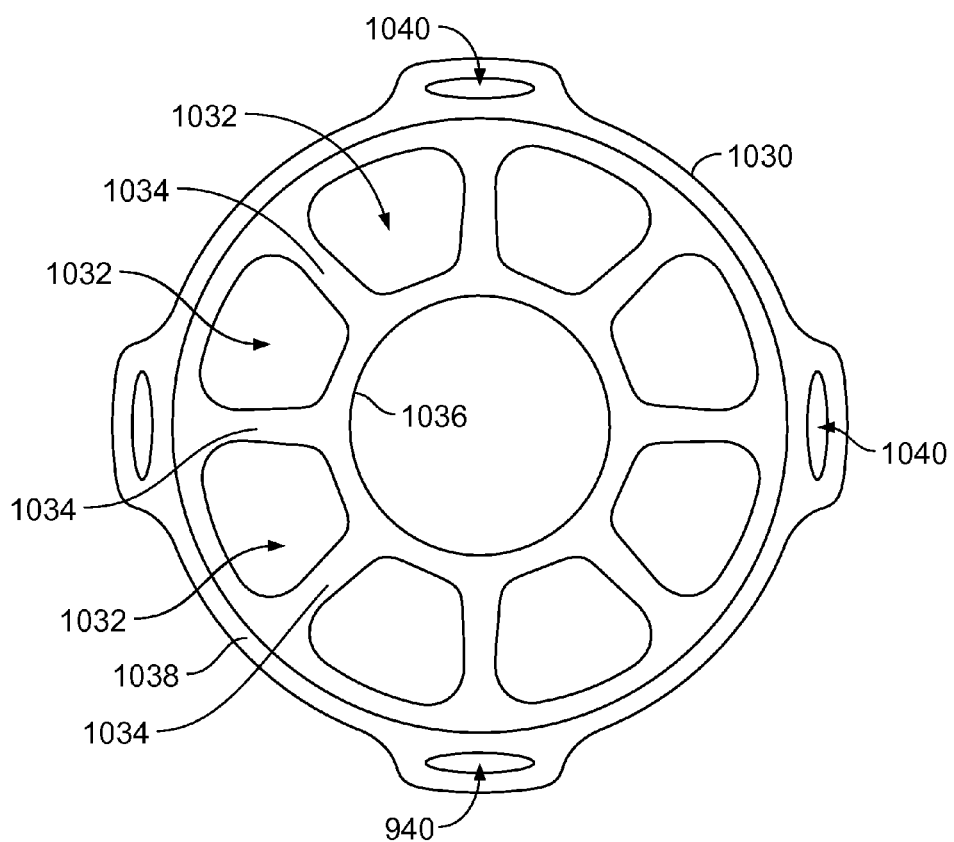
FIG. 34C is a top view of an insert that may be included in the cuff of FIG. 33.
Figure 34D:
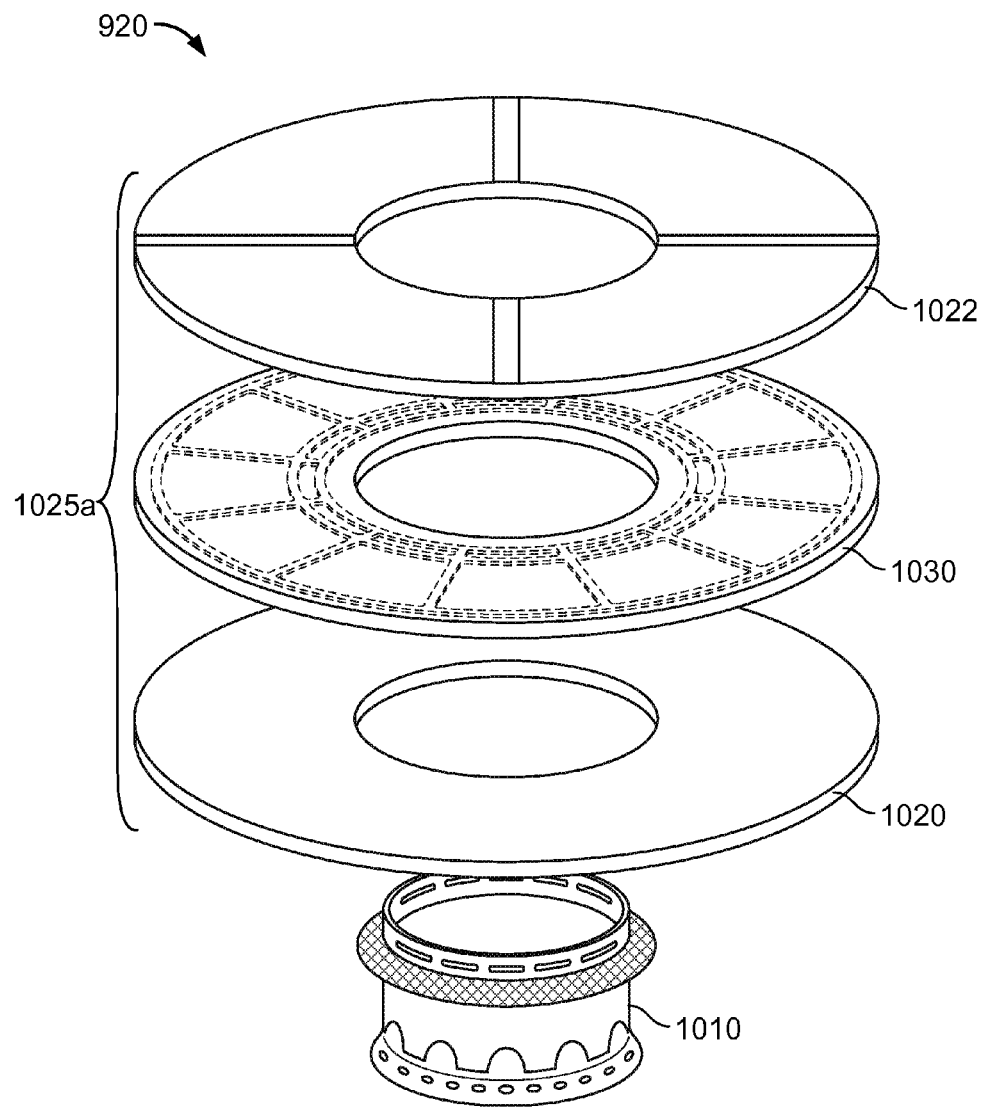
FIG. 34D is an exploded view of the cuff of FIG. 33 including the insert.

Referring to FIGS. 34C and 34D, in some implementations, an insert 1030, such as a lattice or web of a firm or resilient material, is included in the sewing ring 1025, forming a sewing ring 1025*a* (FIG. 34D). The insert 1030 is generally planar. The insert 1030 may be positioned between the layers 1020, 1022, and may be formed of a material stiffer than the material of the layers 1020, 1022. For example, the insert 1030 may be formed of polyether ether ketone (PEEK), titanium, a cobalt chromium alloy, a shape-memory polymer, or another material. The insert 1030 can be molded, machined, printed, stamped, formed of wire, laser cut from a metal sheet, or formed in another manner. In some implementations, the insert is formed of a super-elastic material such as titanium alloy (e.g. nickel-titanium alloy).

In some implementations, the insert 1030 retains its shape when bent, permitting a clinician to manually shape the sewing ring 1025*a* as desired for a particular implantation (e.g., shaping the sewing ring 1025*a* with one bent edge, in a conical shape, etc.). After implantation, the sewing ring 1025*a* shapes the myocardium to substantially conform to the shape of the sewing ring 1025*a*.

The insert 1030 defines windows or openings 1032 through the insert 1030. The openings 1032 define areas where sutures may be placed through the insert 1030 to achieve hemostasis.

The insert 1030 may be formed as, for example, a web, lattice, or mesh that defines the openings 1032, thereby providing regions where needles can pass through unimpeded while providing strength and stiffness across substantially the entire sewing ring 1025. At the openings 1032, sutures can be inserted without interference from, for example, extensions or supports 1034 that extend radially, connecting an inner ring 1036 and an outer ring 1038 of the insert 1030. The insert 1030 may be covered in silicone or another material. For example, the insert 1030 may be embedded within in a sheet of silicone, with the silicone covering the openings 1032. An opening in the center of the insert 1030 is not covered with silicone, allowing the inflow cannula 950 to pass through the center of the insert 1030. In some implementations, the insert 1030 includes one or more anchors 1040 located at the outer edge of the insert 1030. The anchors 1040 are openings defined in the insert 1030 through which sutures may be placed to secure the cuff 920 to the myocardium.

In some implementations, the insert 1030 has a flexural modulus of greater than 50 psi, for example, a flexural modulus at least 60 psi, at least 75 psi, at least 90 psi, at least 100 psi, at least 125 psi, or at least 150 psi. In some implementations, the sewing ring 1025a as a whole has a flexural modulus in one of these ranges.

Figure 35:
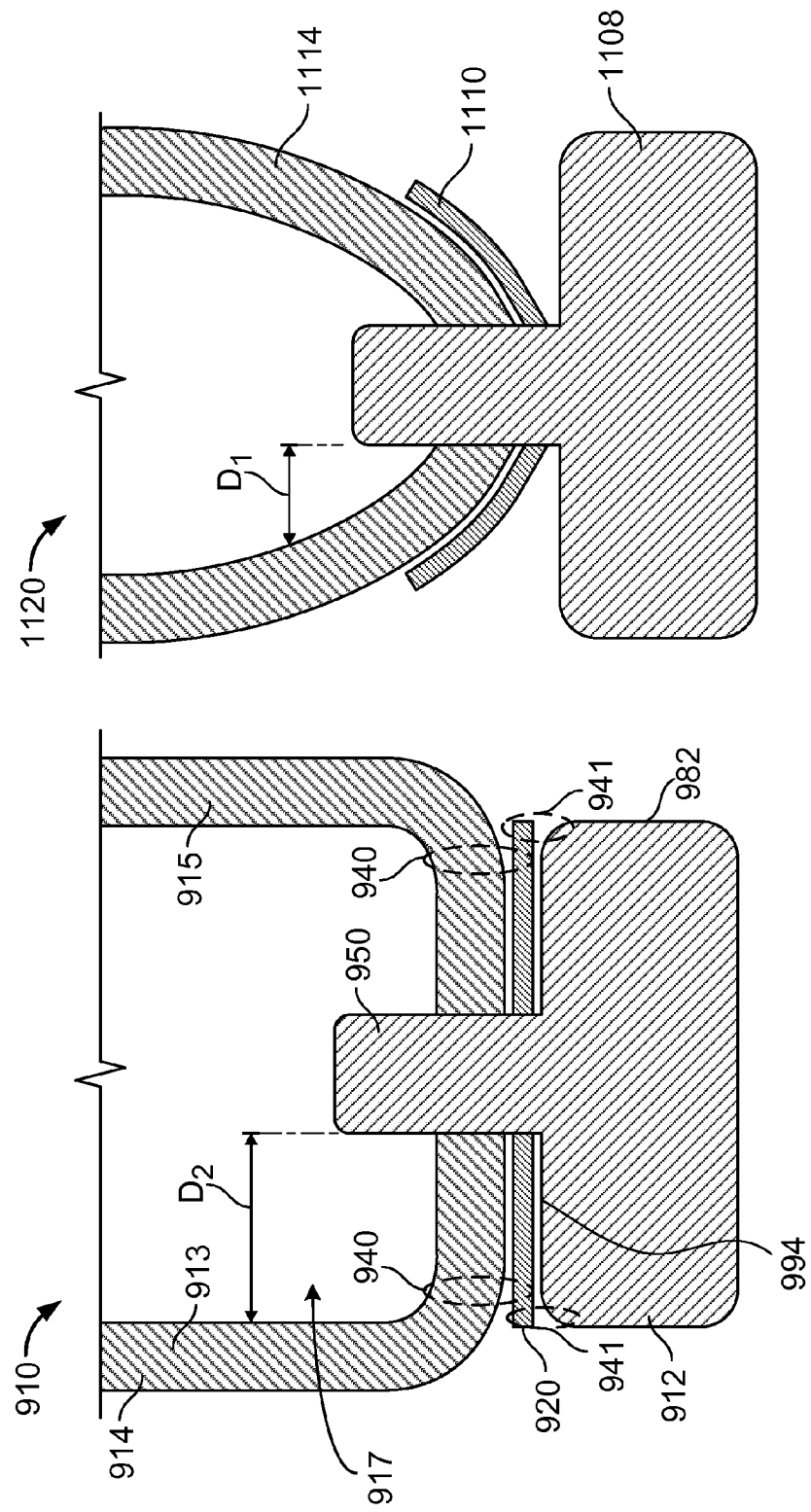
FIG. 35 is a side cutaway view of two different cuffs and associated pumps.

Referring to FIG. 35, some ventricular cuffs provide a flexible interface that allows myocardial tissue to be free from restriction after implantation. As an example, a pump 1108 is attached to a heart 1114 using a cuff 1110. The cuff 1110 is compliant and conforms to the shape of a heart 1114 to which the cuff 1110 is attached. The pump 1108 includes an inflow cannula 1130 that extends into a space 1120 within the heart 1114. The space 1120 in which the inflow cannula 1130 resides is primarily defined by the natural geometry of the heart 1114. In addition, a distance, $D_1$, between the inflow cannula 1130 may change as the patient moves (e.g., as the pump 1108 tilts, twists, or otherwise moves relative to the heart 1114.

By contrast with the cuff 1110, the stiffness of the cuff 920 substantially flattens the myocardium, which expands a space 917 around the inflow cannula 950 and helps maintain an appropriate distance, $D_2$, between the inflow cannula 950 and inner walls 913 of the ventricle. This, in turn, reduces the potential for inflow cannula malposition because of the expanded space 1000 within the ventricle created near the inflow cannula 950. Malpositioning is associated with several risks including decreased pump poor performance and adverse clinical events. If the cannula inflow gets close to or contacts internal structures (e.g. the septum or ventricular walls), the inflow may become partially or completely occluded. Moreover, malpositioning of the inflow near internal structures can alter flow patterns and even form regions of stasis. Accordingly, malpositioning may increase the risk of hemolysis and thrombosis. By making interface of the cuff 920 and pump 912 with the heart 914 (e.g., myocardium) stiffer, the myocardium can be flattened and clinical outcomes can be improved. In some implementations, a clinician attaches the cuff 920 to the heart 914 using sutures 940 placed at or near the outer edge of the sewing ring 1025, permitting the cuff 920 to substantially flatten the myocardium across substantially the entire region of the myocardium that engages the cuff 920. As noted above, flattening the myocardium may limit inflow cannula malposition or reduce the risk of occlusion of the inlet tip of the inflow cannula 950 in the event of malposition. The stiffness of the cuff 920, for example, the stiffness of the sewing ring 1025, may cause the flattening of the myocardium.

Sutures anchored to the pump 912 can also promote flattening of the myocardium. In some implementations, as discussed further below, sutures 941 may be placed through the sewing ring 1025 and a portion of the pump 912, such as the anchors 960. These sutures 941 can hold the sewing ring 1025 near or against the pump 912, further flattening the myocardium or maintaining the shape defined by the cuff 920. In some implementations, one or more sutures may be placed through an anchor 960 and the myocardium, as shown in FIG. 32, in addition to or instead of through the sewing ring 1025.

As shown in FIG. 35, the sewing ring 1025, when generally perpendicular to the inflow cannula 950, can extend along a majority of the diameter of the pump 912. For example, the sewing ring 1025 can have an outer diameter that is at least 50%, at least 75%, or at least 90% of the outer diameter of the pump 912. In some implementations, as shown in FIG. 35A, the sewing ring 1025 extends along substantially all of a proximal side of the pump 912, extending to an outer peripheral wall 982 of the pump 912.

Figure 36A:
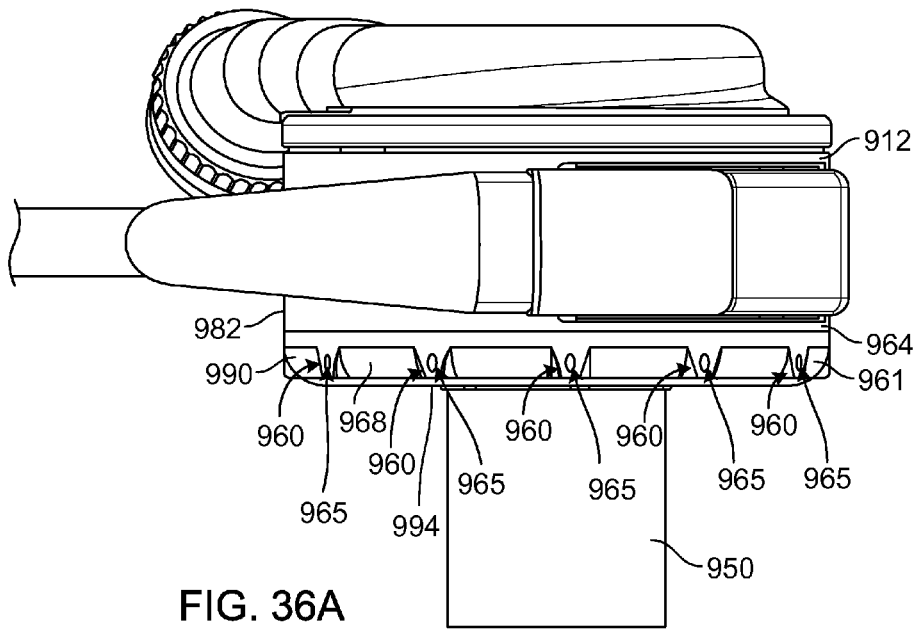
FIG. 36A is a side view of the pump of FIG. 32.
Figure 36B:
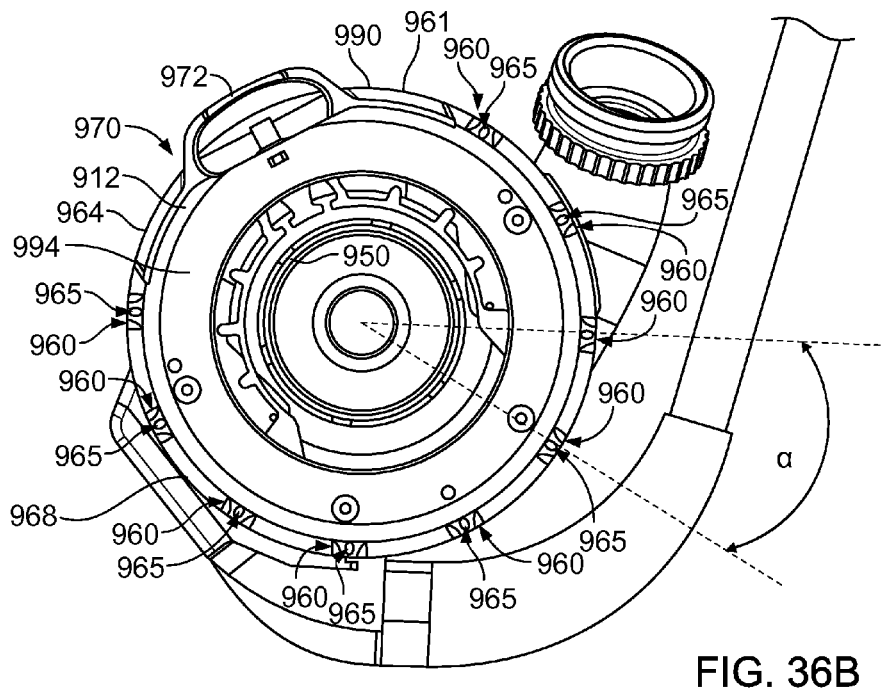
FIG. 36B is a top view of the pump of FIG. 32.

Referring to FIGS. 36A and 36B, the pump 912 can be secured relative to the heart 914 using one or more of the anchors 960. The pump 912 includes the anchors 960 at locations on the exterior of the pump 912, for example, spaced apart around an outer perimeter 961 of a housing 964 of the pump 912. The outer perimeter 961 is generally circular and represents the circumference of the housing 964. The anchors 960 are spaced apart along at least a portion of the circumference. The anchors 960 may be disposed around more than half of the circumference of the housing 964. In the example shown, the anchors 960 are located around the entire circumference of the pump 912 except in a region 970 where a cuff lock 972 is located. The anchors 960 are spaced apart around the pump 912 at an angle α, which may be, for example, between 10 degrees and 50 degrees, or approximately 30 degrees. The pump 912 includes eight anchors 960, but more or fewer anchors 960 may be included. In some implementations, at least three anchors 960 are included.

In some implementations, the anchors 960 include suture eyelets 965 located at an edge of the housing 964. The eyelets 965 are defined to be adjacent to the sewing ring 1025 of the cuff 920 when the pump 912 is implanted. For example, each eyelet 965 has an exit opening adjacent the cuff 920 when the cuff 920 is engaged to the proximal side 994 of the housing 964. During implantation, a clinician may pass sutures or other fasteners through the eyelets 965. At the site of each eyelet 965, the clinician may also pass the sutures through the cuff 920 and/or the myocardium. Passing the sutures through the cuff 920 and/or myocardium at locations adjacent the anchors 960 may help maintain the cuff 920 in a substantially flat against a proximal side 994 of the pump 912, thus flattening the cuff 920 and myocardium. For example, sutures may extend through sewing ring 1025 at or near the outer edge of the sewing ring 1025, pulling the outer edge of the sewing ring 1025 toward (e.g., close to or against) the pump 912.

The sutures may connect the anchors 960 to any of various structures located within the thoracic cavity, such as the patient's ribs, a portion of the myocardium (e.g., a portion spaced apart from the cuff), synthetic material such as Gore-Tex, or other structures. The clinician may secure the other end of each suture at a distance from the anchors 960 (e.g., approximately 0.5 cm, 1 cm, 3 cm, 5 cm, etc.), as selected by the clinician.

In some implementations, the anchors 960 do not increase the outer diameter of the pump 912. The features in which the eyelets 965 are defined occupy space in the region where the edge 968 of the pump housing 964 has been cut, e.g., with a radius. The housing 964 has a rounded, chamfered, or beveled edge where no anchors 960 are placed.

Figure 37A:
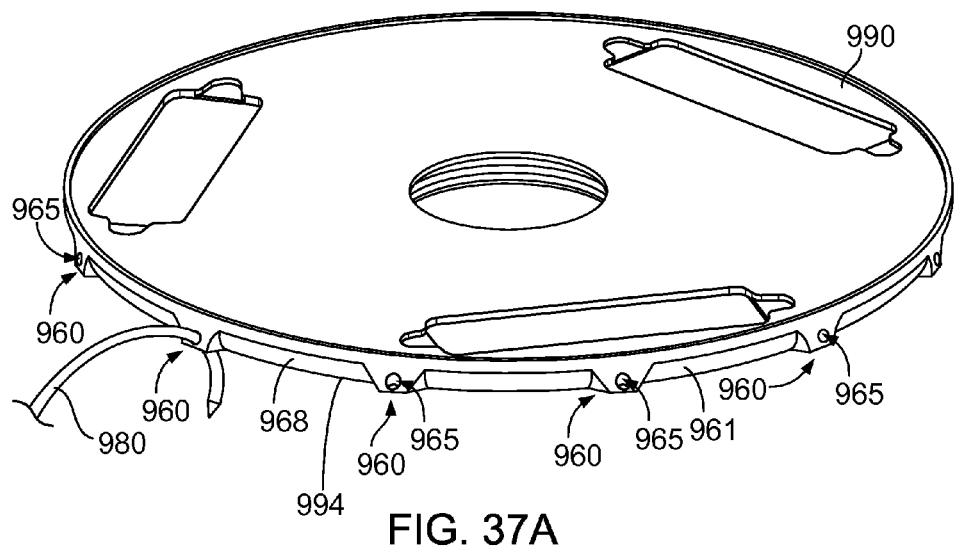
FIGS. 37A and 37B are perspective views of a portion of the pump of FIG. 32.
Figure 37B:
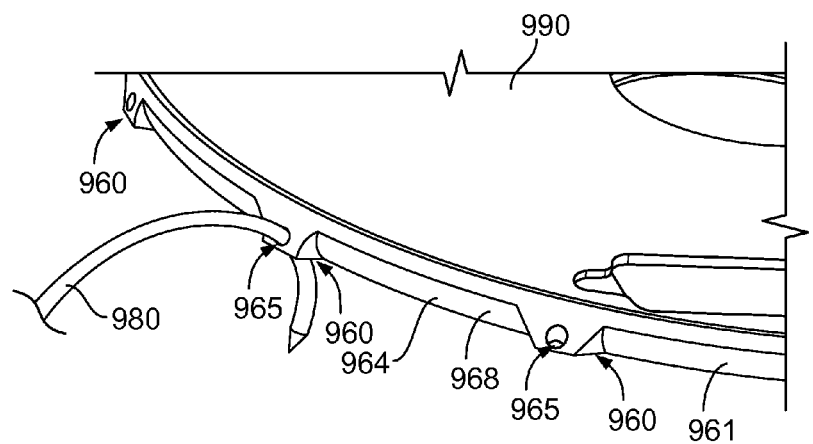
Figure 37C:
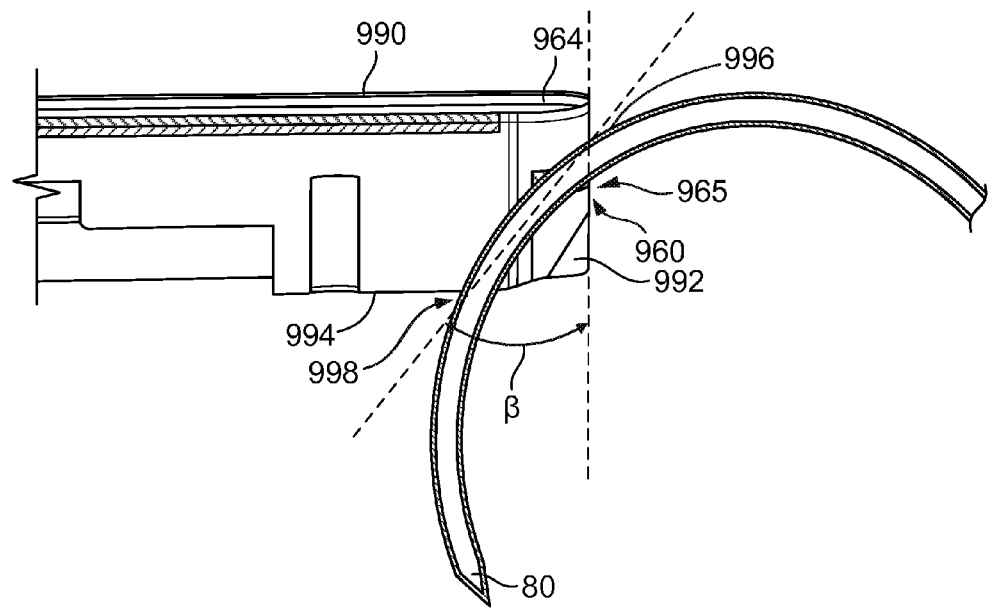
FIG. 37C is a side cutaway view of a portion of the pump of FIG. 32 and a needle.

Referring to FIGS. 37A to 37C, the eyelets 965 are defined in a motor cap 990, which is part of the housing 964 of the pump 912. The motor cap 990 has a side surface 992 and also has a proximal side 994 oriented perpendicular to the side surface 992. The inflow cannula 950 of the pump 912 extends from the proximal side 994, in a direction generally perpendicular to the proximal side 994 (See FIG. 36A). The proximal side 994 faces the cuff 920 when the pump 912 is implanted.

Each eyelet 965 defines a passage that angles inward from an outer wall of the pump 912. In some implementations, each eyelet 965 extends toward the inflow cannula 950 in the center of the proximal side 994. The passage extends between an entry opening 996 defined in the side surface 992 and an exit opening 998 defined in the proximal side 994. The passage defined by each eyelet 965 is oriented at an angle β (FIG. 37C) from the substantially cylindrical peripheral wall 982 (FIG. 36A) of the pump housing 964. In some implementations, the angle β is between approximately 20 degrees and 50 degrees, or is approximately 35 degrees. The angled trajectory of the eyelet 965 allows the clinician to place a suture through the eyelet 965 and capture the PTFE felt or other material of the sewing ring 1025 of the cuff 920 as well as the myocardium if desired. When the cuff 920 is positioned about the inflow cannula 950 and the sewing ring 1025 is positioned adjacent the proximal side 994 of the housing 964, each eyelet 965 is oriented to direct a needle travelling through the eyelet 965 into the sewing ring 1025.

The eyelets 965 may accommodate a curved needle 980 and may define a curved or linear path through the pump housing 964. The eyelets are designed to accommodate a #1-0 suture and needle. To accommodate the diameter and typical radius of curvature for these needles, the diameter of the eyelet 965 may be approximately 0.034 inches.

A clinician may selectively fasten the anchors 960 to portions of a patient's anatomy to limit potential for subsequent malposition of the inflow cannula 950. For example, the clinician may select the particular anchors 960 at which to attach sutures according to the needs of the patient. The clinician may attach sutures or other fasteners at fewer than all of the anchors 960, may attach secure different anchors 960 to different tissues or different regions of tissue, and may connect the anchors 960 to locations at different distances from the pump 912 and cuff 920. For example, while the pump 912 includes eight anchors 960, a clinician may select to secure the pump 912 using only three anchors 960 that are evenly spaced apart around the pump 912, or may select to secure the pump 912 using five of the anchors 960 that are adjacent to each other, or may use another set of the anchors 960.

In some implementations, anchors 960 are disposed at portions of the pump housing 964 other than the outer edge of the motor cap 990. For example, anchors 960 may additionally or alternatively be placed on the peripheral wall 982 or other surfaces of the housing 964.

Figure 38:
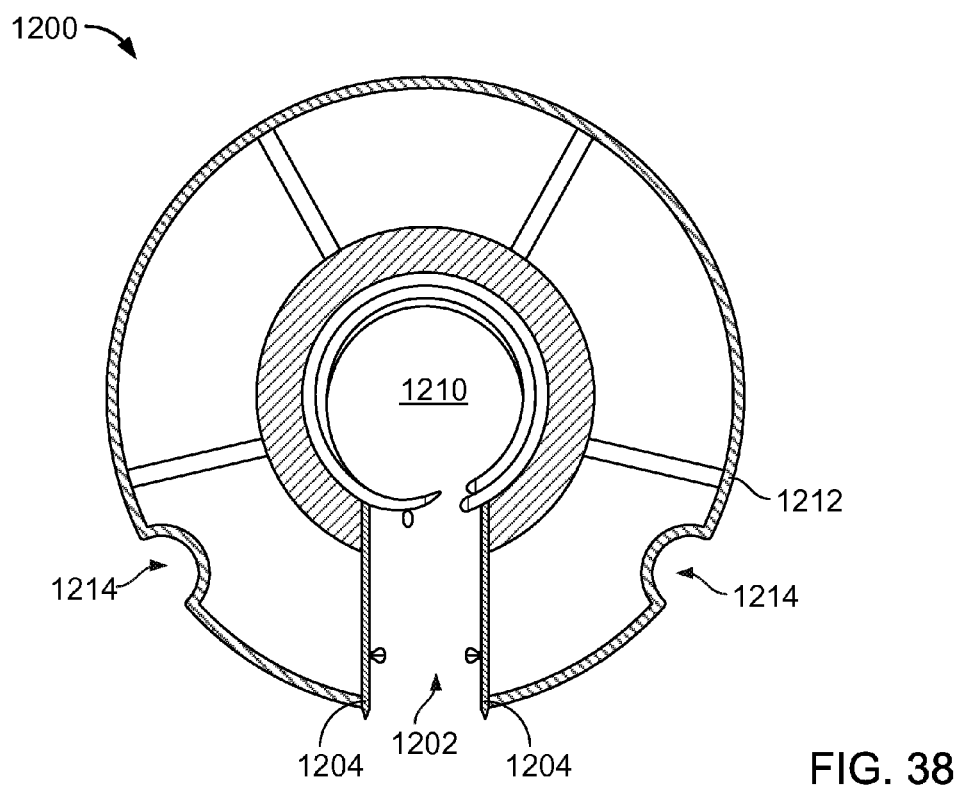
FIG. 38 is a top view of an alternative cuff.

Referring to FIG. 38, an alternative cuff 1200 defines a radial opening 1202. The cuff 1200 includes fasteners 1204 that permit a clinician to close the opening 1202 after the cuff 1200 is placed about the inflow cannula 950 of the pump 912. The fasteners 1204 snap together to capture the inflow cannula 950 in a central opening 1210 defined in the cuff 1200. The cuff 1200 defines, in an outer edge 1212, indentations or recesses 1214 that a tool or clinician's finger may engage to force the fasteners 1204 against each other.

During implantation of the pump 912, a clinician may attach a portion of the cuff 1200 to the heart 914 (e.g., attach the cuff 1200 partially around the circumference of the cuff 1200). The clinician may then mate the pump 912 to the cuff 1200, close the cuff 1200 with the fasteners 1204, and attach the rest of the cuff 1200 to the heart to form a hemostatic seal.

Figure 39:
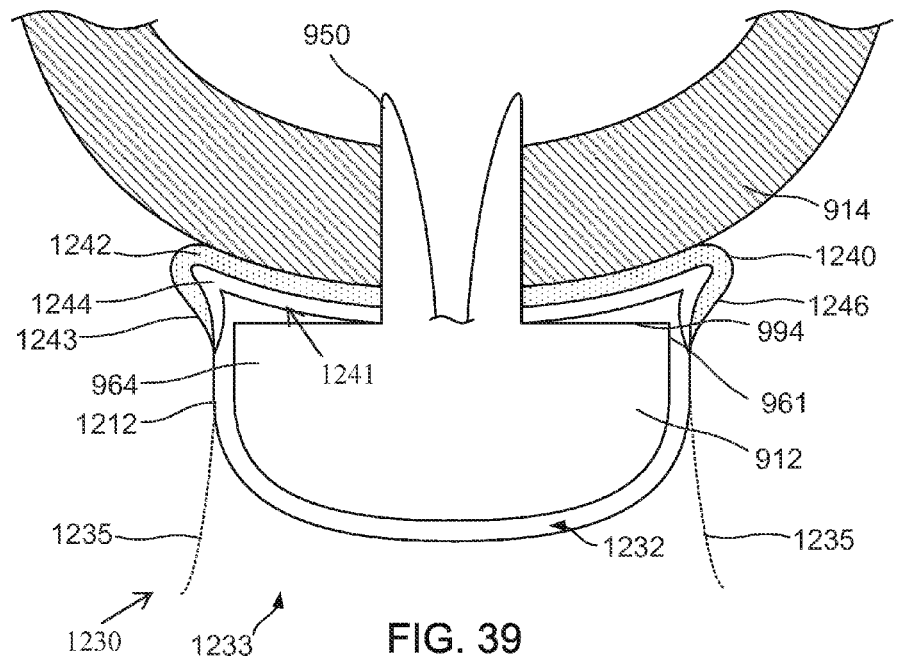
FIG. 39 is a cross-sectional view of the pump of FIG. 32 with a flexible cover.

Referring to FIG. 39, a cover 1230 may be placed around the pump 912 during implantation to facilitate later removal of the pump 912. After the pump 912 is implanted, various tissues may adhere to the pump 912 over time. Adhered tissues may make removal of the pump 912 from the patient's body difficult, since the clinician may need to scrape off or cut off tissues adhered to various surfaces of the pump 912. To limit tissue adhesion and tissue growth on the pump 912, a clinician may surround a portion of or all of the housing 964 of the pump 912 with the cover 1230. As a result, the cover 1230 forms a pouch or pocket around the pump 912 and acts as a barrier to block tissue adhesion to the pump 912. The cover 1230 remains implanted with the pump 912. Tissues may adhere to the exterior of the cover 1230, but do not contact the surface of the pump 912. The cover 1230, unlike the pump 912, may be easily dissected at the time the pump 912 is removed.

If removal of the pump 912 is later desired, the cover 1230 is opened and the pump 912 removed from the patient's body. In some implementations, a clinician cuts apart the cover 1230 to access the pump 912. The surgeon may then remove the pump 912, and may also remove the cover 1230.

The cover 1230 is formed of a flexible material, for example, one or more layers of a fabric. The cover 1230 may be formed of polyester, PET, PTFE, or another biocompatible material. In some implementations, the cover 1230 is part of a cuff 1240 that attaches to the heart 914. The cuff 1240 includes a sewing ring 1241 comprising a fabric layer 1242 formed of, for example, PTFE felt, and a silicone layer 1244. The cover 1230 is attached to the outer edge 1246 of the cuff 1240, for example, along some of or all of the outer circumference of the sewing ring 1241. The cover 1230 may be attached to the sewing ring 1241 with, for example, sutures, staples, adhesives or other means. For example, a portion of the cover 1230 may be disposed between the fabric layer 1242 and the silicone layer 1244, or between other layers of the sewing ring 1241.

In FIG. 39, the cover 1230 is shown closed around the pump 912. Before closing the cover 1230, the cover 1230 has an opening 1233 that admits the pump 912 into an interior space 1232 within the cover 1230 during implantation. Side walls 1235 of the cover 1230, representing the cover 1230 before being closed, are illustrated in dashed lines. The opening 1233 is located between the side walls 1235. After the pump 912 is positioned within the cover 1230 and is attached to the cuff 1240, the clinician closes the opening in the cover 1230 to enclose the pump 912. The cover 1230 may be closed using, for example, sutures, staples, adhesives, or other fasteners. Even when the cover 1230 is closed, the cover 1230 defines an opening to allow an outflow conduit and a driveline cable to exit the cover 1230.

In some implementations, a cover is separate from the cuff 1240. For example, after the pump 912 has been attached at the heart 914, a cover may be placed around the pump 912 and then be sutured to the sewing ring 1241 or otherwise secured around the pump 912.

In some implementations, the sewing ring 1241 extends radially outward from the inflow cannula 950 to or beyond the outer perimeter 961 of the pump 912. That is, the outer diameter of the sewing ring 1241 can be as large as or larger than the outer diameter of the pump 912 at the proximal side 994. As a result, after the pump 912 is seated against the cuff 1240, the outer edge of the sewing ring 1241 remains exposed and accessible to the clinician. The clinician may then place a cover over the pump 912, and may attach the edge of the cover to the fabric at the exposed regions of the sewing ring 1241 with sutures or another fastener.

In some implementations, a portion 1243 of the sewing ring 1241 extends distally, for example, past the proximal side 994 of the pump 912 when the cuff 1240 is seated against the pump 912. In some implementations, the portion 1243 extends around a majority of, or substantially all of, the circumference of the pump 912. The clinician may attach a cover around the pump 1242 by attaching a fabric or other material to the portion 1243.

Figure 40:
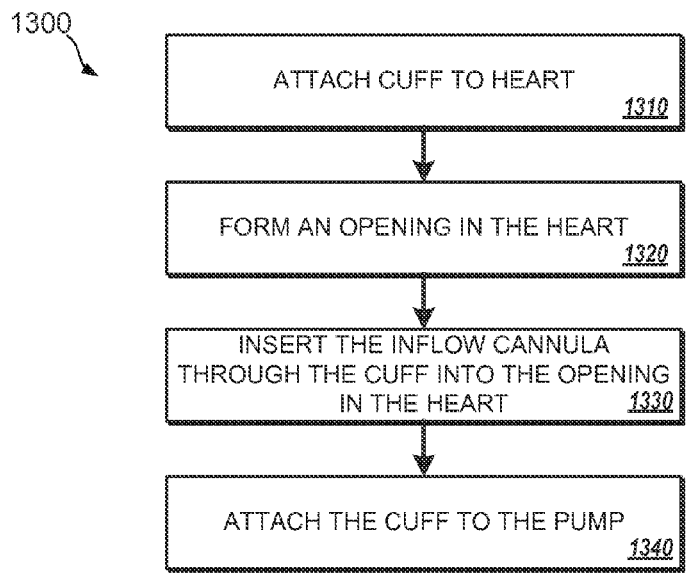
FIG. 40 is a flow chart illustrating a process for implanting a pump.

Referring to FIG. 40, an example of a process 1300 for implanting the pump 912 is illustrated. The process 1300 describes implantation with an apical approach, but other implantation locations and techniques may be used.

A clinician attaches the cuff 920 to a heart (1310). For example, for implantation in an LVAD configuration, the clinician locates the apex of the left ventricle, and sutures the sewing ring 1025 of the cuff 920 to the myocardium. As discussed above, the cuff 920 can be sufficiently rigid to flatten at least a portion of a myocardium of the heart (e.g., a portion adjacent the cuff) when the cuff 920 is attached to the heart 914. For example, the cuff 920 may include two or more layers of fabric, and may include a generally planar insert 1030 that is more rigid than the layers of fabric.

The clinician forms an opening in the myocardium (1320). For example, the clinician may use a coring tool to excise a cylindrical segment of the myocardium. In some implementations, when the cuff 920 is attached to the heart before cutting the opening in the myocardium, the clinician cuts the opening through a central opening in the cuff 920. In other implementations, the clinician cuts the opening in the myocardium and afterward attaches the cuff 920 to the heart 914, with the central opening of the cuff 920 located over the opening of the myocardium.

The clinician inserts the inflow cannula 950 of the pump 912 through the central opening in the cuff 920 and into the opening in the myocardium (1330).

The clinician then attaches the pump 912 to the cuff 920 (1340). For example, the clinician may engage a coupling mechanism that is configured to limit translation of the inflow cannula through the central opening of the cuff 920. To engage the coupling mechanism, the clinician holds the cuff 920 by pressing inward on the outer edge of the cuff 920. The clinician applies a counterforce against the inflow cannula 950 or the pump 912, in a direction along the central axis of the inflow cannula 950, to seat the cuff 920 on the inflow cannula 950 or another portion of the pump 912. In some implementations, the clinician engages a locking mechanism after engaging the coupling mechanism. For example, the clinician may slide a clip into position, by moving the clip in a plane generally perpendicular to the inflow cannula 950.

To attach the pump 912 to the cuff 920, the clinician optionally attaches one or more sutures to one or more suture anchors disposed on an exterior of the pump 912. For example, the clinician passes sutures through eyelets disposed along an outer perimeter of the pump 912 and through the sewing ring 1025 of the cuff 920. The clinician additionally or alternatively may pass the sutures through a portion of the myocardium. Sutures attached at various suture anchors around the pump maintain the position of the sewing ring 1025 extending generally along a plane perpendicular to the inflow cannula 950.

In some implementations, the process 1300 includes covering the pump 912 with the cover 1230. For example, the clinician wraps a fabric around the housing 964 of the pump 912, and closes the fabric to encase the pump 912, shielding the exterior of the pump 912 from tissue adhesion.

Referring to FIG. 41, an assembly 1400 includes a cuff 1410 and an inflow cannula 1430 that are connected together prior to implantation, and then implanted as a single unit. Pre-attaching the cuff 1410 and inflow cannula 1430 may reduce the number of components the clinician must install during implantation. In addition, using the assembly 1400 may reduce the complexity of the implantation procedure and may reduce the risk of bleeding after implantation.

The cuff 1410 includes a fabric ring 1412, for example, a ring of polyester velour or PTFE felt, that a clinician may suture to the heart 914. The fabric ring 1412 is attached to a body 1414 that extends around the inflow cannula 1430. A clamp or clip 1416 extends around the body 1414 and the inflow cannula 1430 to secure the cuff 1410 to the inflow cannula 1430. In some implementations, an adhesive or other fastener secures the cuff 1410 and inflow cannula 1430.

The inflow cannula 1430 has a distal end 1438 that includes one or more attachment features, such as screw threads or clips, to attach to the pump 912. The inflow cannula 1430 defines a central axis 1432 and defines an inlet 1434 at a proximal end 1436. The inflow cannula 1430 flares outward from the central axis 1432 at the proximal end 1436. When implanted, the flared proximal end 1436 contacts the endocardium, e.g., the inner surface of the heart 914. The flared proximal end 1436 separates the endocardium 915 from the inlet 1434, limiting the potential for occlusion of the inlet 1434 by the endocardium 915. As a result, the region of the heart 914 adjacent the inflow cannula 1430 is secured between the fabric ring 1412 on the exterior of the heart 914 and the flared proximal end 1436 on the interior of the heart 914.

To implant the assembly 1400, the clinician first cuts an opening in the myocardium. The clinician then inserts the proximal end 1436 into the opening, and sutures the fabric ring 1412 to the myocardium. With the assembly 1400 attached to the heart, the clinician attaches the distal end 1438 of the inflow cannula 1430 to the pump. For example, the distal end 1438 may be received into the housing of the pump, and may be secured by threads, a clip, or another fastening mechanism.

Referring to FIGS. 42A and 42B, a cuff and cannula assembly 1450 includes an inflow cannula 1460 having a fabric 1470 attached directly to the exterior of the inflow cannula 1460. The inflow cannula 1460 has a circumferential ridge 1462 that extends around the exterior of the inflow cannula 1460. The fabric 1470, for example, a ring of a polyester velour or PTFE felt, is positioned on the ridge 1462 and extends around the inflow cannula 1460.

As shown in FIG. 42B, holes 1464 are defined through the ridge 1462. Sutures 1472 extend through the holes 1464 and the fabric 1470 to secure the fabric 1470 to the inflow cannula 1460. The assembly 1450 may be provided to a clinician with the fabric 1470 already secured to the inflow cannula 1460. During implantation, after the clinician positions the assembly 1450 relative to the heart 914, for example, with the inflow conduit 1460 extending into the left ventricle, a clinician places sutures 1480 to secure the fabric 1470 to the myocardium.

Figure 43:
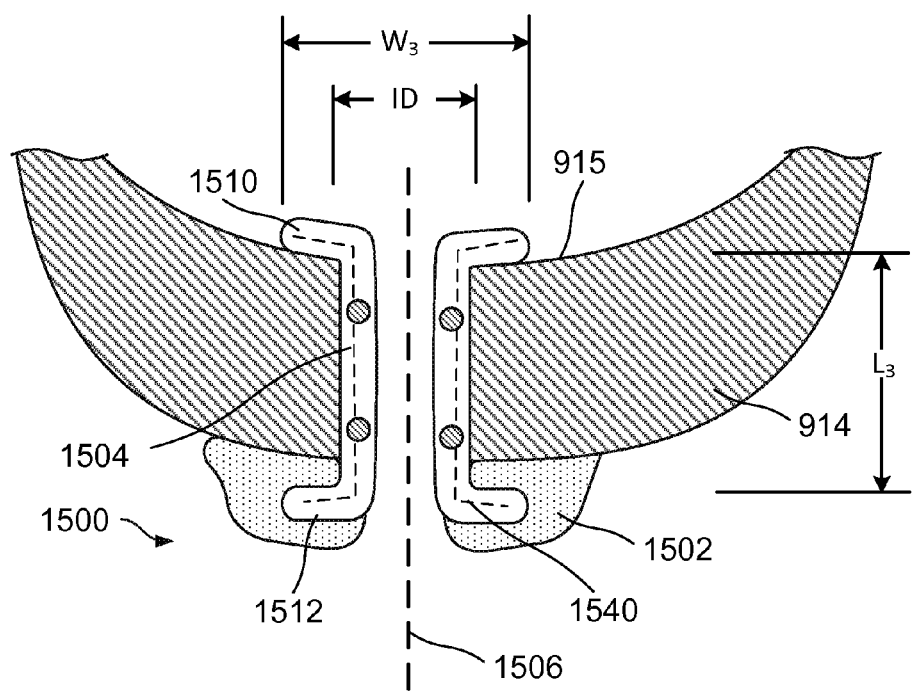
FIGS. 43 and 44 are cross-sectional views of alternative cuffs.

Referring to FIG. 43, a cuff 1500 includes a proximal portion 1510 that extends into the heart 914 and contacts the endocardium 915. In general, positioning a portion of an inflow cannula, cuff, or other component against the endocardium 915 can separate the endocardium 915 from the inlet of an inflow cannula, reducing the risk of occlusion of the inflow cannula.

As shown in FIG. 43, the cuff 1500, which is separate from the inflow cannula 950 of the pump 912, engages the interior of the heart 914 and the exterior of the heart 914. After a hole is cored in the heart 914, the cuff 1500 is deployed to capture a portion of the myocardium between the proximal portion 1510 and a distal portion 1512, which results in flattening of the myocardium. After the cuff 1500 is placed on the heart 914, the clinician may insert the inflow cannula 950 of the pump 912 through the center of the cuff 1500 and attach the cuff 1500 to the pump 912. The cuff 1500 remains in place on the heart 914, with the inflow cannula 950 extending through the cuff 1500, to limit the risk of pump malposition and occlusion of the inflow cannula 950.

To promote flattening of the myocardium, the proximal portion 1510 and/or the distal portion 1512 can have a flexural modulus of greater than 50 psi, for example, a flexural modulus at least 60 psi, at least 75 psi, at least 90 psi, at least 100 psi, at least 125 psi, or at least 150 psi.

In the example of FIG. 43, the cuff 1500 includes a fabric 1502, such as a ring of a polyester velour or PTFE felt, and a member 1504 formed of, for example, a flexible material such as silicone. The fabric 1502 may be attached to the distal portion 1512 of the member 1504. For example, the fabric 1502 may be captured in silicone of the member 1504. The clinician may attach the fabric 1502 to the heart 914, for example, with sutures. As discussed further below, some implementations of the cuff 1500 may be attached to the heart 914 without the fabric 1502 and without sutures or other fasteners.

The member 1504 defines a central axis 1506. The member 1504 includes the proximal portion 1510, which is formed as one or more extensions or tabs that extend outward from the central axis 1506. In some implementations, the proximal portion 1510 is a circumferential ring that extends radially outward from the central axis 1506 in a plane generally perpendicular to the central axis 1506. The proximal portion 1510 has a width, $W_3$, larger than the inner diameter, ID, of the opening in the heart 914. As a result, to pass through the opening, the proximal portion 1510 deflects inward toward the central axis 1506. Once the proximal portion 1510 has passed through the myocardium into, for example, a ventricle of the heart 914, the proximal portion 1510 expands outward, limiting the cuff 1500 from separating from the heart 914. The proximal portion 1510 rests on the endocardium 915, along the inner surface of the heart 914.

After the cuff 1500 is coupled to the heart 914, an inflow cannula may be placed through the member 1504 and secured within the member 1504. The presence of the proximal portion 1510 against the endocardium 915 can reduce the risk that heart tissue encroaches on the internal lumen of the inflow cannula. In the implanted configuration, the cuff 1500 remains around the inflow cannula 950 of the pump 912, securing the pump 912 to the heart 914.

In some implementations, the distal portion 1512 of the member 1504 extends generally radially outward from the central axis 1506, for example, as a circumferential flange. The proximal portion 1510 also extends generally radially outward from the central axis 1506, for example, as a circumferential flange. The length, $L_3$, of the member 1504 between the proximal portion 1510 and the distal portion 1512 can be configured to exert pressure on the portions of the myocardium captured between the proximal portion 1510 and the distal portion 1512.

In some implementations, the member 1504 is elastic, expandable, or otherwise adjustable to change the length, $L_3$. The length, $L_3$, may be adjusted to exert a desired amount of force on the myocardium to flatten the myocardium and secure the position of the cuff 1500 relative to the heart 914. The length, L, may also be adjusted to accommodate varying thicknesses of heart walls. For example, the member 1504 may have corrugated walls that may expand or compress to adjust the length, $L_3$. As another example, the member 1504 may include a resilient member, such as a spring, located between the proximal portion 1510 and the distal portion 1512 to exert a compressive force against tissue located between the proximal portion 1510 and the distal portion 1512. As another example, the member 1504 may include a frame 1540 (shown in dashed lines) or other component with a shape memory, for example, an internal frame formed of nickel-titanium alloy, a polymer, or other material. After placement of the cuff 1500 into the opening in the heart 914, the frame 1540 may contract to decrease the length, $L_3$, and compress the myocardium between the proximal portion 1510 and the distal portion 1512. For example, heat may activate the shape memory of the frame 1540 and cause the cuff member 1504 to contract.

In some implementations, the cuff 1500 is configured to maintain its position on the heart 914 without being sutured to the heart. The cuff 1500 may be secured to the heart 914 by the capture of the myocardium between the proximal portion 1510 and the distal portion 1512. Accordingly, the fabric 1502 or other material may be omitted. Engagement with the heart 914 can also flatten the myocardium as discussed above.

A cuff 1500 that can be secured to the heart without sutures includes the frame 1540, which may be formed of, for example, a super-elastic or shape memory material, such as nickel-titanium alloy or a polymer. The frame 1540 may be covered in, for example, fabric, PTFE felt, polyester, silicone, or another biocompatible material. In some implementations of the cuff 1500, the frame 1540 is exposed and does not have a covering. In preparation for placement on the heart 914, the proximal portion 1510 is deflected inward toward the axis 1506, which permits the proximal portion 1510 to enter a hole in the heart 914 having an inner diameter, ID, less than the width, $W_3$, or outer diameter of the proximal portion 1510. The clinician may use a tool to hold the proximal portion 1510 in the deflected position while inserting the proximal portion 1510 through the hole in the heart 914.

Once within the heart 914, the proximal portion 1510 expands outward, for example, due to the resiliency or shape memory of the frame 1540. For example, the frame 1540 may be configured to respond to body heat or other conditions to regain its natural form, in which the proximal portion 1510 extends radially outward. The shape memory or resiliency of the frame 1540 also causes the cuff 1500 to contract, exerting a force on the myocardium between the proximal portion 1510 and the distal portion 1512. In some implementations, a tool may be used to expand the proximal portion 1510 within the heart 914 and/or to adjust the length, $L_3$, in addition to or instead of the resiliency or shape memory of the frame 1540. With the cuff 1500 deployed in this manner, pressure on the region of the myocardium surrounding the hole in the heart 914 secures the cuff 1500 in position with respect to the heart 914, without the need for sutures or other fasteners. The pressure exerted by the cuff 1500 on the heart 914 maintains the position of the pump 914 and its inflow cannula 950 relative to the heart 914 after the pump 914 is secured to the cuff 1500.

Other techniques may also be used to capture portions of the myocardium. For example, the member 1504 may be divided into a proximal component that includes the proximal portion 1510 and a distal component that includes the distal portion 1512. In addition, the proximal and distal components may be rigid or have rigid inner frames, formed, for example, of metal or PEEK, rather than a flexible material. The proximal component and distal component may threadedly connect to each other. Rotation of the proximal and distal components relative to each other may adjust the length, $L_3$, between the proximal portion 1510 and distal portion 1512 to capture tissue disposed between. A clinician may use a clip or other tool to hold the proximal component while rotating the distal component to adjust the length, $L_3$.

Figure 44:
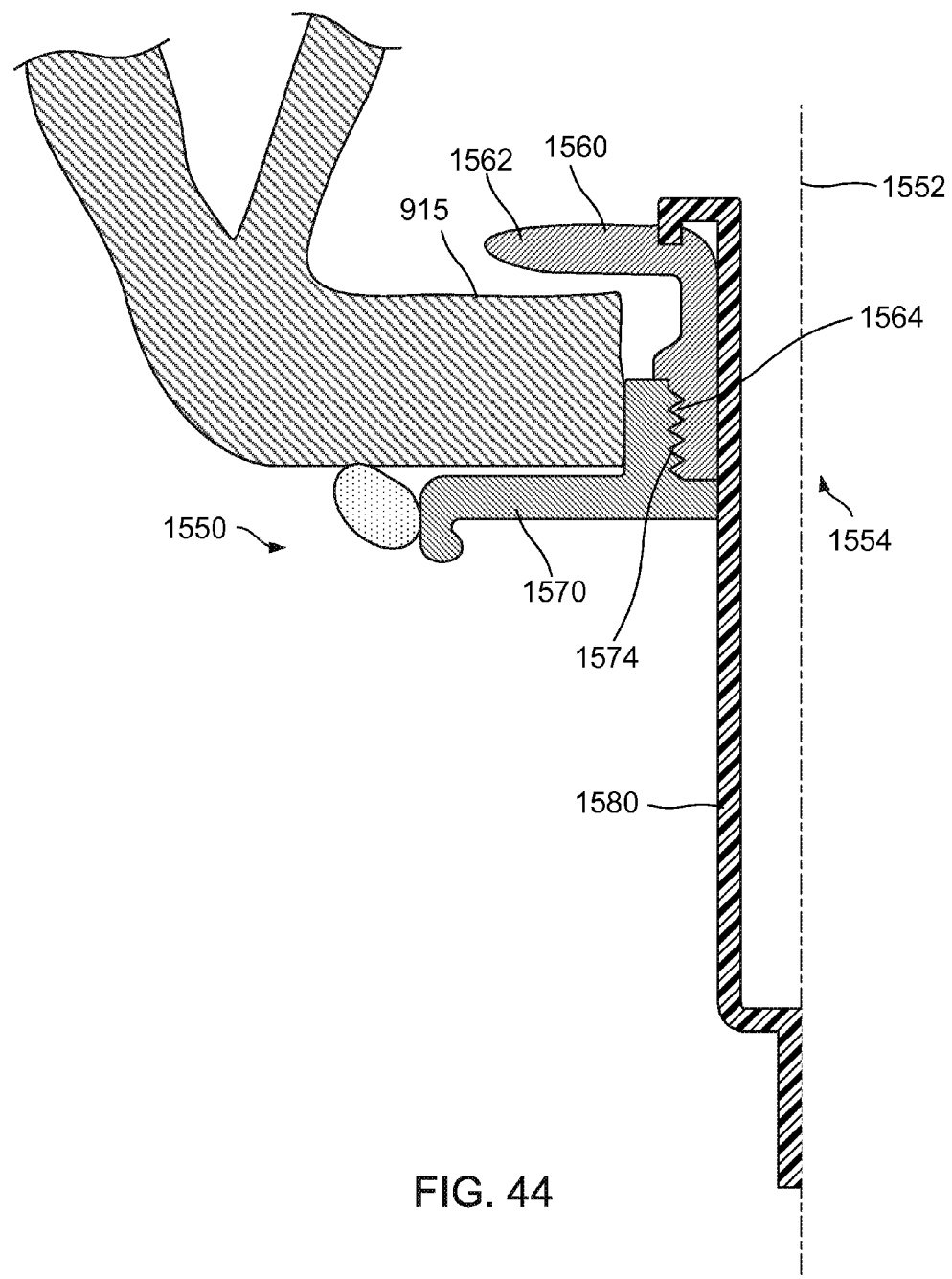

FIG. 44 shows an example of cuff 1550 that has a proximal component 1560 that can be adjusted relative to a distal component 1570. The proximal component 1560 has a portion 1562 that extends radially outward from an axis 1552 through a central opening 1554 in the cuff 1550. The proximal component 1560 also includes screw threads 1564 that mesh with screw threads 1574 of the distal component 1570. A clinician may use a tool 1580 to hold the proximal component 1560, while the proximal component 1560 and the distal component 1570 are rotated relative to each other to tighten the portion 1562 against the endocardium 915. This force may capture the myocardium between the proximal component 1560 and the distal component 1570. In some implementations, capture of the myocardium in this manner may be used to couple the cuff 1550 to the heart 914 without sutures or other fasteners.

In general, flattening of the myocardium may be achieved using one or more of the techniques described above. For example, the myocardium may be flattened using (i) sutures connected to the housing of a pump, (ii) a cuff having an appropriate flexural modulus, (iii) a member that extends into the heart to engage the endocardium, or (iv) capture of the myocardium from within and from outside the heart, or any combination or sub-combination thereof.

A number of implementations have been described. Nevertheless, it will be understood that various modifications may be made without departing from the spirit and scope of the disclosure. Implementations can include any appropriate combination or subcombination of features described above. For example, some of or all of the features described for the pumps 50, 250, 750, 912 cuffs 20, 120, 320, 620, 1240, 1500, 1550 cannulas 50, 150, 350, 650, 950, 1430, 1460 and clips 200, 700 can be combined or implemented individually. Accordingly, other implementations are within the scope of the following claims.

What is claimed is:

1. A method comprising:
attaching a cuff to a heart, the cuff comprising a sewing ring having a fabric material internally supported by an insert, and wherein the insert is configured to support the fabric material so as to increase a rigidity of the cuff such that at least a portion of a myocardium of the heart is flattened by the attaching;
forming an opening in the myocardium;
positioning an inflow cannula of a blood pump through a central opening in the cuff and into the opening in the myocardium; and
attaching the blood pump to the cuff;
wherein attaching the cuff to the heart causes at least a portion of the myocardium to flatten, and comprises conforming the myocardium to a shape of the cuff;
wherein a flexural modulus of the sewing ring is greater than 50 psi.

2. The method of claim 1, wherein the cuff comprises two or more layers of fabric.

3. The method of claim 2, wherein the insert is disposed between two or more layers of fabric, the insert being more rigid than the two or more layers of fabric.

4. The method of claim 1, further comprising attaching one or more sutures to one or more suture anchors disposed on an exterior of the blood pump.

5. The method of claim 4, wherein attaching the one or more sutures to one or more suture anchors comprises passing a suture through an eyelet disposed along an outer perimeter of the blood pump and through a portion of the cuff or the myocardium.

6. The method of claim 1, further comprising surrounding the blood pump within an implantable fabric cover defining a pocket around the blood pump.

7. A method of attaching a blood pump to a heart, the method comprising:
attaching a cuff to an outer surface of a myocardial wall of the heart;
wherein attaching the cuff to the heart causes at least a portion of the myocardial wall of the heart to flatten in a manner such that a geometry of the myocardial wall contacting a region of the cuff is flatter than a natural geometry of the myocardial wall;
positioning an inflow cannula of the blood pump relative to the cuff; and
coupling the blood pump to the cuff, wherein the flattening limits inflow cannula malposition;
wherein flattening comprises conforming the myocardial wall to a shape of the cuff, the cuff comprising a rigid sewing ring;
wherein a flexural modulus of the sewing ring is greater than 50 psi.

8. The method of claim 7, wherein flattening comprises expanding a space or distance between the inflow cannula and an inner surface of the myocardial wall.

9. The method of claim 7, wherein the flattening maintains a space or distance between the inflow cannula and an inner surface of the myocardial wall so as to limit partial or total occlusion of an inlet tip of the inflow cannula.

10. The method of claim 7, wherein flattening comprises reshaping an inner or outer surface of the myocardial wall along an entire region of the myocardial wall that is in contact with the cuff.

11. The method of claim 7, wherein flattening comprises reshaping the myocardial wall along a proximal side of the blood pump that is coupled to the cuff.

12. The method of claim 7, wherein the cuff comprises a planar sewing ring.

13. The method of claim 12, wherein the flexural modulus of the sewing ring is greater than 50 psi and up to 1500 psi.

14. The method of claim 7, wherein positioning comprises positioning the inflow cannula perpendicular to the cuff so that the cuff extends along a majority of a diameter of the heart pump.

15. The method of claim 7, wherein positioning comprises holding the cuff at the outer edge while the heart pump is subsequently positioned relative to the cuff.

16. The method of claim 15, wherein coupling comprises applying counter-pressure with the cuff against the inflow cannula so as to seat the cuff against the heart pump.

17. The method of claim 16, further comprising engaging a coupling mechanism and locking the cuff to the blood pump.

18. The method of claim 7, further comprising limiting rotation of the blood pump relative to the heart by fastening the blood pump through a portion of the cuff, the outer surface of the heart, or ribs.

19. The method of claim 7, further comprising forming an opening in the myocardial wall and positioning the inflow cannula of the blood pump through a central opening in the cuff and into the opening.

20. The method of claim 7, wherein the myocardial wall comprises a right or left ventricle.

21. The method of claim 1, wherein the insert comprises a shape memory material.

22. The method of claim 1, wherein the insert comprises a metal material.

23. The method of claim 1, wherein the insert is embedded within a sheet of silicone.

24. The method of claim 23, wherein the insert has openings defining areas where sutures may be placed through the insert and wherein the silicone covers the openings of the insert.

25. A method comprising:
attaching a cuff to a heart, the cuff comprising a fabric material supported by an insert, and wherein the insert is configured to support the fabric material so as to increase a rigidity of the cuff such that attaching the cuff to the heart causes at least a portion of a myocardium of the heart contacting a region of the cuff to conform to a shape of the cuff;
forming an opening in the myocardium;
positioning an inflow cannula of a blood pump through a central opening in the cuff and into the opening in the myocardium; and
attaching the blood pump to the cuff;
wherein the insert comprises an inner perimeter, an outer perimeter and a plurality of extensions that extend radially between the outer perimeter and the inner perimeter.

26. The method of claim 1, wherein flattening of the heart expands a space or distance between the inflow cannula and an inner surface of the myocardial wall.

27. The method of claim 1, wherein the flattening of the heart maintains a space or distance between the inflow cannula and an inner surface so as to limit partial or total occlusion of an inlet tip of the inflow cannula.

28. The method of claim 1, wherein the insert increases a rigidity of the cuff along an outer edge of the cuff.

29. The method of claim 7, wherein the flattening comprises using the cuff to flatten the portion of the myocardium, the cuff exerting a resilient force that resists bending of the cuff thereby flattening the myocardium.

30. The method of claim 7, wherein the flattened portion is an area of the myocardium in contact with the cuff.

31. The method of claim 7, further comprising manually reshaping the cuff to a desired configuration, and wherein the reshaped cuff shapes the myocardium to conform to the reshaped cuff.

* * * * *